US008044178B2

(12) United States Patent
Boghaert et al.

(10) Patent No.: US 8,044,178 B2
(45) Date of Patent: Oct. 25, 2011

(54) ANTI-5T4 ANTIBODIES AND USES THEREOF

(75) Inventors: Erwin R. Boghaert, Monroe, NY (US);
Nitin K. Damle, Upper Saddle River, NJ (US); Philip Ross Hamann, Thiells, NY (US); Kiran Khandke, Nanuet, NY (US); Arthur Kunz, New City, NY (US); Kimberly A. Marquette, Somerville, MA (US); Lioudmila Tchistiakova, Andover, MA (US); Davinder Gill, Andover, MA (US); Kodangattil Sreekumar, Plainsboro, NJ (US)

(73) Assignee: Wyeth LLC, Madison, NJ (US)

( * ) Notice: Subject to any disclaimer, the term of this patent is extended or adjusted under 35 U.S.C. 154(b) by 675 days.

(21) Appl. No.: 11/684,329

(22) Filed: Mar. 9, 2007

(65) Prior Publication Data

US 2007/0231333 A1 Oct. 4, 2007

Related U.S. Application Data

(60) Provisional application No. 60/891,248, filed on Feb. 23, 2007, provisional application No. 60/781,346, filed on Mar. 10, 2006.

(51) Int. Cl.
*C07K 16/00* (2006.01)
*C07K 17/00* (2006.01)
*C07K 17/14* (2006.01)
*C12P 21/08* (2006.01)
*A61K 39/395* (2006.01)
*A61K 39/00* (2006.01)

(52) U.S. Cl. ............... 530/387.1; 530/387.3; 530/387.9; 530/391.1; 530/391.7; 424/130.1; 424/133.1; 424/134.1; 424/178.1

(58) Field of Classification Search .......................... None
See application file for complete search history.

(56) References Cited

FOREIGN PATENT DOCUMENTS

| EP | 1130094 A2 * | 9/2001 |
|---|---|---|
| EP | 1 152 060 | 11/2001 |
| EP | 1 160 323 | 12/2001 |
| GB | 2 370 571 | 11/2001 |
| GB | 2 378 704 | 10/2002 |
| WO | 89/07947 | 9/1989 |
| WO | 91/09967 | 7/1991 |
| WO | 98/55607 | 12/1998 |
| WO | 02/096948 | 12/2002 |
| WO | 2006/031653 A | 3/2003 |
| WO | 03/038098 A | 5/2003 |
| WO | 2006/031653 | 3/2006 |
| WO | 2006/042158 A | 4/2006 |

OTHER PUBLICATIONS

Rudikoff et al (Proc Natl Acad Sci USA 1982 vol. 79 p. 1979).*
MacCallum et al. J. Mol. Biol. (1996) 262,732-745.*
Pascalis et al. The Journal of Immunology (2002) 169, 3076-3084.*
Casset et al. (2003) BBRC 307, 198-205.*
Vajdos et al. (2002) 320, 415-428.*
Holm et al. (2007)44, 1075-1084.*
Chen et al. J. Mol. Bio. (1999) 293, 865-881.*
Wu et al. J. Mol. Biol. (1999) 294, 151-162.*
Burgess, Shaheen, Ravera, Jaye, Donohue, and Winkles. Possible dissociation of the heparin binding and mitogenic activities of heparin-binding (acidic fibroblast) growth factor-1 from its receptor binding activities by site directed mutagenesis of a single lysine residue. Journal of Cell Biology, 1990. vol. 111, pp. 2129-2138.*
Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.*
Skolnick and Fetrow. From genes to protein structure and function: novel applications of computational approaches in the genomic era. Trends in Biotechnology, 2000. vol. 18, pp. 34-39.*
Muyldermans and Lauwereys. Unique single-domain antigen binding fragments derived from naturally occurring camel heavy-chain antibodies. Journal of Molecular Recognition, 1999. vol. 12, pp. 131-140.*
Harmsen and Haard. Properties, production and applications of camelid single-domain antibody fragments. Appl. Microbiol. Biotechnol., 2007. vol. 77, pp. 13-22.*
Forsberg, "Therapy of Human Non-small-cell Lung Carcinoma Using Antibody Targeting of a Modified Superantigen," British Journal of Cancer, Jul. 6, 2001, vol. 85, No. 1, pp. 129-136.
Shaw, "Isolation of a high affinity scFv from a monoclonal antibody recognising the oncofoetal antigen 5T4," Biochimica Et Biophysica Acta—General Subjects, Dec. 15, 2000, NL, vol. 1524, No. 2-3, pp. 238-246.
Shaw, "Glycosylation and epitope mapping of the 5T4 glycoprotein oncofoetal antigen," Biochemical Journal, Apr. 1, 2002, vol. 363, No. 1, pp. 137-145.
Myers, "Targeting Immune Effector Molecules to Human Tumor Cells Through Genetic Delivery of 5T4-specific scFv Fusion Proteins," Cancer Gene Therapy, Nov. 2002, vol. 9, No. 11, pp. 884-896.
Myers, "Isolation of a cDNA Encoding 5T4 Oncofetal Trophoblast Glycoprotein," Journal of Biological Chemistry, Mar. 25, 1994, vol. 269, No. 12, pp. 9319-9324.
Woods, "Characterization of the murine 5T4 oncofoetal antigen: A target for immunotherapy in cancer," Biochemical Journal, Aug. 15, 2002, London, GB, vol. 366, No. 1, pp. 353-365.
Ali et al., "The pattern of expression of the 5T4 oncofoetal antigen on normal, dysplastic and malignant oral mucosa," *Oral Oncology*, 2001, 37:57-64.
Altschul et al., "Basic Local Alignment Search Tool," *J. Mol. Biol.*, 1990, 215:403-410. Angal et al., "A Single Amino Acid Substitution Abolishes the Heterogeneity of Chimeric Mouse/Human (IgG4) Antibody," *Molecular Immunology*, 1993, 30(1):105-108.
Bakker et al., "Receptor Scintigraphy with a Radioiodinated Somatostatin Analogue: Radiolabeling, Purification, Biologic Activity, and In Vivo Application in Animals," *J. Nucl. Med.*, 1990, 31:1501-1509.
Batzer et al., "Enhanced evolutionary PCR using oligonucleotides with inosine at the 3'-terminus," *Nucleic Acids Research*, 1991, 19(18):5081.
Benincosa et al., "Pharmacokinetics and Pharmacodynamics of a Humanized Monoclonal Antibody to Factor IX in Cynomolgus Monkeys," *The Journal of Pharmacology and Experimental Therapeutics*, 2000, 292(2):810-816.
Boghaert et al., "Antibody-Targeted Chemotherapy with the Calicheamicin Conjugate hu3S193-*N*-Acetyl γ Gamma Calicheamicin Dimethyl Hydrazide Targets Lewis[y] and Eliminates Lewis[y]-Positive Human Carcinoma Cells and Xenografts," *Clinical Cancer Research*, 2004, 10:4538-4549.

(Continued)

*Primary Examiner* — Anne M. Gussow
(74) *Attorney, Agent, or Firm* — Womble Carlyle Sandridge & Rice, PLLC

(57) ABSTRACT

Anti-5T4 antibodies, anti-5T4 antibody/drug conjugates, and methods for preparing and using the same.

31 Claims, 27 Drawing Sheets

OTHER PUBLICATIONS

Chattopadhyay et al., "Purification and stabilization of $^{99m}$Tc-d,l-HMPAO: Role of organic extractants," *Nuclear Medicine and Biology*, 2001, 28:741-744.

Cheng et al., "Individualized Patient Dosing in Phase I Clinical Trials: The Role of Escalation with Overdose Control in PNU-214936," *Journal of Clinical Oncology*, 2004, 22(4):602-609.

Connor et al., "Loss of MHC Class-I Expression in Cervical Carcinomas," *Int. J. Cancer*, 1990, 46:1029-1034.

Crameri et al., "DNA shuffling of a family of genes from diverse species accelerates directed evolution," *Nature*, 1998, 391:288-291.

Dewanjee et al., "Noninvasive Imaging of c-myc Oncogene Messenger RNA with Indium-111-Antisense Probes in a Mammary Tumor-Bearing Mouse Model," *The Journal of Nuclear Medicine*, 1994, 35(6):1054-1063.

Forsberg et al., "Identification of Framework Residues in a Secreted Recombinant Antibody Fragment that Control Production Level and Localization in *Escherichia coli*," *The Journal of Biological Chemistry*, 1997, 272(19):12430-12436.

Forsberg et al., "Therapy of human non-small-cell lung carcinoma using antibody targeting of a modified superantigen," *British Journal of Cancer*, 2001, 85(1):129-136.

Gilewski et al., "An immunotherapeutic approach to treatment of breast cancer: focus on trastuzumab plus paclitaxel," *Cancer Chemother. Pharmacol.*, 2000, 46(Suppl):S23-S26.

Goldenberg et al., "The role of radiolabeled antibodies in the treatment of non-Hodgkin's lymphoma: the coming of age of radioimmunotherapy," *Critical Review of Oncology/Hematology*, 2001, 39:195-201.

Green et al., "Antigen-specific human monoclonal antibodies from mice engineered with human Ig heavy and light chain YACs," *Nature Genetics*, 1994, 7:13-21.

Hole et al., "A 72kD trophoblast glycoprotein defined by a monoclonal antibody," *Br. J. Cancer*, 1988, 57:239-246.

Hole et al., "Isolation and Characterization of 5T4, A Tumour-Associated Antigen," *Int. J. Cancer*, 1990, 45:179-184.

Houdebine et al., "Antibody manufacture in transgenic animals and comparisons with other system," *Current Opinion in Biotechnology*, 2002, 13:625-629.

Hoves et al., "The JAM-assay: optimized conditions to determine death-receptor-mediated apoptosis," *Methods*, 2003, 31:127-134.

Jones et al., "Investigation of expression of 5T4 antigen in cervical cancer," *Br. J. Cancer*, 1990, 61:96-100.

Jones et al., "Sensitive determination of cell Number using the CyQUANT® cell proliferation assay," *Journal of Immunological Methods*, 2001, 254:85-98.

Kalofonos et al., "Targeting of Tumours with Murine and Reshaped Human Monoclonal Antibodies Against Placental Alkaline Phosphatase: Immunolocalisation, Pharmacokinetics and Immune Response," *European Journal of Cancer*, 1994, 30A(12):1842-1850.

Krenning et al., Localisation of Endocrine-Related Tumours with Radioiodinated Analogue of Somatostatin, *The Lancet*, 1989, 242-244.

Liming et al., "Detection of B Lymphoma Cells Undergoing Apoptosis by Annexin-V Assay," *Chin. Med. Sci. J.*, 2002, 17(1):17-21.

Low et al., "Mimicking Somatic Hypermutation: Affinity Maturation of Antibodies Displayed on Bacteriophage Using a Bacterial Mutator Strain," *J. Mol. Biol.*, 1996, 260:359-368.

Magdelenat et al., "Tumour markers in oncology: past, present and future," *Journal of Immunological Methods*, 1992, 150:133-143.

Marks et al., "By-Passing Immunization: Building High Affinity Antibodies by Chain Shuffling," *Biotechnology*, 1992, 10:779-783.

Marks et al., "By-passing Immunization: Human Antibodies from V-gene Libraries Displayed on Phage," *J. Mol. Biol.*, 1991, 222:581-597.

Martin et al., "Modeling antibody hypervariable loops: A combined algorithm," *Proc. Natl. Acad. Sci.*, 1989, 86:9268-9272.

Martin et al., "Molecular Modeling of Antibody Combining Sites," *Methods in Enzymology*, 1991, 203:121-153.

Mieke et al., "Low Intercellular Adhesion Molecule 1 and High 5T4 Expression on Tumor Cells Correlate with Reduced Disease-free Survival in Colorectal Carcinoma Patients," *Clinical Cancer Research*, 1997, 3:1923-1930.

Morrison et al., "Chimeric human antibody molecules: Mouse antigen-binding domains with human constant region domains," *Proc. Natl. Acad. Sci. USA*, 1984, 81:6851-6855.

Mulryan et al., "Attenuated Recombinant Vaccinia Virus Expressing Oncofetal Antigen (Tumor-associated Antigen) 5T4 Induces Active Therapy of Established Tumors," *Molecular Cancer Therapeutics*, 2002, 1:1129-1137.

Myers et al., "Isolation of a cDNA Encoding 5T4 Oncofetal Trophoblast Glycoprotein," *The Journal of Biological Chemistry*, 1994, 269(12):9319-9324.

Myers et al., "Targeting immune effector molecules to human tumor cells through genetic delivery of 5T4-specific scFv fusion proteins," *Cancer Gene Therapy*, 2002, 9:884-896.

Naganuma et al., "Oncofetal Antigen 5T4 Expression as a Prognostic Factor in Patients with Gastric Cancer," *Anticancer Research*, 2002, 22:1033-1038.

Needleman et al., "A General Method Applicable to the Search for Similarities in the Amino Acid Sequence of Two Proteins," *J. Mol. Biol.*, 1970, 48:443-453.

Newman et al., "Primatization" of Recombinant Antibodies for Immunotherapy of Human Diseases: A Macaque/Human Chimeric Antibody Against Human CD4, *Biotechnology*, 1992, 10:1455-1460.

Ohtsuka et al., "An Alternative Approach to Deoxyoligonucleotides as Hybridization Probes by Insertion of Deoxyinosine at Ambiguous Codon Positions," *The Journal of Biological Chemistry*, 1985, 260(5):2605-2608.

Onn et al., "Development of an Orthotopic Model to Study the Biology and Therapy of Primary Human Lung Cancer in Nude Mice," *Clinical Cancer Research*, 2003, 9:5532-5539.

Padlan, "A Possible Procedure for Reducing the Immunogenicity of Antibody Variable Domains while Preserving their Ligand-Binding Properties," *Molecular Immunology*, 1991, 28(4/5):489-498.

Padlan et al., "Identification of specificity-determining residues in antibodies," *The FASEB Journal*, 1995, 9:133-139.

Patten et al., "Applications of DNA shuffling to pharmaceuticals and vaccines," *Current Opinion in Biotechnology*, 1997, 8:724-733.

Pearson et al., "Improved tools for biological sequence comparison," *Proc. Natl. Acad. Sci. USA*, 1988, 85:2444-2448.

Pedersen et al., "Antibody Modeling: Beyond Homology," *Immunomethods*, 1992, 1:126-136.

Potter et al., "Antibody Production in the Baculovirus Expression System," *Intern. Rev. Immunol.*, 1993, 10:103-112.

Queen et al., "A humanized antibody that binds to the interleukin 2 receptor," *Proc. Natl. Acad. Sci.*, 1989, 86:10029-10033.

Rees et al., "Antibody combining sites: structure and prediction," In Sternberg M.J.E. (ed.), *Protein Structure Prediction (1$^{st}$ ed.)*, Oxford Univ. Press, 1996, 140-172.

Reff et al., "Future of Monoclonal Antibodies in the Treatment of Hematologic Malignancies," *Cancer Control*, 2002, 9(2):152-166.

Rossolini et al., "Use of deoxyinosine-containing primers vs degenerate primers for polymerase chain reaction based on ambiguous sequence information," *Molecular and Cellular Probes*, 1994, 8:91-98.

Sagiuchi et al., "Transient seizure activity demonstrated by Tc-99m HMPAO SPECT and diffusion-weighted MR imaging," *Annals of Nuclear Medicine*, 2001, 15(3):267-270.

Schillberg et al., "Molecular farming of recombinant antibodies in plants," *Cell. Mol. Life Sci.*, 2003, 60:433-445.

Shaw et al., "Isolation of a high affinity scFv from a monoclonal antibody recognizing the oncofoetal antigen 5T4," *Biochimica et Biophysica Acta*, 2000, 1524:238-246.

Shaw et al., "Glycosylation and epitope mapping of the 5T4 glycoprotein oncofoetal antigen," *Biochem. J.*, 2002, 363:137-145.

Sievers et al., "Selective Ablation of Acute Myeloid Leukemia Using Antibody-Targeted Chemotherapy: A Phase I Study of an Anti-CD33 Calicheamicin Immunoconjugate," *Blood*, 1999, 93(11):3678-3684.

Smith et al., "Comparison of Biosequences," *Advances in Applied Mathematics*, 1981, 2:482-489.

Southall et al., "Immunohistological distribution of 5T4 antigen in normal and malignant tissues," *Br. J. Cancer,* 1990, 61:89-95.

Starzynska et al., "The expression of 5T4 antigen in colorectal and gastric carcinoma," *Br. J. Cancer,* 1992, 66:867-869.

Starzynska et al., "5T4 oncofetal antigen in gastric carcinoma and its clinical significance," *European Journal of Gastroenterology & Hepatology,* 1998, 10:479-484.

Stevenson et al., "A chimeric antibody with dual Fc regions (bisFabFc) prepared by manipulation at the IgG hinge," *Anti-Cancer Drug Design,* 1989, 3:219-230.

Subramanian et al., "Safety, tolerance and pharmacokinetics of a humanized monoclonal antibody to respiratory syncytial virus in premature infants and infants with bronchopulmonary dysplasia," *Pediatr. Infect. Dis. J.,* 1998, 17:110-115.

Thompson et al., "Affinity Maturation of a High-affinity Human Monoclonal Antibody Against the Third Hypervariable Loop of Human Immunodeficiency Virus: Use of Phage Display to Improve Affinity and Broaden Strain Reactivity," *J. Mol. Biol.,* 1996, 256:77-88.

Wolff et al., "Monoclonal Antibody Homodimers: Enhanced Antitumor Activity in Nude Mice," *Cancer Research,* 1993, 53:2560-2565.

Woods et al., "Characterization of the murine 5T4 oncofoetal antigen: a target for immunotherapy in cancer," *Biochem. J.,* 2002, 366:353-365.

Wrigley et al., "5T4 oncofetal antigen expression in ovarian carcinoma," *Int. J. Gynecol Cancer,* 1995, 5:269-274.

Yang et al., "CDR Walking Mutagenesis for the Affinity Maturation of a Potent Human Anti-HIV-1 Antibody into the Picomolar Range," *J. Mol. Biol.,* 1995, 254:392-403.

Yasuhara et al., "Comparison of Comet Assay, Electron Microscopy, and Flow Cytometry for Detection of Apoptosis," *The Journal of Histochemistry & Cytochemistry,* 2003, 51(7):873-885.

Yoo et al., "Technetium-99m Labeling and Biodistribution of Anti-TAC Disulfide-Stabilized Fv Fragment," *The Journal of Nuclear Medicine,* 1993, 38(2):294-300.

Yuhas et al., "A Simplified Method for Production and Growth of Multicellular Tumor Spheroids," *Cancer Research,* 1977, 37:3639-3643.

\* cited by examiner

FIG. 1A

Murine A1 VH

ATGGATTGGCTGTGGAACTTGCTATTCCTGATGGCAGCTGCCCAAAGTAT
CCAAGCACAGATCCAGTTGGTGCAGTCTGGACCTGAGCTGAAGAAGCCTG
GAGAGACAGTCAAGATCTCCTGCAAGGCTTCTGGATATACCTTCACAAAC
TTTGGAATGAACTGGGTGAAGCAGGGTCCAGGAGAGGGTTTAAAGTGGAT
GGGCTGGATAAACACCAACACTGGAGAGCCAAGATATGCTGAAGAGTTCA
AGGGACGGT(G/T)TGCCTTTTCTTTGGAAACCACTGCCAGCACTGCCTATTTG
CAGATCAACAACCTCAAAAATGAGGACACGGCTACATATTTCTGTGCAAG
AGACTGGGACGGTGCCTACTTCTTTGACTACTGGGGCCAAGGCACCACTC
TCACAGTCTCCTCA (SEQ ID NO:1)

MDWLWNLLFLMAAAQSIQAQIQLVQSGPELKKPGETVKISCKASGYTFTN
FGMNWVKQGPGEGLKWMGWINTNTGEPRYAEEFKGR(C/F)AFSLETTASTAYL
QINNLKNEDTATYFCARDWDGAYFFDYWGQGTTLTVSS (SEQ ID NO:2)

Murine A1 VL

ATGAAGTCACAGACCCAGGTCTTCGTATTTCTACTGCTCTGTGTGTCTGG
TGCTCATGGGAGTATTGTGATGACCCAGACTCCCAAATTCCTGCTTGTTT
CAGCAGGAGACAGGGTGACCATAACCTGCAAGGCCAGTCAGAGTGTGAGT
AATGATGTAGCTTGGTACCAACAGAAGCCAGGGCAGTCTCCTAAACTGTT
GATAAACTTTGCAACCAATCGCTACACTGGAGTCCCTAATCGCTTCACTG
GCAGTGGATATGGGACGGATTTCACTTTCACCATCAGCACTGTGCAGGCT
GAAGACCTGGCACTTTATTTCTGTCAGCAGGATTATAGCTCTCCGTGGAC
GTTCGGTGGAGGCACCAAGCTGGAAATCAAA (SEQ ID NO:3)

MKSQTQVFVFLLLCVSGAHGSIVMTQTPKFLLVSAGDRVTITCKASQSVS
NDVAWYQQKPGQSPKLLINFATNRYTGVPNRFTGSGYGTDFTFTISTVQA
EDLALYFCQQDYSSPWTFGGGTKLEIK (SEQ ID NO:4)

FIG. 1B

Murine A2 VH

ATGGAATGGAGGATCTTTCTCTTCATCCTGTCAGGAACTGCAGGTGTCCA
CTCCCAGGTTCAGCTGCAGCAGTCTAGACCTGAGCTGGTGAAGCCTGGGG
CTTCAGTGAAGATGTCCTGCAAGGCTTCTGGATACACTTTCACTGACTAT
GTTATAAGCTGGGTGAAGCAGAGAACTGGACAGGGCCTTGAGTGGATTGG
AGAGATTTATCCTGGAAGTAATAGTATTTATTACAATGAGAAGTTCAAGG
GCAGGGCCACACTGACTGCAGACAAATCCTCCAGCACAGCCTACATGCAG
CTCAGCAGCCTGACATCTGAGGACTCTGCGGTCTATTTCTGTGCAATGGG
GGGTAACTACGGCTTTGACTATTGGGGCCAAGGCACCACTCTCACAGTCT
CCTCA (SEQ ID NO:5)

MEWRIFLFILSGTAGVHSQVQLQQSRPELVKPGASVKMSCKASGYTFTDY
VISWVKQRTGQGLEWIGEIYPGSNSIYYNEKFKGRATLTADKSSSTAYMQ
LSSLTSEDSAVYFCAMGGNYGFDYWGQGTTLTVSS (SEQ ID NO:6)

Murine A2 VL

ATGGATTTTCAGGTGCAGATTTTCAGCTTCCTGCTAATCAGTGCCTCAGT
CATAATGTCCAGAGGACAAATTGTTCTCACCCAGTCTCCAGCAATCATGT
CTGCATCTCTAGGGGAACGGGTCACCTTGACCTGCACTGCCAGCTCAAGT
GTAAATTCCAATTACTTACACTGGTACCAGCAGAAGCCAGGATCCTCCCC
CAAACTCTGGATTTATAGCACATCCAACCTGGCTTCTGGAGTCCCAGCTC
GCTTCAGTGGCAGTGGGTCTGGGACCTCTTACTCTCTCACAATCAGCAGC
ATGGAGGCTGAAGATGCTGCCACTTATTACTGCCACCAGTATCATCGTTC
CCCGCTCACGTTCGGTGCTGGGACCAAGCTGGAGCTGAAA (SEQ ID NO:7)

MDFQVQIFSFLLISASVIMSRGQIVLTQSPAIMSASLGERVTLTCTASSS
VNSNYLHWYQQKPGSSPKLWIYSTSNLASGVPARFSGSGSGTSYSLTISS
MEAEDAATYYCHQYHRSPLTFGAGTKLELK (SEQ ID NO:8)

FIG. 1C

Murine A3 VH

ATGCTGTTGGGGCTGAAGTGGGTTTTCTTTGTTGTTTTTATCAAGGTGT
GCATTGTGAGGTGCAGCTTGTTGAGTCTGGTGGAGGATTGGTGCAGCCTA
AAGGGTCATTGAAACTCTCATGTGCAGCCTCTGGATTCACCTTCAATACC
TACGCCATGAACTGGGTCCGCCAGGCTCCAGGAAAGGGTTTGGAATGGGT
TGCTCGCATAAGAAGTAAAAGTAATAATTATGCAACATATTATGCCGATT
CAGTGAAAGACAGGTTCACCATCTCCAGAGATGATTCACAAAGCATGCTC
TATCTGCAAATGAACAACTTGAAAACTGAAGACACAGCCATGTATT(G/A)CTG
TGTGAGACAGTGGGATTACGACGTCAGGGCTATGAACTACTGGGGTCAAG
GAACCTCAGTCACCGTCTCCTCA (SEQ ID NO:9)

<u>MLLGLKWVFFVVFYQGVH</u>CEVQLVESGGGLVQPKGSLKLSCAAS<u>GFTFNT
YAMN</u>WVRQAPGKGLEWVA<u>RIRSKSNNYATYYADSVKD</u>RFTISRDDSQSML
YLQMNNLKTEDTAMY(C/Y)CVR<u>QWDYDVRAMNY</u>WGQGTSVTVSS (SEQ ID
NO:10)

Murine A3 VL

ATGGAGACACATTCTCAGGTCTTTGTATACATGTTGCTGTGGTTGTCTGG
TGTTGAAGGAGACATTGTGATGACCCAGTCTCACATATTCATGTCCACAT
CAGTAGGAGACAGGGTCAGCATCACCTGCAAGGCCAGTCAGGATGTGGAT
ACTGCTGTAGCCTGGTATCAACAGAAACCAGGGCAATCTCCTAAACTACT
GATTTACTGGGCATCCACCCGGCTCACTGGAGTCCCTGATCGCTTCACAG
GCAGTGGATCTGGGACGGATTTCACTCTCACCATTAGCAATGTGCAGTCT
GAAGACTTGGCAGATTATTTCTGTCAGCAATATAGCAGCTATCCGTACAC
GTTCGGAGGGGGGACCAAGCTGGAAATAAAA (SEQ ID NO:11)

<u>METHSQVFVYMLLWLSGVEG</u>DIVMTQSHIFMSTSVGDRVSITC<u>KASQDV D
TAVA</u>WYQQKPGQSPKLLIY<u>WASTRLT</u>GVPDRFTGSGSGTDFTLTISNVQS
EDLADYFC<u>QQYSSYPYT</u>FGGGTKLEIK (SEQ ID NO:12)

FIG. 8
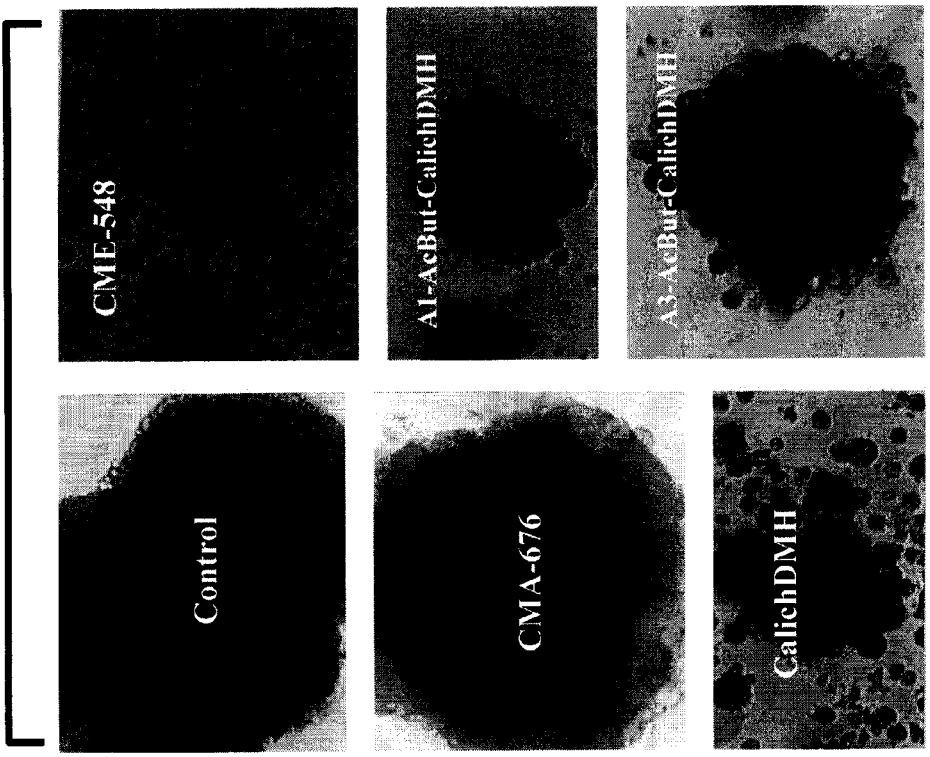
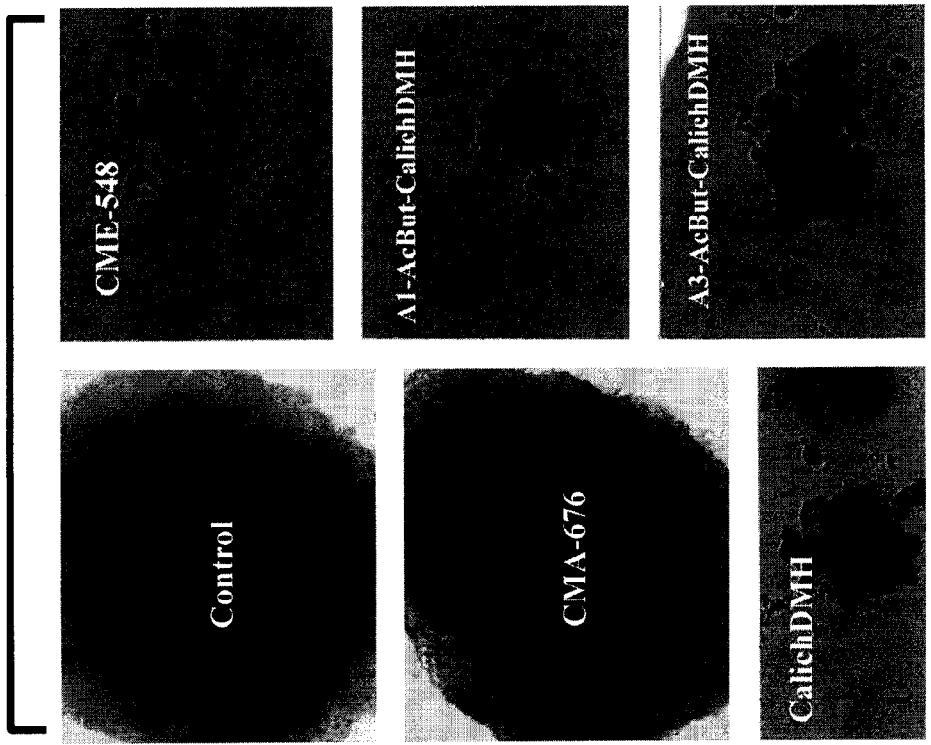

FIG. 9A

Humanized A1 VH-version 1.0 DNA

CAGGTGCAGCTGGTGCAATCTGGGTCTGAGTTGAAGAAGCCTGGGGCCTCAGTGAAGGT
TTCCTGCAAGGCTTCTGGATATACCTTCACAAACTTTGGAATGAACTGGGTGCGACAGG
CCCCTGGACAAGGGCTTAAGTGGATGGGATGGATAAACACCAACACTGGAGAGCCAAGA
TATGCTGAAGAGTTCAAGGGACGGTTTGTCTTCTCCTTGGACACCTCTGTCAGCACTGC
CTATCTGCAGATCTCCAGCCTGAAGGCTGAGGACACTGCCGTGTATTACTGTGCCAGAG
ACTGGGACGGTGCCTACTTCTTTGACTACTGGGGCCAAGGCACCCTTGTCACAGTCTCC
TCA(SEQ ID NO:48)

Humanized A1 VH-version 1.0 Protein

QVQLVQSGSELKKPGASVKVSCKAS<u>GYTFTNFGMN</u>WVRQAPGQGLKWMG<u>WINTNTGEPR
YAEEFKG</u>RFVFSLDTSVSTAYLQISSLKAEDTAVYYCARD<u>WDGAYFFDY</u>WGQGTLVTVS
S(SEQ ID NO:49)

Humanized A1 VH-version 1.1 DNA

CAGGTGCAGCTGGTGCAATCTGGGTCTGAGTTGAAGAAGCCTGGGGCCTCAGTGAAGGT
TTCCTGCAAGGCTTCTGGATATACCTTCACAAACTTTGGAATGAACTGGGTGCGACAGG
CCCCTGGACAAGGGCTTGAGTGGATGGGATGGATAAACACCAACACTGGAGAGCCAAGA
TATGCTGAAGAGTTCAAGGGACGGTTTGTCTTCTCCTTGGACACCTCTGTCAGCACTGC
CTATCTGCAGATCTCCAGCCTGAAGGCTGAGGACACTGCCGTGTATTACTGTGCCAGAG
ACTGGGACGGTGCCTACTTCTTTGACTACTGGGGCCAAGGCACCCTTGTCACAGTCTCC
TCA (SEQ ID NO:50)

Humanized A1 VH-version 1.1 Protein

QVQLVQSGSELKKPGASVKVSCKAS<u>GYTFTNFGMN</u>WVRQAPGQGLEWMG<u>WINTNTGEPR
YAEEFKG</u>RFVFSLDTSVSTAYLQISSLKAEDTAVYYCARD<u>WDGAYFFDY</u>WGQGTLVTVS
S (SEQ ID NO:51)

Humanized A1 VH-version 1.2 (CDR grafted into the DP-21 germline, VH7 sub-group)

QVQLVQSGSELKKPGASVKVSCKAS<u>GYTFTNFGMN</u>WVRQAPGQGLEWMG<u>WINTNTGEPR
YAEEFKG</u>RFVFSLDTSVSTAYLQICSLKAEDTAVYYCARD<u>WDGAYFFDY</u>WGQGTLVTVS
S (SEQ ID NO:52)

Any of the following amino acids could be substituted at these designated positions K46, C67, S82a and N82a.

FIG. 9B

Humanized A1 VH-version 2.0 DNA

GAGGTGCAGCTGGTGGAGTCTGGGGGAGGCTTGGTCCAGCCTGGGGGGTCCCTGAGACT
CTCCTGTGCAGCCTCTGGATATACCTTCACAAACTTTGGAATGAACTGGGTCCGCCAGG
CTCCAGGGAAGGGGCTGGAGTGGGTGGCCTGGATAAACACCAACACCGGTGAGCCAAGA
TATGCTGAAGAGTTCAAGGGACGATTCACCATCTCCAGAGACAACGCCAAGAACTCACT
GTATCTGCAAATGAACAGCCTGAGAGCCGAGGACACCGCTGTGTATTACTGTGCCAGAG
ACTGGGACGGTGCCTACTTCTTTGACTACTGGGGCCAAGGCACCCTTGTCACAGTCTCC
TCA (SEQ ID NO:53)

Humanized A1 VH-version 2.0 Protein (CDR grafted into the DP-54 germline, VH3 sub-group)

EVQLVESGGGLVQPGGSLRLSCAASGYTFTNFGMNWVRQAPGKGLEWVAWINTNTGEPR
YAEEFKGRFTISRDNAKNSLYLQMNSLRAEDTAVYYCARDWDGAYFFDYWGQGTLVTVS
S (SEQ ID NO:54)

Any of the following amino acids could be substituted at these designated positions K46, M48, G49, C67, L71, T73, T74, A75, S76 and A78.

Humanized A1 VH-version 2.1 DNA

GAGGTGCAGCTGGTGGAGTCTGGGGGAGGCTTGGTCCAGCCTGGGGGGTCCCTGAGACT
CTCCTGTGCAGCCTCTGGATATACCTTCACAAACTTTGGAATGAACTGGGTCCGCCAGG
CTCCAGGGAAGGGGCTGAAGTGGATGGGCTGGATAAACACCAACACCGGTGAGCCAAGA
TATGCTGAAGAGTTCAAGGGACGATTCACCATCTCCCTGGACAACGCCAAGTCCTCAGC
CTATCTGCAAATGAACAGCCTGAGAGCCGAGGACACCGCTGTGTATTACTGTGCCAGAG
ACTGGGACGGTGCCTACTTCTTTGACTACTGGGGCCAAGGCACCCTTGTCACAGTCTCC
TCA (SEQ ID NO:55)

Humanized A1 VH-version 2.1 Protein

EVQLVESGGGLVQPGGSLRLSCAASGYTFTNFGMNWVRQAPGKGLKWMGWINTNTGEPR
YAEEFKGRFTISLDNAKSSAYLQMNSLRAEDTAVYYCARDWDGAYFFDYWGQGTLVTVS
S (SEQ ID NO:56)

FIG. 9C

Humanized A1 VL-version 1.0 DNA

GACATCGTGATGACCCAGTCTCCAGACTCCCTGGCTGTGTCTCTGGGCGAGAGGGCCAC
CATCAACTGCAAGGCCAGTCAGAGTGTGAGTAATGATGTGGCTTGGTACCAGCAGAAAC
CAGGACAGCCTCCTAAGCTGCTCATTTACTTTGCAACCAATCGCTACACTGGAGTCCCT
GACCGCTTCTCCGGCAGCGGATCCGGCACAGATTTCACTCTCACCATCAGCAGCCTGCA
GGCTGAAGATGTGGCAGTTTATTACTGTCAGCAGGATTATAGCTCTCCCTGGACCTTCG
GTCAGGGCACCAAGGTGGAAATCAAA (SEQ ID NO:57)

Humanized A1 VL-version 1.0 Protein (CDR grafted into the DPK24 germline, VKIV sub-group)

DIVMTQSPDSLAVSLGERATINCKASQSVSNDVAWYQQKPGQPPKLLIYFATNRYTGVP
DRFSGSGSGTDFTLTISSLQAEDVAVYYCQQDYSSPWTFGQGTKVEIK(SEQ ID
NO:58)

Any of the following amino acids could be substituted at these designated positions S43, N49, N60, T63, Y67, F73, L85 and F87.

Humanized A1 VL-version 1.1 DNA

GACATCGTGATGACCCAGTCTCCAGACTCCCTGGCTGTGTCTCTGGGCGAGAGGGCCAC
CATCAACTGCAAGGCCAGTCAGAGTGTGAGTAATGATGTGGCTTGGTACCAGCAGAAAC
CAGGACAGCCTCCTAAGCTGCTCATTTACTTTGCAACCAATCGCTACACTGGAGTCCCT
GACCGCTTCTCCGGCAGCGGATACGGCACAGATTTCACTCTCACCATCAGCAGCCTGCA
GGCTGAAGATGTGGCAGTTTATTACTGTCAGCAGGATTATAGCTCTCCCTGGACCTTCG
GTCAGGGCACCAAGGTGGAAATCAAA (SEQ ID NO:59)

Humanized A1 VL-version 1.1 Protein

DIVMTQSPDSLAVSLGERATINCKASQSVSNDVAWYQQKPGQPPKLLIYFATNRYTGVP
DRFSGSGYGTDFTLTISSLQAEDVAVYYCQQDYSSPWTFGQGTKVEIK (SEQ ID
NO:60)

Humanized A1 VL-version 2.0 DNA

GACATCCAGATGACCCAGTCTCCATCCTCCCTGTCTGCATCTGTCGGAGACAGAGTCAC
CATCACTTGCAAGGCCAGTCAGAGTGTGAGTAATGATGTGGCTTGGTATCAGCAGAAAC
CAGGCAAAGCCCCTAAGCTCCTGATCTATTTTGCAACCAATCGCTACACTGGAGTCCCA
TCCCGCTTCAGCGGCAGCGGATCCGGCACAGATTTCACTCTCACCATCAGCAGCCTGCA
ACCTGAAGATTTTGCAACTTACTACTGTCAGCAGGATTATAGCTCTCCCTGGACCTTCG
GTCAGGGCACCAAGGTGGAAATCAAA (SEQ ID NO:61)

FIG. 9D

Humanized A1 VL-version 2.0 Protein (CDR grafted into the DPK9 germline, VKI sub-group)

DIQMTQSPSSLSASVGDRVTITC<u>KASQSVSNDVA</u>WYQQKPGKAPKLLIY<u>FATNRYT</u>GVP
SRFSGSGSGTDFTLTISSLQPEDFATYYC<u>QQDYSSPWT</u>FGQGTKVEIK (SEQ ID
NO:62)

Any of the following amino acids could be substituted at these designated positions V3, Q42, S43, N49, N60, Y67, F73, L85 and F87.

Humanized A1 VL-version 2.1 DNA

GACATCCAGATGACCCAGTCTCCATCCTCCCTGTCTGCATCTGTCGGAGACAGAGTCAC
CATCACTTGCAAGGCCAGTCAGAGTGTGAGTAATGATGTGGCTTGGTATCAGCAGAAAC
CAGGCAAATCCCCTAAGCTCCTGATCTATTTTGCAACCAATCGCTACACTGGAGTCCCA
TCCCGCTTCAGCGGCAGCGGATCCGGCACAGATTTCACTCTCACCATCAGCAGCCTGCA
ACCTGAAGATTTTGCAACTTACTACTGTCAGCAGGATTATAGCTCTCCCTGGACCTTCG
GTCAGGGCACCAAGGTGGAAATCAAA (SEQ ID NO:63)

Humanized A1 VL-version 2.1 Protein

DIQMTQSPSSLSASVGDRVTITC<u>KASQSVSNDVA</u>WYQQKPGKSPKLLIY<u>FATNRYT</u>GVP
SRFSGSGSGTDFTLTISSLQPEDFATYYC<u>QQDYSSPWT</u>FGQGTKVEIK (SEQ ID
NO:64)

Humanized A1 VL-version 2.2 DNA

GACATCCAGATGACCCAGTCTCCATCCTCCCTGTCTGCATCTGTCGGAGACAGAGTCAC
CATCACTTGCAAGGCCAGTCAGAGTGTGAGTAATGATGTGGCTTGGTATCAGCAGAAAC
CAGGCAAAGCCCCTAAGCTCCTGATCaATTTTGCAACCAATCGCTACACTGGAGTCCCA
TCCCGCTTCAGCGGCAGCGGATCCGGCACAGATTTCACTCTCACCATCAGCAGCCTGCA
ACCTGAAGATTTTGCAACTTACTACTGTCAGCAGGATTATAGCTCTCCCTGGACCTTCG
GTCAGGGCACCAAGGTGGAAATCAAA (SEQ ID NO:65)

Humanized A1 VL-version 2.2 Protein

DIQMTQSPSSLSASVGDRVTITC<u>KASQSVSNDVA</u>WYQQKPGKAPKLLIN<u>FATNRYT</u>GVP
SRFSGSGSGTDFTLTISSLQPEDFATYYC<u>QQDYSSPWT</u>FGQGTKVEIK (SEQ ID
NO:66)

FIG. 9E

Humanized A1 VL-version 2.3 DNA

GACATCCAGATGACCCAGTCTCCATCCTCCCTGTCTGCATCTGTCGGAGACAGAGTCAC
CATCACTTGCAAGGCCAGTCAGAGTGTGAGTAATGATGTGGCTTGGTATCAGCAGAAAC
CAGGCAAAGCCCCTAAGCTCCTGATCTATTTTGCAACCAATCGCTACACTGGAGTCCCA
AACCGCTTCAGCGGCAGCGGATCCGGCACAGATTTCACTCTCACCATCAGCAGCCTGCA
ACCTGAAGATTTTGCAACTTACTACTGTCAGCAGGATTATAGCTCTCCCTGGACCTTCG
GTCAGGGCACCAAGGTGGAAATCAAA (SEQ ID NO:67)

Humanized A1 VL-version 2.3 Protein

DIQMTQSPSSLSASVGDRVTITCKASQSVSNDVAWYQQKPGKAPKLLIYFATNRYTGVP
NRFSGSGSGTDFTLTISSLQPEDFATYYCQQDYSSPWTFGQGTKVEIK (SEQ ID
NO:68)

Humanized A1 VL-version 2.4 DNA

GACATCCAGATGACCCAGTCTCCATCCTCCCTGTCTGCATCTGTCGGAGACAGAGTCAC
CATCACTTGCAAGGCCAGTCAGAGTGTGAGTAATGATGTGGCTTGGTATCAGCAGAAAC
CAGGCAAAGCCCCTAAGCTCCTGATCTATTTTGCAACCAATCGCTACACTGGAGTCCCA
TCCCGCTTCAGCGGCAGCGGATACGGCACAGATTTCACTCTCACCATCAGCAGCCTGCA
ACCTGAAGATTTTGCAACTTACTACTGTCAGCAGGATTATAGCTCTCCCTGGACCTTCG
GTCAGGGCACCAAGGTGGAAATCAAA (SEQ ID NO:69)

Humanized A1 VL-version 2.4 Protein

DIQMTQSPSSLSASVGDRVTITCKASQSVSNDVAWYQQKPGKAPKLLIYFATNRYTGVP
SRFSGSGYGTDFTLTISSLQPEDFATYYCQQDYSSPWTFGQGTKVEIK (SEQ ID
NO:70)

Humanized A1 VL-version 2.5 DNA

GACATCCAGATGACCCAGTCTCCATCCTCCCTGTCTGCATCTGTCGGAGACAGAGTCAC
CATCACTTGCAAGGCCAGTCAGAGTGTGAGTAATGATGTGGCTTGGTATCAGCAGAAAC
CAGGCAAAGCCCCTAAGCTCCTGATCTATTTTGCAACCAATCGCTACACTGGAGTCCCA
TCCCGCTTCAGCGGCAGCGGATCCGGCACAGATTTCACTTTCACCATCAGCAGCCTGCA
ACCTGAAGATTTTGCAACTTACTACTGTCAGCAGGATTATAGCTCTCCCTGGACCTTCG
GTCAGGGCACCAAGGTGGAAATCAAA (SEQ ID NO:71)

Humanized A1 VL-version 2.5 Protein

DIQMTQSPSSLSASVGDRVTITCKASQSVSNDVAWYQQKPGKAPKLLIYFATNRYTGVP
SRFSGSGSGTDFTFTISSLQPEDFATYYCQQDYSSPWTFGQGTKVEIK (SEQ ID
NO:72)

FIG. 9F

Humanized A1 VL-version 3.0 DNA

GAAATTGTGATGACACAGTCTCCAGCCACCCTGTCCCTGTCTCCAGGCGAAAGAGCCAC
CCTCTCCTGCAAGGCCAGTCAGAGTGTGAGTAATGATGTGGCTTGGTACCAGCAGAAAC
CTGGGCAGGCTCCCAGGCTGCTGATCTATTTTGCAACCAATCGCTACACTGGCATCCCA
GCCCGCTTCTCCGGCAGCGGCTCCGGCACAGACTTCACTCTCACCATCAGCAGCCTGCA
GCCTGAAGATTTTGCAGTTTATTACTGTCAGCAGGATTATAGCTCTCCCTGGACCTTCG
GTCAGGGCACCAAGGTGGAAATCAAA (SEQ ID NO:73)

Humanized A1 VL-version 3.0 Protein (CDR grafted into the DPK23 germline, VKIII sub-group)

EIVMTQSPATLSLSPGERATLSC<u>KASQSVSNDVA</u>WYQQKPGQAPRLLIY<u>FATNRYT</u>GIP
ARFSGSGSGTDFTLTISSLQPEDFAVYYC<u>QQDYSSPWT</u>FGQGTKVEIK (SEQ ID
NO:74)

Any of the following amino acids could be substituted at these designated positions F10, S43, N49, V58, N60, Y67, F73, L85 and F87.

Humanized A1 VL-version 3.1 DNA

GAAATTGTGATGACACAGTCTCCAGCCACCCTGTCCCTGTCTCCAGGCGAAAGAGCCAC
CCTCTCCTGCAAGGCCAGTCAGAGTGTGAGTAATGATGTGGCTTGGTACCAGCAGAAAC
CTGGGCAGGCTCCCAGGCTGCTGATCTATTTTGCAACCAATCGCTACACTGGCATCCCA
GCCCGCTTCTCCGGCAGCGGCTACGGCACAGACTTCACTCTCACCATCAGCAGCCTGCA
GCCTGAAGATTTTGCAGTTTATTACTGTCAGCAGGATTATAGCTCTCCCTGGACCTTCG
GTCAGGGCACCAAGGTGGAAATCAAA (SEQ ID NO:75)

Humanized A1 VL-version 3.1 Protein

EIVMTQSPATLSLSPGERATLSC<u>KASQSVSNDVA</u>WYQQKPGQAPRLLIY<u>FATNRYT</u>GIP
ARFSGSGYGTDFTLTISSLQPEDFAVYYC<u>QQDYSSPWT</u>FGQGTKVEIK (SEQ ID
NO:76)

FIG. 9G huA2 VH Version 1.0 (CDR grafted into the DP-75 germline, VH1 subgroup)

QVQLVQSGAEVKKPGASVKVSCKAS<u>GYTFTDYVIS</u>WVRQAPGQGLEWMG<u>EIYPGSNSIY
YNEKFKG</u>RVTMTRDTSISTAYMELSRLRSDDTAVYYCAR<u>GGNYGFDY</u>WGQGTLVTVSS
(SEQ ID NO:77)

Any of the following amino acids could be substituted at these designated positions K38, R40, T41, I48, I69, T75, Q81, S82b, E85 and M94.

huA2 VH Version 2.0 (CDR grafted into the DP-54 germline, VH3 subgroup)

EVQLVESGGGLVQPGGSLRLSCAAS<u>GYTFTDYVIS</u>WVRQAPGKGLEWVA<u>EIYPGSNSIY
YNEKFKG</u>RFTISRDNAKNSLYLQMNSLRAEDTAVYYCAR<u>GGNYGFDY</u>WGQGTLVTVSS
(SEQ ID NO:78)

Any of the following amino acids could be substituted at these designated positions K38, R40, T41, I48, G49, A67, A71, K73, S74, S76, A78 and M94.

huA2 VL Version 1.0 (CDR grafted into the DPK20 germline, VKIII subgroup)

EIVLTQSPATLSLSPGERATLSC<u>TASSSVNSNYLH</u>WYQQKPGLAPRLLIY<u>STSNLASG</u>I
PDRFSGSGSGTDFTLTISRLEPEDFAVYYC<u>HQYHRSPLT</u>FGGGTKVEIK (SEQ ID NO:79)

Any of the following amino acids could be substituted at these designated positions S43, W47, A60, S70, S77, M78, and A80.

huA2 VL Version 2.0 (CDR grafted into the DPK9 germline, VKI subgroup)

DIQMTQSPSSLSASVGDRVTITC<u>TASSSVNSNYLH</u>WYQQKPGKAPKLLIY<u>STSNLASG</u>V
PSRFSGSGSGTDFTLTISSLQPEDFATYYC<u>HQYHRSPLT</u>FGGGTKVEIK (SEQ ID NO:80)

Any of the following amino acids could be substituted at these designated positions V3, L4, S43, W47, S70, and M78.

FIG. 9H huA3 VH Version 1.0 (CDR grafted into the DP-29 germline, VH3 subgroup)

EVQLVESGGGLVQPGGSLRLSCAASGFTFNTYAMNWVRQAPGKGLEWVGRIRSKSNNYA
TYYADSVKDRFTISRDDSKNSLYLQMNSLKTEDTAVYYCARQWDYDVRAMNYWGQGTLV
TVSS (SEQ ID NO:81)

Any of the following amino acids could be substituted at these designated positions A49, Q75, S76, M89, C91 and V93.

huA3 VH Version 2.0 (CDR grafted into the DP-54 germline, VH3 subgroup)

EVQLVESGGGLVQPGGSLRLSCAASGFTFNTYAMNWVRQAPGKGLEWVARIRSKSNNYA
TYYADSVKDRFTISRDNAKNSLYLQMNSLRAEDTAVYYCARQWDYDVRAMNYWGQGTLV
TVSS (SEQ ID NO:82)

Any of the following amino acids could be substituted at these designated positions D73, Q75, S76, M89, C91 and V93.

huA3 VL Version 1.0 (CDR grafted into the DPK24 germline, VKIV sub-group)

DIVMTQSPDSLAVSLGERATINCKASQDVDTAVAWYQQKPGQPPKLLIYWASTRLTGVP
DRFSGSGSGTDFTLTISSLQAEDVAVYYCQQYSSYPYTFGQGTKLEIK (SEQ ID NO:83)

Any of the following amino acids could be substituted at these designated positions S43, D85 and F87.

huA3 VL Version 2.0 (CDR grafted into the DPK9 germline, VKI subgroup)

DIQMTQSPSSLSASVGDRVTITCKASQDVDTAVAWYQQKPGKAPKLLIYWASTRLTGVP
SRFSGSGSGTDFTLTISSLQPEDFATYYCQQYSSYPYTFGQGTKLEIK (SEQ ID NO:84)

Any of the following amino acids could be substituted at these designated positions 3V, Q42, S43, D60, D85 and F87.

FIG. 10A

| | | FR1 | CDR1 | FR2 | CDR2 | FR3 | SEQ ID NO. 25-27 |
|---|---|---|---|---|---|---|---|
| | | QVQLVQSGAEVKKPGASVKVSCKASGYTFT | | WVRQAPGQGLEWMG | | RVTITRDTSTSTAYMELSSLRSEDTAVYYCAR | |
| 1-3 | 1-02 | QVQLVQSGAEVKKPGASVKVSCKASGYTFT | G--YYMH | WVRQAPGQGLEWMG | WINP--NSGGTNYAQKFQG | RVTMTRDTSISTAYMELSRLRSRLRSDDTAVYYCAR | 14 |
| 1-3 | 1-03 | QVQLVQSGAEVKKPGASVKVSCKASGYTFT | S--YAMH | WVRQAPGQRLEWMG | WINA--GNGNTKYSQKFQG | RVTITRDTSASTAYMELSSLRSEDTAVYYCAR | 15 |
| 1-3 | 1-08 | QVQLVQSGAEVKKPGASVKVSCKASGYTFT | S--YDIN | WVRQATGQGLEWMG | WMNP--NSGNTGYAQKFQG | RVTMTRNTSISTAYMELSSLRSEDTAVYYCAR | 16 |
| 1-2 | 1-18 | QVQLVQSGAEVKKPGASVKVSCKASGYTFT | S--YGIS | WVRQAPGQGLEWMG | WISA--YNGNTNYAQKLQG | RVTMTTDTSTSTAYMELRSLRSDDTAVYYCAR | 17 |
| 1-U | 1-24 | QMQLVQSGAEVKKTGSSVKVSCKVSGYTLT | E--LSMH | WVRQAPGKGLEWMG | GFDP--EDGETIYAQKFQG | RVTMTEDTSTDTAYMELSSLRSEDTAVYYCAT | 18 |
| 1-3 | 1-45 | QVQLVQSGAEVKKTGSSVKVSCKASGYTFT | Y--RYLH | WVRQAPGQALEWMG | WITP--FNGNTNYAQKFQD | RVTITRDRSMSTAYMELSSLRSEDTAMYYCAR | 19 |
| 1-3 | 1-46 | QVQLVQSGAEVKKPGASVKVSCKASGYTFT | S--YYMH | WVRQAPGQGLEWMG | IINP--SGGSTSYAQKFQG | RVTMTRDTSTVYMELSSLRSEDTAVYYCAR | 20 |
| 1-3 | 1-58 | QMQLVQSGPEVKKPGTSVKVSCKASGFTFT | S--SAVQ | WVRQARGQRLEWIG | WIVV--GSGNTNYAQKFQE | RVTITRDMSTSTAYMELSSLRSEDTAVYYCAA | 21 |
| 1-2 | 1-69 | QVQLVQSGAEVKKPGSSVKVSCKASGGTFS | S--YAIS | WVRQAPGQGLEWMG | GIIP--IFGTANYAQKFQG | RVTITADESTSTAYMELSSLRSEDTAVYYCAR | 22 |
| 1-2 | 1-e | QVQLVQSGAEVKKPGSSVKVSCKASGGTFS | S--YAIS | WVRQAPGQGLEWMG | GIIP--IFGTANYAQKFQG | RVTITADKSTSTAYMELSSLRSEDTAVYYCAR | 23 |
| 1-2 | 1-f | EVQLVQSGAEVKKPGATVKISCKVSGYTFT | D--YYMH | WVQQAPGKGLEWMG | LVDP--EDGETIYAEKFQG | RVTITADTSTDTAYMELSSLRSEDTAVYYCAT | 24 |

FIG. 10B

Amino acid sequences of human germline genes of VH 7 subgroup

DP-21 (VH 7) GenBank Accession No. CAA43346 (SEQ ID NO:88)

QVQLVQSGSELKKPGASVKVSCKASGYTFTSYAMNWVRQAPGQGLEWMGWIN
TNTGNPTYAQGFTGRFVFSLDTSVSTAYLQISSLKAEDTAVYYCARDSRGYSYDF
WSGYFYYYMDVWGKGTTVTVSS

Amino acid sequences of human germline genes of VH 3 subgroup

DP-54 (VH 3-07) GenBank Accession No. AB019440 (SEQ ID NO:89)

EVQLVESGGGLVQPGGSLRLSCAASGFTFSSYWMSWVRQAPGKGLEWVANIKQ
DGSEKYYVDSVKGRFTISRDNAKNSLYLQMNSLRAEDTAVYYCAR

DP-47 (VH3-23) GenBank Accession No. AB019439 (SEQ ID NO:90)

EVQLLESGGGLVQPGGSLRLSCAASGFTFSSYAMSWVRQAPGKGLEWVSAISGS
GGSTYYADSVKGRFTISRDNSKNTLYLQMNSLRAEDTAVYYCAK

DP-49 (VH 3-30) GenBank Accession No. AB019439 (SEQ ID NO:91)

QVQLVESGGGVVQPGRSLRLSCAASGFTFSSYGMHWVRQAPGKGLEWVAVISY
DGSNKYYADSVKGRFTISRDNSKNTLYLQMNSLRAEDTAVYYCAR

DP-53 (VH3-74) GenBank Accession No. AB019437 (SEQ ID NO:92)

EVQLVESGGGLVQPGGSLRLSCAASGFTFSSYWMHWVRQAPGKGLVWVSRINS
DGSSTSYADSVKGRFTISRDNAKNTLYLQMNSLRAEDTAVYYCAR

DP-48 (VH3-13) GenBank Accession No.AB019440 (SEQ ID NO:93)

EVQLVESGGGLVQPGGSLRLSCAASGFTFSSYDMHWVRQATGKGLEWVSAIGT
AGDTYYPGSVKGRFTISRENAKNSLYLQMNSLRAGDTAVYYCAR

FIG. 11

| SEQ ID NO. | | CDR1 | | | |
|---|---|---|---|---|---|
| 29 | L16_germline | ...EIVMTQS | PATLSVSPGE | RATLSCRASQ | SVSS.NLAWY QQKPGQAPRL |
| 30 | L2_germline | ...EIVMTQS | PATLSVSPGE | RATLSCRASQ | SVSS.NLAWY QQKPGQAPRL |
| 31 | A27_germl_VL | ...EIVLTQS | PGTLSLSPGE | RATLSCRASQ | SVSSSYLAWY QQKPGQAPRL |
| 32 | L6_germl_VL | ...EIVLTQS | PATLSLSPGE | RATLSCRASQ | SVSS.YLAWY QQKPGQAPRL |
| 33 | L10_germl_VL | ...EIVMTQS | PPTLSLSPGE | RVTLSCRASQ | SVSSSYLTWY QQKPGQAPRL |
| 34 | L25_geml_VL | EIVMTQS | PATLSLSPGE | RATLSCRASQ | SVSSSYLSWY QQKPGQAPRL |

| SEQ ID NO. | | CDR2 | | | CDR3 | |
|---|---|---|---|---|---|---|
| 29 | L16_germline | LIYGASTRAT | GIPARFSGSG | SGTEFTLTIS | SLQSEDFAVY YCQQYNNWPP | TV |
| 30 | L2_germline | LIYGASTRAT | GIPARFSGSG | SGTEFTLTIS | SLQSEDFAVY YCQQYNNWP. | . |
| 31 | A27_germl_VL | LIYGASSRAT | GIPDRFSGSG | SGTDFTLTIS | RLEPEDFAVY YCQQYGSSP. | . |
| 32 | L6_germl_VL | LIYDASNRAT | GIPARFSGSG | SGTDFTLTIS | SLEPEDFAVY YCQQRSNWP. | . |
| 33 | L10_germl_VL | LIYGASTRAT | SIPARFSGSG | SGTDFTLTIS | SLQPEDFAVY YCQQDHNLP. | . |
| 34 | L25_geml_VL | LIYGASTRAT | GIPARFSGSG | SGTDFTLTIS | SLQPEDFAVY YCQQDYNLP. | . |

FIG. 12

| SEQ ID NO. | | ---FR1--- | ---CDR1--- | | ---FR2--- | ---CDR2--- | ---FR3--- | ---CDR3--- |
|---|---|---|---|---|---|---|---|---|
| 35 | O12 | DIQMTQSPSSLSASVGDRVTITC | RASQSISS | ----YLN | WYQQKPGKAPKLLIY | AASSLQS | GVPSRFSGSGSGTDFTLTISSLQPEDFATYYC | QQSYSTP |
| 36 | O2 | DIQMTQSPSSLSASVGDRVTITC | RASQSISS | ----YLN | WYQQKPGKAPKLLIY | AASSLQS | GVPSRFSGSGSGTDFTLTISSLQPEDFATYYC | QQSYSTP |
| 37 | O18 | DIQMTQSPSSLSASVGDRVTITC | QASQDISN | ----YLN | WYQQKPGKAPKLLIY | DASNLET | GVPSRFSGSGSGTDFTFTISSLQPEDIATYYC | QQYDNLP |
| 38 | O8 | DIQMTQSPSSLSASVGDRVTITC | QASQDISN | ----YLN | WYQQKPGKAPKLLIY | DASNLET | GVPSRFSGSGSGTDFTFTISSLQPEDIATYYC | QQYDNLP |
| 39 | A20 | DIQMTQSPSSLSASVGDRVTITC | RASQGISN | ----YLA | WYQQKPGKVPKLLIY | AASTLQS | GVPSRFSGSGSGTDFTLTISSLQPEDVATYYC | QKYNSAP |
| 40 | L1 | DIQMTQSPSSLSASVGDRVTITC | RASQGISN | ----YLA | WFQQKPGKAPKLLIY | AASSLQS | GVPSRFSGSGSGTDFTLTISSLQPEDFATYYC | QQYNSYP |
| 41 | L15 | DIQMTQSPSSLSASVGDRVTITC | RASQGISS | ----WLA | WYQQKPEKAPKSLIY | AASSLQS | GVPSRFSGSGSGTDFTLTISSLQPEDFATYYC | QQYNSYP |
| 42 | L8 | DIQLTQSPSFLSASVGDRVTITC | RASQGISS | ----YLA | WYQQKPGKAPKLLIY | AASTLQS | GVPSRFSGSGSGTEFTLTISSLQPEDFATYYC | QQLNSYP |
| 43 | L12 | DIQMTQSPSTLSASVGDRVTITC | RASQSISS | ----WLA | WYQQKPGKAPKLLIY | DASSLES | GVPSRFSGSGSGTEFTLTISSLQPDDFATYYC | QQYNSYS |
| 44 | L11 | AIQMTQSPSSLSASVGDRVTITC | RASQSISS | ----WLA | WYQQKPGKAPKLLIY | DASSLES | GVPSRFSGSGSGTDFTLTISSLQPEDFATYYC | QQYNSYS |

FIG. 13

Amino acid sequences of human germline genes of Vk I subgroup

DPK9 (O12, Vk 1) GenBank Accession No. X59315 (SEQ ID NO:94)

DIQMTQSPSSLSASVGDRVTITCRASQSISSYLNWYQQKPGKAPKLLIYAASSLQS
GVPSRFSGSGSGTDFTLTISSLQPEDFATYYCQQSYSTP

O2 (O2, Vk 1) GenBank Accession No. X59312 (SEQ ID NO:95)

DIQMTQSPSSLSASVGDRVTITCRASQSISSYLNWYQQKPGKAPKLLIYAASSLQS
GVPSRFSGSGSGTDFTLTISSLQPEDFATYYCQQSYSTP

DPK 1 (Vk I, )18) GenBank Accession No. M64856 (SEQ ID NO:96)

DIQMTQSPSSLSASVGDRVTITCQASQDISNYLNWYQQKPGKAPKLLIYDASNLE
TGVPSRFSGSGSGTDFTFTISSLQPEDIATYYCQQYDNLP

DPK 7 (Vk I, L15) GenBank Accession No. K01323 (SEQ ID NO:97)

DIQMTQSPSSLSASVGDRVTITCRASQGISSWLAWYQQKPEKAPKSLIYAASSLQS
GVPSRFSGSGSGTDFTLTISSLQPEDFATYYCQQYNSYP

Amino acid sequences of human germline genes of Vk IV subgroup

DPK24 ( B3, VkIV) GenBank Accession No. Z00023 (SEQ ID NO:98)

DIVMTQSPDSLAVSLGERATINCKSSQSVLYSSNNKNYLAWYQQKPGQPPKLLIY
WASTRESGVPDRFSGSGSGTDFTLTISSLQAEDVAVYYCQQYYSTP

Amino acid sequences of human germline genes of Vk III subgroup

DPK 23 (Vk-III, L25) GenBank Accession No. X72820 (SEQ ID NO:99)

EIVMTQSPATLSLSPGERATLSCRASQSVSSSYLSWYQQKPGQAPRLLIYGASTRA
TGIPARFSGSGSGTDFTLTISSLQPEDFAVYYCQQDYNLP

FIG. 14

Human IgG4_mutated (hinge mutation S241P) (SEQ ID NO:45)

ASTKGPSVFPLAPCSRSTSESTAALGCLVKDYFPEPVTVSWNSGALTSGVHTFPAVLQS
SGLYSLSSVVTVPSSSLGTKTYTCNVDHKPSNTKVDKRVESKYGPPCPPCPAPEFLGGP
SVFLFPPKPKDTLMISRTPEVTCVVVDVSQEDPEVQFNWYVDGVEVHNAKTKPREEQFN
STYRVVSVLTVLHQDWLNGKEYKCKVSNKGLPSSIEKTISKAKGQPREPQVYTLPPSQE
EMTKNQVSLTCLVKGFYPSDIAVEWESNGQPENNYKTTPPVLDSDGSFFLYSRLTVDKS
RWQEGNVFSCSVMHEALHNHYTQKSLSLSLGK

Human IgG1 (SEQ ID NO:46)

ASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPP
SREEMTKNQVSLTCLVKGFYPSDIAVEWESNGQPENNYKTTPPVLDSDGSFFLYSKLTV
DKSRWQQGNVFSCSVMHEALHNHYTQKSLSLSPGK

Human Kappa (SEQ ID NO:47)

TVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

FIG. 15

Black-tailed Marmoset 5T4

MPGGCSRGPAAGNGRLRLARLALVLLGWVSSSSPTSSASSSSSSAPFLASAVSAQPLLP
GQCPALCECSEAARTVKCVNRNLTEVPTDLPPYVRNLFLTGNQLAVLPAGAFARVPPLA
ELAALNLSGSRLEDVQAGAFEHLPSLRQLDLSHNPLAVLSPFAFSGSNASVSAPSPLVE
LILNHIVPPEDERNNRSFEGMVVAALRAGGALHGLHRLELASNHFLYLPRDVLAQLPSL
RHLDLSNNSLVSLTYVSFRNLTHLESLHLEDNALKVLHNGTLAELQGLPHVRVFLDNNP
WVCDCHMADMVAWLKETEVVQGKYQLTCAFPEKMRNRVLLELNSADLDCDPILPPSLQT
SYVFLGIVLALIG (SEQ ID NO:85)

Cynomologous monkey 5T4

MPGGCSRGPAAGDGRLRLARLALVLLGWVSSSSPTSSASSFSSSAPFLASAASAQPPLP
DQCPALCECSEAARTVKCVNRNLTEVPTDLPLYVRNLFLTGNQLAVLPAGAFARRPPLA
ELAALNLSGSRLDEVRAGAFEHLPSLRQLDLSHNPLAYLSPFAFSGSNASISAPSPLVE
LILNHIVPPDDKRQNRSFEGMVAAALVAGRALQGLHLLELASNHFLYLPRDVLAQLPSL
RYLDLSNNSLVSLTYVSFRNLTHLESLHLEDNALKVLHNGTLAELQGLPHVRVFLDNNP
WVCDCHMADMVTWLKQTEVVQGKDRLTCAFPEKMRNRVLLELNSADLDCDPILPPSLQT
SYVFLGIVLALIGAIFLLVLYLNRKGIKKWMHNIRDACRDHMEGYHYRYEINADPRLTN
LSSNSDV (SEQ ID NO:86)

SEQUENCE LISTING

```
<160> NUMBER OF SEQ ID NOS: 99

<210> SEQ ID NO 1
<211> LENGTH: 414
<212> TYPE: DNA
<213> ORGANISM: Mus musculus
<220> FEATURE:
<221> NAME/KEY: misc_feature
<222> LOCATION: (1)..(57)
<223> OTHER INFORMATION: leader sequence
<220> FEATURE:
<221> NAME/KEY: misc_feature
<222> LOCATION: (58)..(414)
<223> OTHER INFORMATION: heavy chain variable region
<220> FEATURE:
<221> NAME/KEY: misc_difference
<222> LOCATION: (260)..(260)
<223> OTHER INFORMATION: n is g or t

<400> SEQUENCE: 1
atggattggc tgtggaactt gctattcctg atggcagctg cccaaagtat ccaagcacag      60
atccagttgg tgcagtctgg acctgagctg aagaagcctg gagagacagt caagatctcc     120
tgcaaggctt ctggatatac cttcacaaac tttggaatga actgggtgaa gcaggtccca     180
ggagagggtt taaagtggat gggctggata aacaccaaca ctggagagcc aagatatgct     240
gaagagttca agggacggtn tgcctttttct ttggaaacca ctgccagcac tgcctatttg     300
cagatcaaca acctcaaaaa tgaggacacg gctacatatt tctgtgcaag agactgggac     360
ggtgcctact tctttgacta ctggggccaa ggcaccactc tcacagtctc ctca           414

<210> SEQ ID NO 2
<211> LENGTH: 138
<212> TYPE: PRT
<213> ORGANISM: Mus musculus
<220> FEATURE:
<221> NAME/KEY: MISC_FEATURE
<222> LOCATION: (1)..(19)
<223> OTHER INFORMATION: leader sequence
<220> FEATURE:
<221> NAME/KEY: MISC_FEATURE
<222> LOCATION: (20)..(138)
<223> OTHER INFORMATION: heavy chain variable region
<220> FEATURE:
<221> NAME/KEY: MISC_FEATURE
<222> LOCATION: (45)..(54)
```

```
<223> OTHER INFORMATION: CDR1
<220> FEATURE:
<221> NAME/KEY: MISC_FEATURE
<222> LOCATION: (69)..(85)
<223> OTHER INFORMATION: CDR2
<220> FEATURE:
<221> NAME/KEY: MUTAGEN
<222> LOCATION: (87)..(87)
<223> OTHER INFORMATION: Xaa is cystein (C) or phenylalanine (F); this
      is position 67 with numbering according to Kabat
<220> FEATURE:
<221> NAME/KEY: MISC_FEATURE
<222> LOCATION: (118)..(127)
<223> OTHER INFORMATION: CDR3

<400> SEQUENCE: 2

Met Asp Trp Leu Trp Asn Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Phe Gly Met Asn Trp Val Lys Gln Gly Pro Gly Glu Gly Leu
    50                  55                  60

Lys Trp Met Gly Trp Ile Asn Thr Asn Thr Gly Glu Pro Arg Tyr Ala
65                  70                  75                  80

Glu Glu Phe Lys Gly Arg Xaa Ala Phe Ser Leu Glu Thr Thr Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Asp Trp Asp Gly Ala Tyr Phe Phe Asp Tyr Trp
        115                 120                 125

Gly Gln Gly Thr Thr Leu Thr Val Ser Ser
    130                 135

<210> SEQ ID NO 3
<211> LENGTH: 381
<212> TYPE: DNA
<213> ORGANISM: Mus musculus
<220> FEATURE:
<221> NAME/KEY: misc_feature
<222> LOCATION: (1)..(60)
<223> OTHER INFORMATION: leader sequence
<220> FEATURE:
<221> NAME/KEY: misc_feature
<222> LOCATION: (61)..(381)
<223> OTHER INFORMATION: light chain variable region

<400> SEQUENCE: 3
atgaagtcac agacccaggt cttcgtattt ctactgctct gtgtgtctgg tgctcatggg      60
agtattgtga tgacccagac tcccaaattc ctgcttgttt cagcaggaga cagggtgacc     120
ataacctgca aggccagtca gagtgtgagt aatgatgtag cttggtacca acagaagcca     180
gggcagtctc ctaaactgtt gataaacttt gcaaccaatc gctacactgg agtccctaat     240
cgcttcactg gcagtggata tgggacggat ttcactttca ccatcagcac tgtgcaggct     300
gaagacctgg cactttattt ctgtcagcag gattatagct ctccgtggac gttcggtgga     360
ggcaccaagc tggaaatcaa a                                               381

<210> SEQ ID NO 4
<211> LENGTH: 127
<212> TYPE: PRT
<213> ORGANISM: Mus musculus
<220> FEATURE:
```

```
<221> NAME/KEY: MISC_FEATURE
<222> LOCATION: (1)..(20)
<223> OTHER INFORMATION: leader sequence
<220> FEATURE:
<221> NAME/KEY: MISC_FEATURE
<222> LOCATION: (21)..(127)
<223> OTHER INFORMATION: light chain variable region
<220> FEATURE:
<221> NAME/KEY: MISC_FEATURE
<222> LOCATION: (44)..(54)
<223> OTHER INFORMATION: CDR1
<220> FEATURE:
<221> NAME/KEY: MISC_FEATURE
<222> LOCATION: (70)..(76)
<223> OTHER INFORMATION: CDR2
<220> FEATURE:
<221> NAME/KEY: MISC_FEATURE
<222> LOCATION: (109)..(117)
<223> OTHER INFORMATION: CDR3

<400> SEQUENCE: 4
```

Met Lys Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
            20                  25                  30

Val Ser Ala Gly Asp Arg Val Thr Ile Thr Cys Lys Ala Ser Gln Ser
        35                  40                  45

Val Ser Asn Asp Val Ala Trp Tyr Gln Gln Lys Pro Gly Gln Ser Pro
    50                  55                  60

Lys Leu Leu Ile Asn Phe Ala Thr Asn Arg Tyr Thr Gly Val Pro Asn
65              70                  75                  80

Arg Phe Thr Gly Ser Gly Tyr Gly Thr Asp Phe Thr Phe Thr Ile Ser
                85                  90                  95

Thr Val Gln Ala Glu Asp Leu Ala Leu Tyr Phe Cys Gln Gln Asp Tyr
            100                 105                 110

Ser Ser Pro Trp Thr Phe Gly Gly Thr Lys Leu Glu Ile Lys
        115                 120                 125

```
<210> SEQ ID NO 5
<211> LENGTH: 405
<212> TYPE: DNA
<213> ORGANISM: Mus musculus
<220> FEATURE:
<221> NAME/KEY: misc_feature
<222> LOCATION: (1)..(54)
<223> OTHER INFORMATION: leader sequence
<220> FEATURE:
<221> NAME/KEY: misc_feature
<222> LOCATION: (55)..(405)
<223> OTHER INFORMATION: heavy chain variable region

<400> SEQUENCE: 5
atggaatgga ggatctttct cttcatcctg tcaggaactg caggtgtcca ctcccaggtt    60
cagctgcagc agtctagacc tgagctggtg aagcctgggg cttcagtgaa gatgtcctgc   120
aaggcttctg gatacacttt cactgactat gttataagct gggtgaagca gagaactgga   180
cagggccttg agtggattgg agagatttat cctggaagta atagtattta ttacaatgag   240
aagttcaagg gcagggccac actgactgca gacaaatcct ccagcacagc ctacatgcag   300
ctcagcagcc tgacatctga ggactctgcg gtctatttct gtgcaatggg gggtaactac   360
ggctttgact attggggcca aggcaccact ctcacagtct cctca                   405

<210> SEQ ID NO 6
<211> LENGTH: 135
<212> TYPE: PRT
```

<213> ORGANISM: Mus musculus
<220> FEATURE:
<221> NAME/KEY: MISC_FEATURE
<222> LOCATION: (1)..(18)
<223> OTHER INFORMATION: leader sequence
<220> FEATURE:
<221> NAME/KEY: MISC_FEATURE
<222> LOCATION: (19)..(135)
<223> OTHER INFORMATION: heavy chain variable region
<220> FEATURE:
<221> NAME/KEY: MISC_FEATURE
<222> LOCATION: (44)..(53)
<223> OTHER INFORMATION: CDR1
<220> FEATURE:
<221> NAME/KEY: MISC_FEATURE
<222> LOCATION: (68)..(84)
<223> OTHER INFORMATION: CDR2
<220> FEATURE:
<221> NAME/KEY: MISC_FEATURE
<222> LOCATION: (117)..(124)
<223> OTHER INFORMATION: CDR3

<400> SEQUENCE: 6

```
Met Glu Trp Arg Ile Phe Leu Phe Ile Leu Ser Gly Thr Ala Gly Val
 1               5                  10                  15
His Ser Gln Val Gln Leu Gln Gln Ser Arg Pro Glu Leu Val Lys Pro
            20                  25                  30
Gly Ala Ser Val Lys Met Ser Cys Lys Ala Ser Gly Tyr Thr Phe Thr
        35                  40                  45
Asp Tyr Val Ile Ser Trp Val Lys Gln Arg Thr Gly Gln Gly Leu Glu
    50                  55                  60
Trp Ile Gly Glu Ile Tyr Pro Gly Ser Asn Ser Ile Tyr Tyr Asn Glu
65                  70                  75                  80
Lys Phe Lys Gly Arg Ala Thr Leu Thr Ala Asp Lys Ser Ser Ser Thr
                85                  90                  95
Ala Tyr Met Gln Leu Ser Ser Leu Thr Ser Glu Asp Ser Ala Val Tyr
            100                 105                 110
Phe Cys Ala Met Gly Gly Asn Tyr Gly Phe Asp Tyr Trp Gly Gln Gly
        115                 120                 125
Thr Thr Leu Thr Val Ser Ser
    130                 135
```

<210> SEQ ID NO 7
<211> LENGTH: 390
<212> TYPE: DNA
<213> ORGANISM: Mus musculus
<220> FEATURE:
<221> NAME/KEY: misc_feature
<222> LOCATION: (1)..(66)
<223> OTHER INFORMATION: leader sequence
<220> FEATURE:
<221> NAME/KEY: misc_feature
<222> LOCATION: (67)..(390)
<223> OTHER INFORMATION: light chain variable region

<400> SEQUENCE: 7

```
atggatttc aggtgcagat tttcagcttc ctgctaatca gtgcctcagt cataatgtcc    60
agaggacaaa ttgttctcac ccagtctcca gcaatcatgt ctgcatctct aggggaacgg   120
gtcaccttga cctgcactgc cagctcaagt gtaaattcca attacttaca ctggtaccag   180
cagaagccag atcctccccc caaactctgg atttatagca catccaacct ggcttctgga   240
gtcccagctc gcttcagtgg cagtgggtct gggacctctt actctctcac aatcagcagc   300
atggaggctg aagatgctgc cacttattac tgccaccagt atcatcgttc cccgctcacg   360
ttcggtgctg ggaccaagct ggagctgaaa                                    390
```

```
<210> SEQ ID NO 8
<211> LENGTH: 130
<212> TYPE: PRT
<213> ORGANISM: Mus musculus
<220> FEATURE:
<221> NAME/KEY: MISC_FEATURE
<222> LOCATION: (1)..(22)
<223> OTHER INFORMATION: leader sequence
<220> FEATURE:
<221> NAME/KEY: MISC_FEATURE
<222> LOCATION: (23)..(130)
<223> OTHER INFORMATION: light chain variable region
<220> FEATURE:
<221> NAME/KEY: MISC_FEATURE
<222> LOCATION: (46)..(56)
<223> OTHER INFORMATION: CDR1
<220> FEATURE:
<221> NAME/KEY: MISC_FEATURE
<222> LOCATION: (73)..(79)
<223> OTHER INFORMATION: CDR2
<220> FEATURE:
<221> NAME/KEY: MISC_FEATURE
<222> LOCATION: (112)..(120)
<223> OTHER INFORMATION: CDR3

<400> SEQUENCE: 8

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Arg Val Thr Leu Thr Cys Thr Ala Ser
        35                  40                  45

Ser Ser Val Asn Ser Asn Tyr Leu His Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr His Arg Ser Pro Leu Thr Phe Gly Ala Gly Thr Lys Leu Glu
        115                 120                 125

Leu Lys
    130

<210> SEQ ID NO 9
<211> LENGTH: 423
<212> TYPE: DNA
<213> ORGANISM: Mus musculus
<220> FEATURE:
<221> NAME/KEY: misc_feature
<222> LOCATION: (1)..(57)
<223> OTHER INFORMATION: leader sequence
<220> FEATURE:
<221> NAME/KEY: misc_feature
<222> LOCATION: (58)..(423)
<223> OTHER INFORMATION: heavy chain variable region
<220> FEATURE:
<221> NAME/KEY: misc_difference
<222> LOCATION: (347)..(347)
<223> OTHER INFORMATION: n is g or a

<400> SEQUENCE: 9
atgctgttgg ggctgaagtg ggttttcttt gttgtttttt atcaaggtgt gcattgtgag    60
gtgcagcttg ttgagtctgg tgaggattg gtgcagccta aagggtcatt gaaactctca   120
```

```
tgtgcagcct ctggattcac cttcaatacc tacgccatga actgggtccg ccaggctcca    180
ggaaagggtt tggaatgggt tgctcgcata agaagtaaaa gtaataatta tgcaacatat    240
tatgccgatt cagtgaaaga caggttcacc atctccagag atgattcaca aagcatgctc    300
tatctgcaaa tgaacaactt gaaaactgaa gacacagcca tgtattnctg tgtgagacag    360
tgggattacg acgtcagggc tatgaactac tggggtcaag aacctcagt caccgtctcc    420 tca                                                                 423
```

```
<210> SEQ ID NO 10
<211> LENGTH: 141
<212> TYPE: PRT
<213> ORGANISM: Mus musculus
<220> FEATURE:
<221> NAME/KEY: MISC_FEATURE
<222> LOCATION: (1)..(19)
<223> OTHER INFORMATION: leader sequence
<220> FEATURE:
<221> NAME/KEY: MISC_FEATURE
<222> LOCATION: (20)..(141)
<223> OTHER INFORMATION: heavy chain variable region
<220> FEATURE:
<221> NAME/KEY: MISC_FEATURE
<222> LOCATION: (45)..(54)
<223> OTHER INFORMATION: CDR1
<220> FEATURE:
<221> NAME/KEY: MISC_FEATURE
<222> LOCATION: (69)..(87)
<223> OTHER INFORMATION: CDR2
<220> FEATURE:
<221> NAME/KEY: MUTAGEN
<222> LOCATION: (116)..(116)
<223> OTHER INFORMATION: Xaa is cysteine (C) or tyrosine (Y); this is
      position 91 with numbering according to Kabat
<220> FEATURE:
<221> NAME/KEY: MISC_FEATURE
<222> LOCATION: (120)..(130)
<223> OTHER INFORMATION: CDR3

<400> SEQUENCE: 10

Met Leu Leu Gly Leu Lys Trp Val Phe Phe Val Val Phe Tyr Gln Gly
1               5                   10                  15

Val His Cys Glu Val Gln Leu Val Glu Ser Gly Gly Gly Leu Val Gln
            20                  25                  30

Pro Lys Gly Ser Leu Lys Leu Ser Cys Ala Ala Ser Gly Phe Thr Phe
        35                  40                  45

Asn Thr Tyr Ala Met Asn Trp Val Arg Gln Ala Pro Gly Lys Gly Leu
    50                  55                  60

Glu Trp Val Ala Arg Ile Arg Ser Lys Ser Asn Asn Tyr Ala Thr Tyr
65                  70                  75                  80

Tyr Ala Asp Ser Val Lys Asp Arg Phe Thr Ile Ser Arg Asp Asp Ser
                85                  90                  95

Gln Ser Met Leu Tyr Leu Gln Met Asn Asn Leu Lys Thr Glu Asp Thr
            100                 105                 110

Ala Met Tyr Xaa Cys Val Arg Gln Trp Asp Tyr Asp Val Arg Ala Met
        115                 120                 125

Asn Tyr Trp Gly Gln Gly Thr Ser Val Thr Val Ser Ser
    130                 135                 140

<210> SEQ ID NO 11
<211> LENGTH: 381
<212> TYPE: DNA
<213> ORGANISM: Mus musculus
<220> FEATURE:
<221> NAME/KEY: misc_feature
<222> LOCATION: (1)..(60)
```

```
<223> OTHER INFORMATION: leader sequence
<220> FEATURE:
<221> NAME/KEY: misc_feature
<222> LOCATION: (61)..(381)
<223> OTHER INFORMATION: light chain variable region

<400> SEQUENCE: 11
atggagacac attctcaggt ctttgtatac atgttgctgt ggttgtctgg tgttgaagga     60
gacattgtga tgacccagtc tcacatattc atgtccacat cagtaggaga cagggtcagc    120
atcacctgca aggccagtca ggatgtggat actgctgtag cctggtatca acagaaacca    180
gggcaatctc ctaaaactac tgatttactg gcatccaccc ggctcactgg agtccctgat    240
cgcttcacag gcagtggatc tgggacggat ttcactctca ccattagcaa tgtgcagtct    300
gaagacttgg cagattattt ctgtcagcaa tatagcagct atccgtacac gttcggaggg    360
gggaccaagc tggaaataaa a                                              381

<210> SEQ ID NO 12
<211> LENGTH: 127
<212> TYPE: PRT
<213> ORGANISM: Mus musculus
<220> FEATURE:
<221> NAME/KEY: MISC_FEATURE
<222> LOCATION: (1)..(20)
<223> OTHER INFORMATION: leader sequence
<220> FEATURE:
<221> NAME/KEY: MISC_FEATURE
<222> LOCATION: (21)..(127)
<223> OTHER INFORMATION: light chain variable region
<220> FEATURE:
<221> NAME/KEY: MISC_FEATURE
<222> LOCATION: (44)..(54)
<223> OTHER INFORMATION: CDR1
<220> FEATURE:
<221> NAME/KEY: MISC_FEATURE
<222> LOCATION: (70)..(76)
<223> OTHER INFORMATION: CDR2
<220> FEATURE:
<221> NAME/KEY: MISC_FEATURE
<222> LOCATION: (109)..(117)
<223> OTHER INFORMATION: CDR3

<400> SEQUENCE: 12

Met Glu Thr His Ser Gln Val Phe Val Tyr Met Leu Leu Trp Leu Ser
1               5                   10                  15

Gly Val Glu Gly Asp Ile Val Met Thr Gln Ser His Ile Phe Met Ser
                20                  25                  30

Thr Ser Val Gly Asp Arg Val Ser Ile Thr Cys Lys Ala Ser Gln Asp
            35                  40                  45

Val Asp Thr Ala Val Ala Trp Tyr Gln Gln Lys Pro Gly Gln Ser Pro
        50                  55                  60

Lys Leu Leu Ile Tyr Trp Ala Ser Thr Arg Leu Thr Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Asp Tyr Phe Cys Gln Gln Tyr Ser
            100                 105                 110

Ser Tyr Pro Tyr Thr Phe Gly Gly Gly Thr Lys Leu Glu Ile Lys
        115                 120                 125

<210> SEQ ID NO 13
<211> LENGTH: 98
<212> TYPE: PRT
<213> ORGANISM: Homo sapiens
```

-continued

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 14
<211> LENGTH: 98
<212> TYPE: PRT
<213> ORGANISM: Homo sapiens

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 15
<211> LENGTH: 98
<212> TYPE: PRT
<213> ORGANISM: Homo sapiens

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 16

```
<211> LENGTH: 98
<212> TYPE: PRT
<213> ORGANISM: Homo sapiens

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 17
<211> LENGTH: 98
<212> TYPE: PRT
<213> ORGANISM: Homo sapiens

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 18
<211> LENGTH: 98
<212> TYPE: PRT
<213> ORGANISM: Homo sapiens

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95
```

Ala Thr

<210> SEQ ID NO 19
<211> LENGTH: 98
<212> TYPE: PRT
<213> ORGANISM: Homo sapiens

<400> SEQUENCE: 19

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Tyr Arg
            20                  25                  30

Tyr Leu His Trp Val Arg Gln Ala Pro Gly Gln Ala Leu Glu Trp Met
        35                  40                  45

Gly Trp Ile Thr Pro Phe Asn Gly Asn Thr Asn Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg

<210> SEQ ID NO 20
<211> LENGTH: 98
<212> TYPE: PRT
<213> ORGANISM: Homo sapiens

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 21
<211> LENGTH: 98
<212> TYPE: PRT
<213> ORGANISM: Homo sapiens

<400> SEQUENCE: 21

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Ser Ser
            20                  25                  30

Ala Val Gln Trp Val Arg Gln Ala Arg Gly Gln Arg Leu Glu Trp Ile
        35                  40                  45

Gly Trp Ile Val Val Gly Ser Gly Asn Thr Asn Tyr Ala Gln Lys Phe
    50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Ala

<210> SEQ ID NO 22
<211> LENGTH: 98
<212> TYPE: PRT
<213> ORGANISM: Homo sapiens

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg

<210> SEQ ID NO 23
<211> LENGTH: 98
<212> TYPE: PRT
<213> ORGANISM: Homo sapiens

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg

<210> SEQ ID NO 24
<211> LENGTH: 98
<212> TYPE: PRT
<213> ORGANISM: Homo sapiens

<400> SEQUENCE: 24

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
            35                  40                  45

Gly Leu Val Asp Pro Glu Asp Gly Glu Thr Ile Tyr Ala Glu Lys Phe

```
                50                  55                  60
Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr

<210> SEQ ID NO 25
<211> LENGTH: 30
<212> TYPE: PRT
<213> ORGANISM: artificial
<220> FEATURE:
<223> OTHER INFORMATION: consensus sequence of human VH1 heavy chain
      variable region framework 1

<400> SEQUENCE: 25

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr
                20                  25                  30

<210> SEQ ID NO 26
<211> LENGTH: 14
<212> TYPE: PRT
<213> ORGANISM: Artificial
<220> FEATURE:
<223> OTHER INFORMATION: consensus sequence of human VH1 heavy chain
      variable region framework 2

<400> SEQUENCE: 26

Trp Val Arg Gln Ala Pro Gly Gln Gly Leu Glu Trp Met Gly
 1               5                  10

<210> SEQ ID NO 27
<211> LENGTH: 32
<212> TYPE: PRT
<213> ORGANISM: Artificial
<220> FEATURE:
<223> OTHER INFORMATION: consensus sequence of human VH1 heavy chain
      variable region framework 3

<400> SEQUENCE: 27

Arg Val Thr Ile Thr Arg Asp Thr Ser Thr Ser Thr Ala Tyr Met Glu
 1               5                  10                  15

Leu Ser Ser Leu Arg Ser Glu Asp Thr Ala Val Tyr Tyr Cys Ala Arg
                20                  25                  30

<210> SEQ ID NO 28
<211> LENGTH: 101
<212> TYPE: PRT
<213> ORGANISM: Homo sapiens

<400> SEQUENCE: 28

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Arg Glu Ser Gly Val
        50                  55                  60

Pro Asp Arg Phe Ser Gly Ser Gly Ser Gly Thr Asp Phe Thr Leu Thr
 65                  70                  75                  80
```

```
Ile Ser Ser Leu Gln Ala Glu Asp Val Ala Val Tyr Tyr Cys Gln Gln
                85                  90                  95

Tyr Tyr Ser Thr Pro
            100

<210> SEQ ID NO 29
<211> LENGTH: 98
<212> TYPE: PRT
<213> ORGANISM: Homo sapiens

<400> SEQUENCE: 29

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Thr Val

<210> SEQ ID NO 30
<211> LENGTH: 98
<212> TYPE: PRT
<213> ORGANISM: Homo sapiens

<400> SEQUENCE: 30

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Thr Val

<210> SEQ ID NO 31
<211> LENGTH: 96
<212> TYPE: PRT
<213> ORGANISM: Homo sapiens

<400> SEQUENCE: 31

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45
```

```
Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

<210> SEQ ID NO 32
<211> LENGTH: 95
<212> TYPE: PRT
<213> ORGANISM: Homo sapiens

<400> SEQUENCE: 32

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95
```

<210> SEQ ID NO 33
<211> LENGTH: 96
<212> TYPE: PRT
<213> ORGANISM: Homo sapiens

<400> SEQUENCE: 33

```
Glu Ile Val Met Thr Gln Ser Pro Pro Thr Leu Ser Leu Ser Pro Gly
1               5                   10                  15

Glu Arg Val Thr Leu Ser Cys Arg Ala Ser Gln Ser Val Ser Ser Ser
                20                  25                  30

Tyr Leu Thr Trp Tyr Gln Gln Lys Pro Gly Gln Ala Pro Arg Leu Leu
            35                  40                  45

Ile Tyr Gly Ala Ser Thr Arg Ala Thr Ser Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp His Asn Leu Pro
                85                  90                  95
```

<210> SEQ ID NO 34
<211> LENGTH: 96
<212> TYPE: PRT
<213> ORGANISM: Homo sapiens

<400> SEQUENCE: 34

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ser Trp Tyr Gln Gln Lys Pro Gly Gln Ala Pro Arg Leu Leu
            35                  40                  45

Ile Tyr Gly Ala Ser Thr Arg Ala Thr Gly Ile Pro Ala Arg Phe Ser
    50                  55                  60
```

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

<210> SEQ ID NO 35
<211> LENGTH: 95
<212> TYPE: PRT
<213> ORGANISM: Homo sapiens

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 36
<211> LENGTH: 95
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 37
<211> LENGTH: 95
<212> TYPE: PRT
<213> ORGANISM: Homo sapiens

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro

```
            65                  70                  75                  80

Glu Asp Ile Ala Thr Tyr Tyr Cys Gln Gln Tyr Asp Asn Leu Pro
                    85                  90                  95

<210> SEQ ID NO 38
<211> LENGTH: 95
<212> TYPE: PRT
<213> ORGANISM: Homo sapiens

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95

<210> SEQ ID NO 39
<211> LENGTH: 95
<212> TYPE: PRT
<213> ORGANISM: Homo sapiens

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro
                85                  90                  95

<210> SEQ ID NO 40
<211> LENGTH: 95
<212> TYPE: PRT
<213> ORGANISM: Homo sapiens

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Asn Ser Tyr Pro
                85                  90                  95
```

<210> SEQ ID NO 41
<211> LENGTH: 95
<212> TYPE: PRT
<213> ORGANISM: Homo sapiens

<400> SEQUENCE: 41

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95
```

<210> SEQ ID NO 42
<211> LENGTH: 95
<212> TYPE: PRT
<213> ORGANISM: Homo sapiens

<400> SEQUENCE: 42

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro
                85                  90                  95
```

<210> SEQ ID NO 43
<211> LENGTH: 95
<212> TYPE: PRT
<213> ORGANISM: Homo sapiens

<400> SEQUENCE: 43

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95
```

```
<210> SEQ ID NO 44
<211> LENGTH: 95
<212> TYPE: PRT
<213> ORGANISM: Homo sapiens

<400> SEQUENCE: 44

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Ser
                85                  90                  95

<210> SEQ ID NO 45
<211> LENGTH: 327
<212> TYPE: PRT
<213> ORGANISM: Homo sapiens

<400> SEQUENCE: 45

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240
```

```
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 46
<211> LENGTH: 330
<212> TYPE: PRT
<213> ORGANISM: Homo sapiens

<400> SEQUENCE: 46

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 47
<211> LENGTH: 330
<212> TYPE: PRT
<213> ORGANISM: Homo sapiens

<400> SEQUENCE: 47

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 48
<211> LENGTH: 357
<212> TYPE: DNA
<213> ORGANISM: Artificial
<220> FEATURE:
<223> OTHER INFORMATION: derived from human and mouse sequences

<400> SEQUENCE: 48
caggtgcagc tggtgcaatc tgggtctgag ttgaagaagc ctggggcctc agtgaaggtt      60
tcctgcaagg cttctggata taccttcaca aactttggaa tgaactgggt gcgacaggcc     120
cctggacaag gcttaagtg gatgggatgg ataaacacca acactggaga gccaagatat      180
gctgaagagt tcaagggacg gtttgtcttc tccttggaca cctctgtcag cactgcctat     240
ctgcagatct ccagcctgaa ggctgaggac actgccgtgt attactgtgc cagagactgg     300
gacggtgcct acttctttga ctactggggc caaggcaccc ttgtcacagt ctcctca       357

<210> SEQ ID NO 49
<211> LENGTH: 119
<212> TYPE: PRT
<213> ORGANISM: Artificial
<220> FEATURE:
<223> OTHER INFORMATION: derived from human and mouse sequences
<220> FEATURE:
<221> NAME/KEY: MISC_FEATURE
<222> LOCATION: (23)..(35)
<223> OTHER INFORMATION: CDR1
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (99)..(108)
<223> OTHER INFORMATION: CDR3

<400> SEQUENCE: 49

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Phe
            20                  25                  30

Gly Met Asn Trp Val Arg Gln Ala Pro Gly Gln Gly Leu Lys Trp Met
        35                  40                  45

Gly Trp Ile Asn Thr Asn Thr Gly Glu Pro Arg Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
            85                  90                  95

Ala Arg Asp Trp Asp Gly Ala Tyr Phe Phe Asp Tyr Trp Gly Gln Gly
        100                 105                 110

Thr Leu Val Thr Val Ser Ser
        115

<210> SEQ ID NO 50
<211> LENGTH: 357
<212> TYPE: DNA
<213> ORGANISM: Artificial
<220> FEATURE:
<223> OTHER INFORMATION: derived from human and mouse sequences

<400> SEQUENCE: 50
caggtgcagc tggtgcaatc tgggtctgag ttgaagaagc ctggggcctc agtgaaggtt      60
```

```
tcctgcaagg cttctggata taccttcaca aactttggaa tgaactgggt gcgacaggcc      120
cctggacaag ggcttgagtg gatgggatgg ataaacacca acactggaga gccaagatat      180
gctgaagagt tcaagggacg gtttgtcttc tccttggaca cctctgtcag cactgcctat      240
ctgcagatct ccagcctgaa ggctgaggac actgccgtgt attactgtgc cagagactgg      300
gacggtgcct acttctttga ctactggggc caaggcaccc ttgtcacagt ctcctca       357
```

<210> SEQ ID NO 51
<211> LENGTH: 119
<212> TYPE: PRT
<213> ORGANISM: Artificial
<220> FEATURE:
<223> OTHER INFORMATION: derived from human and mouse sequences

<400> SEQUENCE: 51

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Phe
            20                  25                  30

Gly Met Asn Trp Val Arg Gln Ala Pro Gly Gln Gly Leu Glu Trp Met
        35                  40                  45

Gly Trp Ile Asn Thr Asn Thr Gly Glu Pro Arg Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Trp Asp Gly Ala Tyr Phe Phe Asp Tyr Trp Gly Gln Gly
            100                 105                 110

Thr Leu Val Thr Val Ser Ser
        115

<210> SEQ ID NO 52
<211> LENGTH: 119
<212> TYPE: PRT
<213> ORGANISM: Artificial
<220> FEATURE:
<223> OTHER INFORMATION: derived from human and mouse sequences

<400> SEQUENCE: 52

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Phe
            20                  25                  30

Gly Met Asn Trp Val Arg Gln Ala Pro Gly Gln Gly Leu Glu Trp Met
        35                  40                  45

Gly Trp Ile Asn Thr Asn Thr Gly Glu Pro Arg Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Asp Trp Asp Gly Ala Tyr Phe Phe Asp Tyr Trp Gly Gln Gly
            100                 105                 110

Thr Leu Val Thr Val Ser Ser
        115

<210> SEQ ID NO 53

<211> LENGTH: 357
<212> TYPE: DNA
<213> ORGANISM: Artificial
<220> FEATURE:
<223> OTHER INFORMATION: derived from human and mouse sequences

<400> SEQUENCE: 53

```
gaggtgcagc tggtggagtc tgggggaggc ttggtccagc ctgggggtc cctgagactc      60
tcctgtgcag cctctggata taccttcaca aactttggaa tgaactgggt ccgccaggct    120
ccagggaagg ggctggagtg ggtggcctgg ataaacacca acaccggtga gccaagatat    180
gctgaaagt tcaagggacg attcaccatc tccagagaca cgccaagaa ctcactgtat     240
ctgcaaatga acagcctgag agccgaggac accgctgtgt attactgtgc cagagactgg    300
gacggtgcct acttctttga ctactggggc caaggcaccc ttgtcacagt ctcctca      357
```

<210> SEQ ID NO 54
<211> LENGTH: 119
<212> TYPE: PRT
<213> ORGANISM: Artificial
<220> FEATURE:
<223> OTHER INFORMATION: derived from human and mouse sequences

<400> SEQUENCE: 54

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Thr Asn Phe
            20                  25                  30
Gly Met Asn Trp Val Arg Gln Ala Pro Gly Lys Gly Leu Glu Trp Val
        35                  40                  45
Ala Trp Ile Asn Thr Asn Thr Gly Glu Pro Arg Tyr Ala Glu Glu Phe
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Asp Trp Asp Gly Ala Tyr Phe Phe Asp Tyr Trp Gly Gln Gly
            100                 105                 110
Thr Leu Val Thr Val Ser Ser
        115
```

<210> SEQ ID NO 55
<211> LENGTH: 357
<212> TYPE: DNA
<213> ORGANISM: Artificial
<220> FEATURE:
<223> OTHER INFORMATION: derived from human and mouse sequences

<400> SEQUENCE: 55

```
gaggtgcagc tggtggagtc tgggggaggc ttggtccagc ctgggggtc cctgagactc      60
tcctgtgcag cctctggata taccttcaca aactttggaa tgaactgggt ccgccaggct    120
ccagggaagg ggctgaagtg gatgggctgg ataaacacca acaccggtga gccaagatat    180
gctgaaagt tcaagggacg attcaccatc tccctggaca cgccaagtc ctcagcctat     240
ctgcaaatga acagcctgag agccgaggac accgctgtgt attactgtgc cagagactgg    300
gacggtgcct acttctttga ctactggggc caaggcaccc ttgtcacagt ctcctca      357
```

<210> SEQ ID NO 56
<211> LENGTH: 119
<212> TYPE: PRT

<213> ORGANISM: Artificial
<220> FEATURE:
<223> OTHER INFORMATION: derived from human and mouse sequences

<400> SEQUENCE: 56

| Glu | Val | Gln | Leu | Val | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Arg | Leu | Ser | Cys | Ala | Ala | Ser | Gly | Tyr | Thr | Phe | Thr | Asn | Phe |
|     |     |     | 20  |     |     |     |     | 25  |     |     |     |     | 30  |     |     |

| Gly | Met | Asn | Trp | Val | Arg | Gln | Ala | Pro | Gly | Lys | Gly | Leu | Lys | Trp | Met |
|     |     | 35  |     |     |     |     | 40  |     |     |     |     | 45  |     |     |     |

| Gly | Trp | Ile | Asn | Thr | Asn | Thr | Gly | Glu | Pro | Arg | Tyr | Ala | Glu | Glu | Phe |
|     | 50  |     |     |     |     | 55  |     |     |     |     | 60  |     |     |     |     |

| Lys | Gly | Arg | Phe | Thr | Ile | Ser | Leu | Asp | Asn | Ala | Lys | Ser | Ser | Ala | Tyr |
| 65  |     |     |     |     | 70  |     |     |     |     | 75  |     |     |     |     | 80  |

| Leu | Gln | Met | Asn | Ser | Leu | Arg | Ala | Glu | Asp | Thr | Ala | Val | Tyr | Tyr | Cys |
|     |     |     |     | 85  |     |     |     |     | 90  |     |     |     |     | 95  |     |

| Ala | Arg | Asp | Trp | Asp | Gly | Ala | Tyr | Phe | Phe | Asp | Tyr | Trp | Gly | Gln | Gly |
|     |     |     | 100 |     |     |     |     | 105 |     |     |     |     | 110 |     |     |

| Thr | Leu | Val | Thr | Val | Ser | Ser |
|     |     |     |     | 115 |     |     |

<210> SEQ ID NO 57
<211> LENGTH: 321
<212> TYPE: DNA
<213> ORGANISM: Artificial
<220> FEATURE:
<223> OTHER INFORMATION: derived from human and mouse sequences

<400> SEQUENCE: 57

| gacatcgtga tgacccagtc tccagactcc ctggctgtgt ctctgggcga gagggccacc | 60 |
| atcaactgca aggccagtca gagtgtgagt aatgatgtgg cttggtacca gcagaaacca | 120 |
| ggacagcctc ctaagctgct catttacttt gcaaccaatc gctacactgg agtccctgac | 180 |
| cgcttctccg gcagcggatc cggcacagat ttcactctca ccatcagcag cctgcaggct | 240 |
| gaagatgtgg cagtttatta ctgtcagcag gattatagct ccctggac cttcggtcag | 300 |
| ggcaccaagg tggaaatcaa a | 321 |

<210> SEQ ID NO 58
<211> LENGTH: 107
<212> TYPE: PRT
<213> ORGANISM: Artificial
<220> FEATURE:
<223> OTHER INFORMATION: derived from human and mouse sequences

<400> SEQUENCE: 58

| Asp | Ile | Val | Met | Thr | Gln | Ser | Pro | Asp | Ser | Leu | Ala | Val | Ser | Leu | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Glu | Arg | Ala | Thr | Ile | Asn | Cys | Lys | Ala | Ser | Gln | Ser | Val | Ser | Asn | Asp |
|     |     |     | 20  |     |     |     |     | 25  |     |     |     |     | 30  |     |     |

| Val | Ala | Trp | Tyr | Gln | Gln | Lys | Pro | Gly | Gln | Pro | Pro | Lys | Leu | Leu | Ile |
|     |     |     | 35  |     |     |     |     | 40  |     |     |     |     | 45  |     |     |

| Tyr | Phe | Ala | Thr | Asn | Arg | Tyr | Thr | Gly | Val | Pro | Asp | Arg | Phe | Ser | Gly |
|     | 50  |     |     |     |     | 55  |     |     |     |     | 60  |     |     |     |     |

| Ser | Gly | Ser | Gly | Thr | Asp | Phe | Thr | Leu | Thr | Ile | Ser | Ser | Leu | Gln | Ala |
| 65  |     |     |     |     | 70  |     |     |     |     | 75  |     |     |     |     | 80  |

| Glu | Asp | Val | Ala | Val | Tyr | Tyr | Cys | Gln | Gln | Asp | Tyr | Ser | Ser | Pro | Trp |
|     |     |     |     | 85  |     |     |     |     | 90  |     |     |     |     | 95  |     |

Thr Phe Gly Gln Gly Thr Lys Val Glu Ile Lys
            100                 105

<210> SEQ ID NO 59
<211> LENGTH: 321
<212> TYPE: PRT
<213> ORGANISM: Artificial
<220> FEATURE:
<223> OTHER INFORMATION: derived from human and mouse sequences

<400> SEQUENCE: 59

Gly Ala Cys Ala Thr Cys Gly Thr Gly Ala Thr Gly Ala Cys Cys Cys
1               5                   10                  15

Ala Gly Thr Cys Thr Cys Cys Ala Gly Ala Cys Thr Cys Cys Cys Thr
            20                  25                  30

Gly Gly Cys Thr Gly Thr Gly Thr Cys Thr Gly Gly Gly Cys
            35                  40                  45

Gly Ala Gly Ala Gly Gly Cys Cys Ala Cys Cys Ala Thr Cys Ala
        50                  55                  60

Ala Cys Thr Gly Cys Ala Ala Gly Gly Cys Cys Ala Gly Thr Cys Ala
65                  70                  75                  80

Gly Ala Gly Thr Gly Thr Gly Ala Gly Thr Ala Ala Thr Gly Ala Thr
            85                  90                  95

Gly Thr Gly Gly Cys Thr Thr Gly Gly Thr Ala Cys Cys Ala Gly Cys
            100                 105                 110

Ala Gly Ala Ala Cys Cys Ala Gly Gly Ala Cys Ala Gly Cys Cys
            115                 120                 125

Thr Cys Cys Thr Ala Ala Gly Cys Thr Gly Cys Thr Cys Ala Thr Thr
130                 135                 140

Thr Ala Cys Thr Thr Thr Gly Cys Ala Ala Cys Cys Ala Ala Thr Cys
145                 150                 155                 160

Gly Cys Thr Ala Cys Ala Cys Thr Gly Gly Ala Gly Thr Cys Cys Cys
            165                 170                 175

Thr Gly Ala Cys Cys Gly Cys Thr Thr Cys Thr Cys Cys Gly Gly Cys
            180                 185                 190

Ala Gly Cys Gly Gly Ala Thr Ala Cys Gly Gly Cys Ala Cys Ala Gly
            195                 200                 205

Ala Thr Thr Thr Cys Ala Cys Thr Cys Thr Cys Ala Cys Cys Ala Thr
            210                 215                 220

Cys Ala Gly Cys Ala Gly Cys Cys Thr Gly Cys Ala Gly Gly Cys Thr
225                 230                 235                 240

Gly Ala Ala Gly Ala Thr Gly Thr Gly Gly Cys Ala Gly Thr Thr Thr
            245                 250                 255

Ala Thr Thr Ala Cys Thr Gly Cys Ala Gly Cys Ala Gly Gly Ala
            260                 265                 270

Thr Thr Ala Thr Ala Gly Cys Thr Cys Thr Cys Cys Thr Gly Gly
            275                 280                 285

Ala Cys Cys Thr Thr Cys Gly Gly Thr Cys Ala Gly Gly Cys
            290                 295                 300

Cys Cys Ala Ala Gly Gly Thr Gly Gly Ala Ala Ala Thr Cys Ala Ala
305                 310                 315                 320

Ala

<210> SEQ ID NO 60
<211> LENGTH: 107
<212> TYPE: PRT
<213> ORGANISM: Artificial

```
<220> FEATURE:
<223> OTHER INFORMATION: derived from human and mouse sequences

<400> SEQUENCE: 60

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
            20                  25                  30

Val Ala Trp Tyr Gln Gln Lys Pro Gly Gln Pro Pro Lys Leu Leu Ile
        35                  40                  45

Tyr Phe Ala Thr Asn Arg Tyr Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys Gln Gln Asp Tyr Ser Ser Pro Trp
                85                  90                  95

Thr Phe Gly Gln Gly Thr Lys Val Glu Ile Lys
            100                 105

<210> SEQ ID NO 61
<211> LENGTH: 321
<212> TYPE: DNA
<213> ORGANISM: Artificial
<220> FEATURE:
<223> OTHER INFORMATION: derived from human and mouse sequences

<400> SEQUENCE: 61
gacatccaga tgacccagtc tccatcctcc ctgtctgcat ctgtcggaga cagagtcacc        60
atcacttgca aggccagtca gagtgtgagt aatgatgtgg cttggtatca gcagaaacca       120
ggcaaagccc ctaagctcct gatctatttt gcaaccaatc gctacactgg agtcccatcc       180
cgcttcagcg gcagcggatc cggcacagat ttcactctca ccatcagcag cctgcaacct       240
gaagattttg caacttacta ctgtcagcag gattatagct ccctggac cttcggtcag         300 ggcaccaagg tggaaatcaa a                                                 321

<210> SEQ ID NO 62
<211> LENGTH: 107
<212> TYPE: PRT
<213> ORGANISM: Artificial
<220> FEATURE:
<223> OTHER INFORMATION: derived from human and mouse sequences

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Phe Ala Thr Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Trp
                85                  90                  95

Thr Phe Gly Gln Gly Thr Lys Val Glu Ile Lys
            100                 105
```

```
<210> SEQ ID NO 63
<211> LENGTH: 321
<212> TYPE: DNA
<213> ORGANISM: Artificial
<220> FEATURE:
<223> OTHER INFORMATION: derived from human and mouse sequences

<400> SEQUENCE: 63
gacatccaga tgacccagtc tccatcctcc ctgtctgcat ctgtcggaga cagagtcacc      60
atcacttgca aggccagtca gagtgtgagt aatgatgtgg cttggtatca gcagaaacca     120
ggcaaatccc ctaagctcct gatctatttt gcaaccaatc gctacactgg agtcccatcc     180
cgcttcagcg gcagcggatc cggcacagat ttcactctca ccatcagcag cctgcaacct     240
gaagattttg caacttacta ctgtcagcag gattatagct ctccctggac cttcggtcag     300
ggcaccaagg tggaaatcaa a                                               321

<210> SEQ ID NO 64
<211> LENGTH: 107
<212> TYPE: PRT
<213> ORGANISM: Artificial
<220> FEATURE:
<223> OTHER INFORMATION: derived from human and mouse sequences

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ser Pro Lys Leu Leu Ile
        35                  40                  45

Tyr Phe Ala Thr Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Trp
                85                  90                  95

Thr Phe Gly Gln Gly Thr Lys Val Glu Ile Lys
            100                 105

<210> SEQ ID NO 65
<211> LENGTH: 321
<212> TYPE: DNA
<213> ORGANISM: Artificial
<220> FEATURE:
<223> OTHER INFORMATION: derived from human and mouse sequences

<400> SEQUENCE: 65
gacatccaga tgacccagtc tccatcctcc ctgtctgcat ctgtcggaga cagagtcacc      60
atcacttgca aggccagtca gagtgtgagt aatgatgtgg cttggtatca gcagaaacca     120
ggcaaagccc ctaagctcct gatcaatttt gcaaccaatc gctacactgg agtcccatcc     180
cgcttcagcg gcagcggatc cggcacagat ttcactctca ccatcagcag cctgcaacct     240
gaagattttg caacttacta ctgtcagcag gattatagct ctccctggac cttcggtcag     300
ggcaccaagg tggaaatcaa a                                               321

<210> SEQ ID NO 66
<211> LENGTH: 107
<212> TYPE: PRT
<213> ORGANISM: Artificial
<220> FEATURE:
```

<223> OTHER INFORMATION: derived from human and mouse sequences

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Asn Phe Ala Thr Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Trp
                85                  90                  95

Thr Phe Gly Gln Gly Thr Lys Val Glu Ile Lys
            100                 105

<210> SEQ ID NO 67
<211> LENGTH: 321
<212> TYPE: DNA
<213> ORGANISM: Artificial
<220> FEATURE:
<223> OTHER INFORMATION: derived from human and mouse sequences

<400> SEQUENCE: 67
gacatccaga tgacccagtc tccatcctcc ctgtctgcat ctgtcggaga cagagtcacc      60
atcacttgca aggccagtca gagtgtgagt aatgatgtgg cttggtatca gcagaaacca     120
ggcaaagccc ctaagctcct gatctatttt gcaaccaatc gctacactgg agtcccaaac    180
cgcttcagcg gcagcggatc cggcacagat ttcactctca ccatcagcag cctgcaacct    240
gaagattttg caacttacta ctgtcagcag gattatagct ccctggac cttcggtcag      300
ggcaccaagg tggaaatcaa a                                               321

<210> SEQ ID NO 68
<211> LENGTH: 107
<212> TYPE: PRT
<213> ORGANISM: Artificial
<220> FEATURE:
<223> OTHER INFORMATION: derived from human and mouse sequences

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Phe Ala Thr Asn Arg Tyr Thr Gly Val Pro Asn Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Trp
                85                  90                  95

Thr Phe Gly Gln Gly Thr Lys Val Glu Ile Lys
            100                 105

<210> SEQ ID NO 69

<211> LENGTH: 321
<212> TYPE: DNA
<213> ORGANISM: Artificial
<220> FEATURE:
<223> OTHER INFORMATION: derived from human and mouse sequences

<400> SEQUENCE: 69

```
gacatccaga tgacccagtc tccatcctcc ctgtctgcat ctgtcggaga cagagtcacc    60
atcacttgca aggccagtca gagtgtgagt aatgatgtgg cttggtatca gcagaaacca   120
ggcaaagccc ctaagctcct gatctatttt gcaaccaatc gctacactgg agtcccatcc   180
cgcttcagcg gcagcggata cggcacagat ttcactctca ccatcagcag cctgcaacct   240
gaagattttg caacttacta ctgtcagcag gattatagct ctccctggac cttcggtcag   300
ggcaccaagg tggaaatcaa a                                             321
```

<210> SEQ ID NO 70
<211> LENGTH: 107
<212> TYPE: PRT
<213> ORGANISM: Artificial
<220> FEATURE:
<223> OTHER INFORMATION: derived from human and mouse sequences

<400> SEQUENCE: 70

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Phe Ala Thr Asn Arg Tyr Thr Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Trp
                85                  90                  95

Thr Phe Gly Gln Gly Thr Lys Val Glu Ile Lys
            100                 105
```

<210> SEQ ID NO 71
<211> LENGTH: 321
<212> TYPE: DNA
<213> ORGANISM: Artificial
<220> FEATURE:
<223> OTHER INFORMATION: derived from human and mouse sequences

<400> SEQUENCE: 71

```
gacatccaga tgacccagtc tccatcctcc ctgtctgcat ctgtcggaga cagagtcacc    60
atcacttgca aggccagtca gagtgtgagt aatgatgtgg cttggtatca gcagaaacca   120
ggcaaagccc ctaagctcct gatctatttt gcaaccaatc gctacactgg agtcccatcc   180
cgcttcagcg gcagcggatc cggcacagat ttcactttca ccatcagcag cctgcaacct   240
gaagattttg caacttacta ctgtcagcag gattatagct ctccctggac cttcggtcag   300
ggcaccaagg tggaaatcaa a                                             321
```

<210> SEQ ID NO 72
<211> LENGTH: 107
<212> TYPE: PRT
<213> ORGANISM: Artificial
<220> FEATURE:
<223> OTHER INFORMATION: derived from human and mouse sequences

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Phe Ala Thr Asn Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Asp Tyr Ser Ser Pro Trp
                85                  90                  95

Thr Phe Gly Gln Gly Thr Lys Val Glu Ile Lys
            100                 105

<210> SEQ ID NO 73
<211> LENGTH: 321
<212> TYPE: DNA
<213> ORGANISM: Artificial
<220> FEATURE:
<223> OTHER INFORMATION: derived from human and mouse sequences

<400> SEQUENCE: 73

```
gaaattgtga tgacacagtc tccagccacc ctgtccctgt ctccaggcga aagagccacc    60
ctctcctgca aggccagtca gagtgtgagt aatgatgtgg cttggtacca gcagaaacct   120
gggcaggctc ccaggctgct gatctatttt gcaaccaatc gctacactgg catcccagcc   180
cgcttctccg gcagcggctc cggcacagac ttcactctca ccatcagcag cctgcagcct   240
gaagattttg cagtttatta ctgtcagcag gattatagct ctccctggac cttcggtcag   300
ggcaccaagg tggaaatcaa a                                             321
```

<210> SEQ ID NO 74
<211> LENGTH: 107
<212> TYPE: PRT
<213> ORGANISM: Artificial
<220> FEATURE:
<223> OTHER INFORMATION: derived from human and mouse sequences

<400> SEQUENCE: 74

Glu Ile Val Met Thr Gln Ser Pro Ala Thr Leu Ser Leu Ser Pro Gly
1               5                   10                  15

Glu Arg Ala Thr Leu Ser Cys Lys Ala Ser Gln Ser Val Ser Asn Asp
            20                  25                  30

Val Ala Trp Tyr Gln Gln Lys Pro Gly Gln Ala Pro Arg Leu Leu Ile
        35                  40                  45

Tyr Phe Ala Thr Asn Arg Tyr Thr Gly Ile Pro Ala Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Asp Tyr Ser Ser Pro Trp
                85                  90                  95

Thr Phe Gly Gln Gly Thr Lys Val Glu Ile Lys
            100                 105

<210> SEQ ID NO 75
<211> LENGTH: 321

```
<212> TYPE: DNA
<213> ORGANISM: Artificial
<220> FEATURE:
<223> OTHER INFORMATION: derived from human and mouse sequences

<400> SEQUENCE: 75
gaaattgtga tgacacagtc tccagccacc ctgtccctgt ctccaggcga aagagccacc      60
ctctcctgca aggccagtca gagtgtgagt aatgatgtgg cttggtacca gcagaaacct     120
gggcaggctc ccaggctgct gatctatttt gcaaccaatc gctacactgg catcccagcc    180
cgcttctccg gcagcggcta cggcacagac ttcactctca ccatcagcag cctgcagcct    240
gaagattttg cagtttatta ctgtcagcag gattatagct ctccctggac cttcggtcag    300
ggcaccaagg tggaaatcaa a                                               321

<210> SEQ ID NO 76
<211> LENGTH: 107
<212> TYPE: PRT
<213> ORGANISM: Artificial
<220> FEATURE:
<223> OTHER INFORMATION: derived from human and mouse sequences

<400> SEQUENCE: 76

Glu Ile Val Met Thr Gln Ser Pro Ala Thr Leu Ser Leu Ser Pro Gly
1               5                   10                  15

Glu Arg Ala Thr Leu Ser Cys Lys Ala Ser Gln Ser Val Ser Asn Asp
            20                  25                  30

Val Ala Trp Tyr Gln Gln Lys Pro Gly Gln Ala Pro Arg Leu Leu Ile
        35                  40                  45

Tyr Phe Ala Thr Asn Arg Tyr Thr Gly Ile Pro Ala Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Val Tyr Tyr Cys Gln Gln Asp Tyr Ser Ser Pro Trp
                85                  90                  95

Thr Phe Gly Gln Gly Thr Lys Val Glu Ile Lys
            100                 105

<210> SEQ ID NO 77
<211> LENGTH: 117
<212> TYPE: PRT
<213> ORGANISM: Artificial
<220> FEATURE:
<223> OTHER INFORMATION: derived from human and mouse sequences

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Ile Ser Trp Val Arg Gln Ala Pro Gly Gln Gly Leu Glu Trp Met
        35                  40                  45

Gly Glu Ile Tyr Pro Gly Ser Asn Ser Ile Tyr Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Asn Tyr Gly Phe Asp Tyr Trp Gly Gln Gly Thr Leu
            100                 105                 110
```

Val Thr Val Ser Ser
        115

<210> SEQ ID NO 78
<211> LENGTH: 117
<212> TYPE: PRT
<213> ORGANISM: Artificial
<220> FEATURE:
<223> OTHER INFORMATION: derived from human and mouse sequences

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Val Ile Ser Trp Val Arg Gln Ala Pro Gly Lys Gly Leu Glu Trp Val
        35                  40                  45

Ala Glu Ile Tyr Pro Gly Ser Asn Ser Ile Tyr Tyr Asn Glu Lys Phe
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asn Tyr Gly Phe Asp Tyr Trp Gly Gln Gly Thr Leu
            100                 105                 110

Val Thr Val Ser Ser
        115

<210> SEQ ID NO 79
<211> LENGTH: 108
<212> TYPE: PRT
<213> ORGANISM: Artificial
<220> FEATURE:
<223> OTHER INFORMATION: derived from human and mouse sequences

<400> SEQUENCE: 79

Glu Ile Val Leu Thr Gln Ser Pro Ala Thr Leu Ser Leu Ser Pro Gly
1               5                   10                  15

Glu Arg Ala Thr Leu Ser Cys Thr Ala Ser Ser Ser Val Asn Ser Asn
            20                  25                  30

Tyr Leu His Trp Tyr Gln Gln Lys Pro Gly Leu Ala Pro Arg Leu Leu
        35                  40                  45

Ile Tyr Ser Thr Ser Asn Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr His Arg Ser Pro
                85                  90                  95

Leu Thr Phe Gly Gly Gly Thr Lys Val Glu Ile Lys
            100                 105

<210> SEQ ID NO 80
<211> LENGTH: 108
<212> TYPE: PRT
<213> ORGANISM: Artificial
<220> FEATURE:
<223> OTHER INFORMATION: derived from human and mouse sequences

<400> SEQUENCE: 80

Asp Ile Gln Met Thr Gln Ser Pro Ser Ser Leu Ser Ala Ser Val Gly

```
            1               5                   10                  15
Asp Arg Val Thr Ile Thr Cys Thr Ala Ser Ser Ser Val Asn Ser Asn
            20                  25                  30

Tyr Leu His Trp Tyr Gln Gln Lys Pro Gly Lys Ala Pro Lys Leu Leu
            35                  40                  45

Ile Tyr Ser Thr Ser Asn Leu Ala Ser Gly Val Pro Ser Arg Phe Ser
            50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys His Gln Tyr His Arg Ser Pro
            85                  90                  95

Leu Thr Phe Gly Gly Gly Thr Lys Val Glu Ile Lys
            100                 105

<210> SEQ ID NO 81
<211> LENGTH: 122
<212> TYPE: PRT
<213> ORGANISM: Artificial
<220> FEATURE:
<223> OTHER INFORMATION: derived from human and mouse sequences

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Gly Arg Ile Arg Ser Lys Ser Asn Asn Tyr Ala Thr Tyr Tyr Ala Asp
            50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
            85                  90                  95

Tyr Cys Ala Arg Gln Trp Asp Tyr Asp Val Arg Ala Met Asn Tyr Trp
            100                 105                 110

Gly Gln Gly Thr Leu Val Thr Val Ser Ser
            115                 120

<210> SEQ ID NO 82
<211> LENGTH: 122
<212> TYPE: PRT
<213> ORGANISM: Artificial
<220> FEATURE:
<223> OTHER INFORMATION: derived from human and mouse sequences

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Ser Asn Asn Tyr Ala Thr Tyr Tyr Ala Asp
            50                  55                  60

Ser Val Lys Asp Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
```

85                  90                  95

Tyr Cys Ala Arg Gln Trp Asp Tyr Asp Val Arg Ala Met Asn Tyr Trp
                100                 105                 110

Gly Gln Gly Thr Leu Val Thr Val Ser Ser
        115                 120

<210> SEQ ID NO 83
<211> LENGTH: 107
<212> TYPE: PRT
<213> ORGANISM: Artificial
<220> FEATURE:
<223> OTHER INFORMATION: derived from human and mouse sequences

<400> SEQUENCE: 83

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Asp Thr Ala
            20                  25                  30

Val Ala Trp Tyr Gln Gln Lys Pro Gly Gln Pro Pro Lys Leu Leu Ile
        35                  40                  45

Tyr Trp Ala Ser Thr Arg Leu Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Ser Ser Tyr Pro Tyr
                85                  90                  95

Thr Phe Gly Gln Gly Thr Lys Leu Glu Ile Lys
            100                 105

<210> SEQ ID NO 84
<211> LENGTH: 107
<212> TYPE: PRT
<213> ORGANISM: Artificial
<220> FEATURE:
<223> OTHER INFORMATION: derived from human and mouse sequences

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg Leu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Tyr
                85                  90                  95

Thr Phe Gly Gln Gly Thr Lys Leu Glu Ile Lys
            100                 105

<210> SEQ ID NO 85
<211> LENGTH: 367
<212> TYPE: PRT
<213> ORGANISM: marmosets
<220> FEATURE:
<221> NAME/KEY: MISC_FEATURE
<222> LOCATION: (1)..(29)
<223> OTHER INFORMATION: leader sequence
<220> FEATURE:

```
<221> NAME/KEY: mat_peptide
<222> LOCATION: (30)..(367)
<223> OTHER INFORMATION: mature peptide - partial sequence
<220> FEATURE:
<221> NAME/KEY: MISC_FEATURE
<222> LOCATION: (30)..(356)
<223> OTHER INFORMATION: ectodomain

<400> SEQUENCE: 85
```

Met Pro Gly Gly Cys Ser Arg Gly Pro Ala Ala Gly Asn Gly Arg Leu
            -25                 -20                 -15

Arg Leu Ala Arg Leu Ala Leu Val Leu Leu Gly Trp Val Ser Ser Ser
            -10                  -5              -1   1

Ser Pro Thr Ser Ser Ala Ser Ser Ser Ser Ser Ala Pro Phe Leu
     5                  10                  15

Ala Ser Ala Val Ser Ala Gln Pro Leu Pro Gly Gln Cys Pro Ala
 20                  25                  30                  35

Leu Cys Glu Cys Ser Glu Ala Ala Arg Thr Val Lys Cys Val Asn Arg
             40                  45                  50

Asn Leu Thr Glu Val Pro Thr Asp Leu Pro Pro Tyr Val Arg Asn Leu
             55                  60                  65

Phe Leu Thr Gly Asn Gln Leu Ala Val Leu Pro Ala Gly Ala Phe Ala
             70                  75                  80

Arg Val Pro Pro Leu Ala Glu Leu Ala Ala Leu Asn Leu Ser Gly Ser
 85                  90                  95

Arg Leu Glu Asp Val Gln Ala Gly Ala Phe Glu His Leu Pro Ser Leu
100                 105                 110                 115

Arg Gln Leu Asp Leu Ser His Asn Pro Leu Ala Val Leu Ser Pro Phe
             120                 125                 130

Ala Phe Ser Gly Ser Asn Ala Ser Val Ser Ala Pro Ser Pro Leu Val
             135                 140                 145

Glu Leu Ile Leu Asn His Ile Val Pro Pro Glu Asp Glu Arg Asn Asn
             150                 155                 160

Arg Ser Phe Glu Gly Met Val Val Ala Ala Leu Arg Ala Gly Gly Ala
             165                 170                 175

Leu His Gly Leu His Arg Leu Glu Leu Ala Ser Asn His Phe Leu Tyr
180                 185                 190                 195

Leu Pro Arg Asp Val Leu Ala Gln Leu Pro Ser Leu Arg His Leu Asp
             200                 205                 210

Leu Ser Asn Asn Ser Leu Val Ser Leu Thr Tyr Val Ser Phe Arg Asn
             215                 220                 225

Leu Thr His Leu Glu Ser Leu His Leu Glu Asp Asn Ala Leu Lys Val
             230                 235                 240

Leu His Asn Gly Thr Leu Ala Glu Leu Gln Gly Leu Pro His Val Arg
             245                 250                 255

Val Phe Leu Asp Asn Asn Pro Trp Val Cys Asp Cys His Met Ala Asp
260                 265                 270                 275

Met Val Ala Trp Leu Lys Glu Thr Glu Val Val Gln Gly Lys Tyr Gln
             280                 285                 290

Leu Thr Cys Ala Phe Pro Glu Lys Met Arg Asn Arg Val Leu Leu Glu
             295                 300                 305

Leu Asn Ser Ala Asp Leu Asp Cys Asp Pro Ile Leu Pro Pro Ser Leu
             310                 315                 320

Gln Thr Ser Tyr Val Phe Leu Gly Ile Val Leu Ala Leu Ile Gly
             325                 330                 335

```
<210> SEQ ID NO 86
<211> LENGTH: 420
<212> TYPE: PRT
<213> ORGANISM: Cynomologous monkey
<220> FEATURE:
<221> NAME/KEY: MISC_FEATURE
<222> LOCATION: (1)..(29)
<223> OTHER INFORMATION: leader sequence
<220> FEATURE:
<221> NAME/KEY: mat_peptide
<222> LOCATION: (30)..(420)
<220> FEATURE:
<221> NAME/KEY: MISC_FEATURE
<222> LOCATION: (30)..(356)
<223> OTHER INFORMATION: ectodomain

<400> SEQUENCE: 86

Met Pro Gly Gly Cys Ser Arg Gly Pro Ala Ala Gly Asp Gly Arg Leu
                -25                 -20                 -15

Arg Leu Ala Arg Leu Ala Leu Val Leu Leu Gly Trp Val Ser Ser Ser
            -10                  -5                  -1   1

Ser Pro Thr Ser Ser Ala Ser Ser Phe Ser Ser Ala Pro Phe Leu
      5                  10                  15

Ala Ser Ala Ala Ser Ala Gln Pro Pro Leu Pro Asp Gln Cys Pro Ala
 20                  25                  30                  35

Leu Cys Glu Cys Ser Glu Ala Ala Arg Thr Val Lys Cys Val Asn Arg
                 40                  45                  50

Asn Leu Thr Glu Val Pro Thr Asp Leu Pro Leu Tyr Val Arg Asn Leu
             55                  60                  65

Phe Leu Thr Gly Asn Gln Leu Ala Val Leu Pro Ala Gly Ala Phe Ala
             70                  75                  80

Arg Arg Pro Pro Leu Ala Glu Leu Ala Ala Leu Asn Leu Ser Gly Ser
 85                  90                  95

Arg Leu Asp Glu Val Arg Ala Gly Ala Phe Glu His Leu Pro Ser Leu
100                 105                 110                 115

Arg Gln Leu Asp Leu Ser His Asn Pro Leu Ala Tyr Leu Ser Pro Phe
                120                 125                 130

Ala Phe Ser Gly Ser Asn Ala Ser Ile Ser Ala Pro Ser Pro Leu Val
                135                 140                 145

Glu Leu Ile Leu Asn His Ile Val Pro Pro Asp Asp Lys Arg Gln Asn
                150                 155                 160

Arg Ser Phe Glu Gly Met Val Ala Ala Leu Val Ala Gly Arg Ala
165                 170                 175

Leu Gln Gly Leu His Leu Glu Leu Ala Ser Asn His Phe Leu Tyr
180                 185                 190                 195

Leu Pro Arg Asp Val Leu Ala Gln Leu Pro Ser Leu Arg Tyr Leu Asp
                200                 205                 210

Leu Ser Asn Asn Ser Leu Val Ser Leu Thr Tyr Val Ser Phe Arg Asn
                215                 220                 225

Leu Thr His Leu Glu Ser Leu His Leu Glu Asp Asn Ala Leu Lys Val
                230                 235                 240

Leu His Asn Gly Thr Leu Ala Glu Leu Gln Gly Leu Pro His Val Arg
                245                 250                 255

Val Phe Leu Asp Asn Asn Pro Trp Val Cys Asp Cys His Met Ala Asp
260                 265                 270                 275

Met Val Thr Trp Leu Lys Gln Thr Glu Val Gln Gly Lys Asp Arg
                280                 285                 290

Leu Thr Cys Ala Phe Pro Glu Lys Met Arg Asn Arg Val Leu Leu Glu
                295                 300                 305
```

```
Leu Asn Ser Ala Asp Leu Asp Cys Asp Pro Ile Leu Pro Pro Ser Leu
            310                 315                 320

Gln Thr Ser Tyr Val Phe Leu Gly Ile Val Leu Ala Leu Ile Gly Ala
        325                 330                 335

Ile Phe Leu Leu Val Leu Tyr Leu Asn Arg Lys Gly Ile Lys Lys Trp
340                 345                 350                 355

Met His Asn Ile Arg Asp Ala Cys Arg Asp His Met Glu Gly Tyr His
                360                 365                 370

Tyr Arg Tyr Glu Ile Asn Ala Asp Pro Arg Leu Thr Asn Leu Ser Ser
            375                 380                 385

Asn Ser Asp Val
        390

<210> SEQ ID NO 87
<211> LENGTH: 420
<212> TYPE: PRT
<213> ORGANISM: Homo sapiens

<400> SEQUENCE: 87

Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
            20                  25                  30

Ser Pro Thr Ser Ser Ala Ser Ser Phe Ser Ser Ser Ala Pro Phe Leu
        35                  40                  45

Ala Ser Ala Val Ser Ala Gln Pro Pro Leu Pro Asp Gln Cys Pro Ala
    50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Ala Tyr Val Arg Asn Leu
                85                  90                  95

Phe Leu Thr Gly Asn Gln Leu Ala Val Leu Pro Ala Gly Ala Phe Ala
            100                 105                 110

Arg Arg Pro Pro Leu Ala Glu Leu Ala Ala Leu Asn Leu Ser Gly Ser
        115                 120                 125

Arg Leu Asp Glu Val Arg Ala Gly Ala Phe Glu His Leu Pro Ser Leu
    130                 135                 140

Arg Gln Leu Asp Leu Ser His Asn Pro Leu Ala Asp Leu Ser Pro Phe
145                 150                 155                 160

Ala Phe Ser Gly Ser Asn Ala Ser Val Ser Ala Pro Ser Pro Leu Val
                165                 170                 175

Glu Leu Ile Leu Asn His Ile Val Pro Pro Glu Asp Glu Arg Gln Asn
            180                 185                 190

Arg Ser Phe Glu Gly Met Val Val Ala Ala Leu Leu Ala Gly Arg Ala
        195                 200                 205

Leu Gln Gly Leu Arg Arg Leu Glu Leu Ala Ser Asn His Phe Leu Tyr
    210                 215                 220

Leu Pro Arg Asp Val Leu Ala Gln Leu Pro Ser Leu Arg His Leu Asp
225                 230                 235                 240

Leu Ser Asn Asn Ser Leu Val Ser Leu Thr Tyr Val Ser Phe Arg Asn
                245                 250                 255

Leu Thr His Leu Glu Ser Leu His Leu Glu Asp Asn Ala Leu Lys Val
            260                 265                 270

Leu His Asn Gly Thr Leu Ala Glu Leu Gln Gly Leu Pro His Ile Arg
        275                 280                 285
```

Val Phe Leu Asp Asn Asn Pro Trp Val Cys Asp Cys His Met Ala Asp
    290                 295                 300

Met Val Thr Trp Leu Lys Glu Thr Glu Val Val Gln Gly Lys Asp Arg
305                 310                 315                 320

Leu Thr Cys Ala Tyr Pro Glu Lys Met Arg Asn Arg Val Leu Leu Glu
                325                 330                 335

Leu Asn Ser Ala Asp Leu Asp Cys Asp Pro Ile Leu Pro Ser Leu
                340                 345                 350

Gln Thr Ser Tyr Val Phe Leu Gly Ile Val Leu Ala Leu Ile Gly Ala
                355                 360                 365

Ile Phe Leu Leu Val Leu Tyr Leu Asn Arg Lys Gly Ile Lys Lys Trp
    370                 375                 380

Met His Asn Ile Arg Asp Ala Cys Arg Asp His Met Glu Gly Tyr His
385                 390                 395                 400

Tyr Arg Tyr Glu Ile Asn Ala Asp Pro Arg Leu Thr Asn Leu Ser Ser
                405                 410                 415

Asn Ser Asp Val
            420

<210> SEQ ID NO 88
<211> LENGTH: 130
<212> TYPE: PRT
<213> ORGANISM: Homo sapiens

<400> SEQUENCE: 88

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
                20                  25                  30

Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Ser Arg Gly Tyr Ser Tyr Asp Phe Trp Ser Gly Tyr Phe
                100                 105                 110

Tyr Tyr Tyr Tyr Met Asp Val Trp Gly Lys Gly Thr Thr Val Thr Val
            115                 120                 125

Ser Ser
    130

<210> SEQ ID NO 89
<211> LENGTH: 98
<212> TYPE: PRT
<213> ORGANISM: Homo sapiens

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

```
Ala Asn Ile Lys Gln Asp Gly Ser Glu Lys Tyr Tyr Val Asp Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                    85                  90                  95

Ala Arg

<210> SEQ ID NO 90
<211> LENGTH: 98
<212> TYPE: PRT
<213> ORGANISM: Homo sapiens

<400> SEQUENCE: 90

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Lys

<210> SEQ ID NO 91
<211> LENGTH: 98
<212> TYPE: PRT
<213> ORGANISM: Homo sapiens

<400> SEQUENCE: 91

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Arg

<210> SEQ ID NO 92
<211> LENGTH: 98
<212> TYPE: PRT
<213> ORGANISM: Homo sapiens

<400> SEQUENCE: 92

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30
```

Trp Met His Trp Val Arg Gln Ala Pro Gly Lys Gly Leu Val Trp Val
            35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 93
<211> LENGTH: 97
<212> TYPE: PRT
<213> ORGANISM: Homo sapiens

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
            35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg

<210> SEQ ID NO 94
<211> LENGTH: 95
<212> TYPE: PRT
<213> ORGANISM: Homo sapiens

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 95
<211> LENGTH: 95
<212> TYPE: PRT
<213> ORGANISM: Homo sapiens

<400> SEQUENCE: 95

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95
```

<210> SEQ ID NO 96
<211> LENGTH: 95
<212> TYPE: PRT
<213> ORGANISM: Homo sapiens

<400> SEQUENCE: 96

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95
```

<210> SEQ ID NO 97
<211> LENGTH: 95
<212> TYPE: PRT
<213> ORGANISM: Homo sapiens

<400> SEQUENCE: 97

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95
```

<210> SEQ ID NO 98
<211> LENGTH: 101
<212> TYPE: PRT
<213> ORGANISM: Homo sapiens

<400> SEQUENCE: 98

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30
```

```
Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Ser Thr Pro
            100

<210> SEQ ID NO 99
<211> LENGTH: 96
<212> TYPE: PRT
<213> ORGANISM: Homo sapiens

<400> SEQUENCE: 99

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ser Trp Tyr Gln Gln Lys Pro Gly Gln Ala Pro Arg Leu Leu
            35                  40                  45

Ile Tyr Gly Ala Ser Thr Arg Ala Thr Gly Ile Pro Ala Arg Phe Ser
        50                  55                  60

Gly Ser Gly Ser Gly Thr Asp Phe Thr Leu Thr Ile Ser Ser Leu Gln
 65                  70                  75                  80

Pro Glu Asp Phe Ala Val Tyr Tyr Cys Gln Gln Asp Tyr Asn Leu Pro
                85                  90                  95
```

ANTI-5T4 ANTIBODIES AND USES THEREOF

RELATED APPLICATIONS

Priority is claimed to U.S. Provisional Application No. 60/891,248, filed Feb. 23, 2007, and to U.S. Provisional Application No. 60/781,346, filed Mar. 10, 2006, each of which is incorporated by reference in its entirety herein.

FIELD OF THE INVENTION

The present invention generally relates to anti-5T4 antibodies and antibody/drug conjugates (i.e., immunoconjugates) for the diagnosis and/or treatment of neoplastic or malignant disorders. The present invention also relates to isolated variable region nucleic acids and polypeptides for preparing anti-5T4 antibodies and antibody/drug conjugates.

BACKGROUND OF THE INVENTION

The availability of high affinity monoclonal antibodies has enabled the development of targeted immunotherapies. According to this approach, a therapeutic agent is coupled to an antibody with binding specificity for a defined target cell population. Therapeutic agents that have been conjugated to monoclonal antibodies include cytotoxins, biological response modifiers, enzymes (e.g., ribonucleases), apoptosis-inducing proteins and peptides, and radioisotopes. Antibody/cytotoxin conjugates are generally referred to as immunocytotoxins. Antibodies coupled to low-molecular-weight drugs such as methothrexate are typically called chemoantibody/drug conjugates. Conjugates described as immunomodulators contain biological response modifiers such as lymphokines, growth factors, and complement-activating cobra venom factor (CVF). Radiolabeled antibodies include radioactive isotopes that may be used for radiotherapy as well as imaging.

Antibody-mediated drug delivery to tumor cells augments drug efficacy by minimizing its uptake in normal tissues. See e.g., Reff et al. (2002) *Cancer Control* 9:152-66; Sievers (2000) *Cancer Chemother. Pharmacol.* 46 Suppl:S18-22; Goldenberg (2001) *Crit. Rev. Oncol. Hematol.* 39:195-201. MYLOTARG® (gemtuzumab ozogamicin) is a commercially available targeted immunotherapy that works according to this principle and which is approved for the treatment of acute myeloid leukemia in elderly patients. See Sievers et al. (1999) *Blood* 93: 3678-84. In this case, the targeting molecule is an anti-CD33 monoclonal antibody that is conjugated to calicheamicin.

Targeted immunotherapy in humans has nevertheless been limited, in part due to adverse responses to non-human monoclonal antibodies. Early clinical trials using rodent antibodies revealed human anti-mouse antibody (HAMA) and human anti-rat antibody (HARA) responses, which result in rapid antibody clearance. Less immunogenic antibodies have since been developed, including chimeric antibodies, humanized antibodies, PRIMATIZED® antibodies, and human antibodies prepared using transgenic mice or phage display libraries. See Morrison et al. (1984) *Proc. Natl. Acad. Sci. USA* 81:6851-5; Queen et al. (1989) *Proc. Natl. Acad. Sci. USA* 86:10029-33; Newman et al. (1992) *Biotechnology (NY)* 10:1455-60; Green et al. (1994) *Nat. Genet.* 7:13-21; Marks et al. (1991) *J. Mol. Biol.* 222:581-97. Avoidance of a HAMA response permits high dose and repeated dose administration to achieve a therapeutic response.

Candidate antibodies for drug targeting include antibodies that recognize oncofetal antigens, i.e., antigens present on fetal cells and neoplastic cells, and which are largely absent from normal adult cells. See e.g., Magdelenat (1992) *J. Immunol. Methods* 150: 133-43. The 5T4 oncofetal antigen is a 72 kDa highly glycosylated transmembrane glycoprotein comprising a 42 kDa non-glycosylated core (Hole et al. (1988) *Br. J. Cancer* 57: 239-46, Hole et al. (1990) *Int. J. Cancer* 45: 179-84; PCT International Publication No. WO89/07947; U.S. Pat. No. 5,869,053). 5T4 includes an extracellular domain characterized by two leucine-rich repeats (LRRs) and an intervening hydrophilic region, which is an accessible site for targeted therapy (Myers et al. (1994) *J. Biol. Chem.* 269: 9319-24).

Human 5T4 is expressed in numerous cancer types, including carcinomas of the bladder, breast, cervix, endometrium, lung, esophagus, ovary, pancreas, stomach, and testes, and is substantially absent from normal tissues, except for syncytiotrophoblast in placenta (see, e.g., Southall et al. (1990) *Br. J. Cancer* 61: 89-95 (immunohistological distribution of 5T4 antigen in normal and malignant tissues); Mieke et al. (1997) *Clin. Cancer Res.* 3: 1923-1930 (low intercellular adhesion molecule 1 and high 5T4 expression on tumor cells correlate with reduced disease-free survival in colorectal carcinoma patients); Starzynska et al. (1994) *Br. J. Cancer* 69: 899-902 (prognostic significance of 5T4 oncofetal antigen expression in colorectal carcinoma); Starzynska et al. (1992) *Br. J. Cancer* 66: 867-869 (expression of 5T4 antigen in colorectal and gastric carcinoma); Jones et al. (1990) *Br. J. Cancer* 61: 96-100 (expression of 5T4 antigen in cervical cancer); Connor and Stern (199) *Int. J. Cancer* 46: 1029-1034 (loss of MHC class-I expression in cervical carcinomas); Ali et al. (2001) *Oral Oncology* 37: 57-64 (pattern of expression of the 5T4 oncofoetal antigen on normal, dysplastic and malignant oral mucosa); PCT International Publication No. WO89/07947; U.S. Pat. No. 5,869,053). For example, tissues reported to have no expression of 5T4 include the liver, skin, spleen, thymus, central nervous system (CNS), adrenal gland, and ovary. Tissues reported to have focal or low expression of 5T4 include the liver, skin, spleen, lymph node, tonsil, thyroid, prostate, and seminal vesicles. Weak-moderate diffuse expression of 5T4 has been reported in the kidney, lung, pancreas, pharynx, and gastro-intestinal tract. The only tissue reported to have high expression of 5T4 is syncytiotrophoblast; 5T4 was also absent from normal serum or the serum of pregnant women (i.e., levels<10 ng/ml). Overexpression of 5T4 in tumors has been correlated with disease progression, and assessment of 5T4 expression has been suggested as a useful approach for identifying patients with short-term prognosis (Mulder et al. (1997) *Clin. Cancer Res.* 3: 1923-30, Naganuma et al. (2002) *Anticancer Res.* 22: 1033-1038, Starzynska et al. (1994) *Br. J. Cancer* 69: 899-902, Starzynska et al. (1998) *Eur. J. Gastroenterol. Hepatol.* 10: 479-484, Wrigley et al. (1995) *Int. J. Gynecol. Cancer* 5: 269-274).

Several anti-5T4 antibodies have been described, including mAb5T4, also called the H8 antibody, which recognizes a conformational epitope of the 5T4 antigen (Shaw et al. (2002) *Biochem. J.* 363: 137-45, PCT International Publication No. WO98/55607), a rat monoclonal antibody (Woods et al. (2002) *Biochem. J.* 366: 353-65), and a mouse monoclonal antibody called 5T4 (U.S. Pat. No. 5,869,053). Single chain anti-5T4 antibodies have also been described, as well as fusion proteins that include anti-5T4 antibody sequences fused to a therapeutic molecule. For example, anti-5T4 antibody sequences fused to the human IgG1 constant domain or to the extracellular domain of murine B7.1 induces cytolysis of 5T4-expressing tumor cell lines (Myers et al. (2002) *Cancer Gene Ther.* 9: 884-896, Shaw et al. (2000) *Biochim. Biophys. Acta.* 1524: 238-246; U.S. Patent Application Publication No. 2003/0018004). Similarly, a single chain anti-5T4 antibody fused to a superantigen may stimulate T cell-dependent cytolysis of non-small cell lung carcinoma cells in vitro (Forsberg et al. (2001) *Br. J. Cancer* 85: 129-136). A phase I clinical trial using PNU-214936, a murine Fab fragment of the monoclonal antibody 5T4 fused to a mutated superantigen staphylococcal enterocytotoxin A (SEA), showed limited toxicity and some anti-tumor response (Cheng et al. (2004) *J. Clin. Oncol.* 22(4):602-9). As an alternate therapeutic approach, recombinant 5T4 vaccines are also suggested for the treatment of cancers (Mulryan et al. (2002) *Mol. Cancer. Ther.* 1: 1129-37; UK Patent Application Publication Nos. 2,370,571 and 2,378,704; EP Patent Application Publication Nos. EP 1,160,323 and 1,152,060).

The present invention provides novel anti-5T4 antibodies, anti-5T4/drug conjugates, methods for producing the disclosed antibodies and antibody/drug conjugates, and methods for their diagnostic and therapeutic use.

SUMMARY OF THE INVENTION

The present invention provides novel anti-5T4 antibodies, conjugates thereof, and methods for using the same. Also provided are isolated anti-5T4 polypeptides and isolated nucleic acids encoding the same.

Anti-5T4 antibodies of the invention include antibodies that specifically bind human 5T4 antigen, wherein the antibody (a) comprises an antigen binding domain of murine A1, A2, or A3 antibodies; (b) competes for 5T4 binding with murine A1, A2, or A3 antibodies; (c) binds a 5T4 epitope bound by A1, A2, or A3 antibodies; or (d) comprises a 5T4-binding fragment of an antibody of (a)-(c). The anti-5T4 antibodies of the invention may be chimeric, humanized, single chain, an Fab fragment, a F(ab)2 fragment, a Fv fragment, tetrameric, tetravalent, multispecific, domain-specific, a single domain antibody, a fusion protein, or a murine monoclonal. For example, humanized anti-5T4 antibodies of the invention include antibodies comprising at least one heavy chain variable region or at least one light chain variable region, wherein the humanized antibody or antibody fragment: (a) comprises an antigen binding domain of murine A1, A2, or A3 antibodies; (b) competes for 5T4 binding with murine A1, A2, or A3 antibodies; (c) binds a 5T4 epitope bound by A1, A2, or A3 antibodies; or (d) a 5T4-binding fragment of an antibody of (a)-(c).

The anti-5T4 antibodies of the invention have a binding affinity for human 5T4 antigen of at least about $1 \times 10^{-7}$ M to about $1 \times 10^{-12}$ M. The disclosed anti-5T4 antibodies and conjugates thereof may also show specific binding by targeting of 5T4-expressing cells in vivo.

Representative anti-5T4 antibodies of the invention include antibodies comprising a heavy chain variable region comprising (a) an amino acid sequence of residues 20-138 of SEQ ID NO:2; (b) an amino acid sequence that is at least 85% identical to residues 20-138 of SEQ ID NO:2; (c) an amino acid sequence of residues 19-135 of SEQ ID NO:6; (d) an amino acid sequence that is at least 86% identical to residues 19-135 of SEQ ID NO:6; (e) an amino acid sequence of residues 20-141 of SEQ ID NO:10; (f) an amino acid sequence that is at least 91% identical to residues 20-141 of SEQ ID NO:10; (g) an amino acid sequence of any one of SEQ ID NOs:49, 51, 52, 54, 56, 77, 78, 81, or 82; (h) an amino acid sequence that is at least 91% identical to SEQ ID NO:51; (i) an amino acid sequence that is at least 78% identical to SEQ ID NO:54; (j) an amino acid sequence that is at least 89% identical to SEQ ID NO:77; (k) an amino acid sequence that is at least 79% identical to SEQ ID NO:78; (l) an amino acid sequence that is at least 80% identical to SEQ ID NO:81; or (m) an amino acid sequence that is at least 78% identical to SEQ ID NO:82.

Representative anti-5T4 antibodies of the invention include antibodies comprising a light chain variable region comprising (a) an amino acid sequence of residues 21-127 of SEQ ID NO:4; (b) an amino acid sequence that is at least 94% identical to residues 21-127 of SEQ ID NO:4; (c) an amino acid sequence of residues 23-130 of SEQ ID NO:8; (d) an amino acid sequence that is at least 96% identical to residues 23-130 of SEQ ID NO:8; (e) an amino acid sequence of residues 21-127 of SEQ ID NO:12; (f) an amino acid sequence that is at least 98% identical to residues 21-127 of SEQ ID NO:12; (g) an amino acid sequence of any one of SEQ ID NOs: 58, 60, 62, 64, 66, 68, 70, 72, 74, 76, 79, 80, 83, or 84; (h) an amino acid sequence that is at least 83% identical to SEQ ID NO:60; (i) an amino acid sequence that is at least 93% identical to SEQ ID NO:70; (j) an amino acid sequence that is at least 85% identical to SEQ ID NO:76; (k) an amino acid sequence that is at least 85% identical to SEQ ID NO:76; (l) an amino acid sequence that is at least 88% identical to SEQ ID NO:79; (m) an amino acid sequence that is at least 84% identical to SEQ ID NO:80; (n) an amino acid sequence that is at least 90% identical to SEQ ID NO:83; or (o) an amino acid sequence that is at least 91% identical to SEQ ID NO:84.

For example, an anti-5T4 antibody can comprise (a) a heavy chain variable region comprising an amino acid sequence of residues 20-138 of SEQ ID NO:2, and a light chain variable region comprising an amino acid sequence of residues 21-127 of SEQ ID NO:4; (b) a heavy chain variable region comprising an amino acid sequence derived from residues 19-135 of SEQ ID NO:6, and a light chain variable region comprising an amino acid sequence derived from residues 23-130 of SEQ ID NO:8; or (c) a heavy chain variable region comprising an amino acid sequence derived from residues 20-141 of SEQ ID NO:10, and a light chain variable region comprises an amino acid sequence derived from residues 21-127 of SEQ ID NO:12.

Chimeric and humanized anti-5T4 antibodies of the invention may comprise constant regions derived from human constant regions, such as a human light chain constant region derived from human kappa light chain constant region and a human heavy chain constant region derived from a human IgG1 or human IgG4 heavy chain constant region.

Representative humanized anti-5T4 antibodies of the invention include antibodies comprising (a) framework regions comprising residues of a human antibody framework region; and (b) one or more CDRs of the light chain variable region of SEQ ID NO:4, 8, or 12, or one or more CDRs of the heavy chain variable region of SEQ ID NO:2, 6, or 10. For example, residues of a human antibody framework region can comprise (a) a human antibody light chain framework region of a DPK24 subgroup IV germ line clone, a VκIII subgroup (DPK23, DPK22, DPK20, DPK21), or a VκI subgroup germ line clone (DPK9, DPK1, O2, DPK7); (b) a human antibody heavy chain framework region selected from the group consisting of DP-21 (VH7), DP-54 (VH3-07), DP-47 (VH3-23), DP-53 (VH-74), DP-49 (VH3-30), DP-48 (VH3-13), DP-75, DP-8(VH1-2), DP-25, V1-2b and VI-3 (VH1-03), DP-15 and V1-8 (VH1-08), DP-14 and V1-18 (VH1-18), DP-5 and V1-24P (VH1-24), DP-4 (VH1-45), DP-7 (VH1-46), DP-10, DA-6 and YAC-7 (VH1-69), DP-88 (VH1-e), DP-3 and DA-8 (VH1-f); (c) a consensus sequence of a heavy chain framework region of (b); or (d) a framework region that is at least 63% identical to a framework region of (a)-(c).

Representative humanized anti-5T4 antibodies of the invention can also include two or more CDRs of SEQ ID NOs: SEQ ID NOs:2, 4, 6, 8, 10, or 12, such as two or all three CDRs of the light chain variable region of SEQ ID NO:4, 8, or 12, or two or all three CDRs of the heavy chain variable region of SEQ ID NO:2, 6, or 10, or one or more CDRs or the light chain variable region of SEQ ID NO:4, 8, or 12 and one or more CDRs of the heavy chain variable region of SEQ ID NO:2, 6, or 12, or all of the CDRs or SEQ ID NOs: 2, 4, 6, 8, 10, or 12.

Representative chimeric and humanized anti-5T4 antibodies include antibodies comprising a heavy chain variable region sequence comprising (a) an amino acid sequence of residues 20-138 of SEQ ID NO:2; (b) an amino acid sequence that is at least 85% identical to residues 20-138 of SEQ ID NO:2; (c) an amino acid sequence of residues 19-135 of SEQ ID NO:6; (d) an amino acid sequence that is at least 86% identical to residues 19-135 of SEQ ID NO:6; (e) an amino acid sequence of residues 20-141 of SEQ ID NO:10; (f) an amino acid sequence that is at least 91% identical to residues 20-141 of SEQ ID NO:10; (g) an amino acid sequence of residues 1-119 of SEQ ID NO:49; (h) an amino acid sequence that is at least 90% identical to residues 1-119 of SEQ ID NO:49; or (i) an amino acid sequence of a humanized heavy chain variable depicted in FIGS. 9A-9C.

Additional chimeric and humanized anti-5T4 antibodies of the invention include antibodies comprising a heavy chain variable region encoded by a nucleic acid comprising (a) a nucleotide sequence of nucleotides 58-414 of SEQ ID NO:1; (b) a nucleotide sequence of nucleotides 55-405 of SEQ ID NO:5; (c) a nucleotide sequence of nucleotides 58-423 of SEQ ID NO:9; (d) a nucleotide sequence of nucleotides 1-358 of SEQ ID NO:48; (e) a nucleotide sequence encoding a humanized A1, A2, or A3 variable region depicted in FIGS. 9A-9C; (f) a nucleotide sequence that is at least 90% identical to the nucleotide sequence of any one of (a)-(e); or (g) a nucleic acid that specifically hybridizes to the complement of any one of (a)-(e) under stringent hybridization conditions.

Representative chimeric and humanized anti-5T4 antibodies include antibodies comprising a light chain variable region sequence comprising (a) an amino acid sequence of residues 21-127 of SEQ ID NO:4; (b) an amino acid sequence that is at least 94% identical to residues 21-127 of SEQ ID NO:4; (c) an amino acid sequence of residues 23-130 of SEQ ID NO:8; (d) an amino acid sequence that is at least 96% identical to residues 23-130 of SEQ ID NO:8; (e) an amino acid sequence of residues 21-127 of SEQ ID NO:12; (f) an amino acid sequence that is at least 98% identical to residues 21-127 of SEQ ID NO:12; or (g) an amino acid sequence of a humanized A1, A2, or A3 light chain variable region depicted in FIGS. 9A-9C.

Also provided are antibody/drug conjugates for drug delivery comprising (a) a chimeric or humanized anti-5T4 antibody or antibody fragment of the invention; and (b) a drug, which is directly or indirectly bound to the antibody. Representative drugs include therapeutic agents, such as cytotoxins, radioisotopes, immunomodulatory agents, anti-angiogenic agents, anti-proliferative agents, pro-apoptotic agents, chemotherapeutic agents, and therapeutic nucleic acids. A cytotoxin may be, for example, an antibiotic, an inhibitor of tubulin polymerization, an alkylating agent, a protein synthesis inhibitor, a protein kinase inhibitor, a phosphatase inhibitor, a topoisomerase inhibitor, or an enzyme. Antibiotic cytotoxins, such as calicheamicin, N-acetyl-γ-calicheamicin, or derivatives thereof such as N-acetyl-γ-calicheamicin dimethyl hydrazide, are particularly useful for anti-cancer therapies.

The disclosed anti-5T4 antibody/drug conjugates may include a linker for binding the antibody to the drug. Representative linkers include 4-(4'acetylphenoxy)butanoic acid (AcBut), 3-acetylphenyl acidic acid (AcPac), and 4-mercapto-4-methyl-pentanoic acid (Amide). The antibody/drug conjugates may also include polyethylene glycol or other agents to enhance drug incorporation.

For delivery of a drug to 5T4-expressing cells, the present invention provides methods whereby cells are contacted with an antibody/drug conjugate comprising (i) a chimeric or humanized anti-5T4 antibody, and (ii) a drug which is bound to the humanized anti-5T4 antibody directly or indirectly. According to the disclosed methods, the drug is internalized within the target cell. Therapeutic methods are also disclosed herein, which comprise administering to the subject having a 5T4-positive cancer a therapeutically effective amount of an anti-5T4 antibody/drug conjugate comprising (i) a chimeric or humanized anti-5T4 antibody or antibody fragment, and (ii) a therapeutic agent which is bound to the humanized anti-5T4 antibody or antibody fragment directly or indirectly. Anti-5T4 therapies of the invention may be combined with any other known therapy for improved effect. A second therapeutic agent may be administered in combination with an anti-5T4 antibody/drug conjugate simultaneously or consecutively in any order.

Also provided are isolated nucleic acids encoding humanized anti-5T4 variable regions, which are useful for production of the disclosed humanized anti-5T4 antibodies. Representative nucleic acids encoding a humanized anti-5T4 heavy chain variable region include (a) a nucleotide sequence of nucleotides 58-414 of SEQ ID NO:1; (b) a nucleotide sequence of nucleotides 55-405 of SEQ ID NO:5; (c) a nucleotide sequence of nucleotides 58-423 of SEQ ID NO:9; (d) a nucleotide sequence encoding any one of SEQ ID NOs:48, 50, 53, or 55; (e) a nucleotide sequence that is 89% identical to SEQ ID NO:50 when the query coverage is 100%; (f) a nucleotide sequence that is 82% identical to SEQ ID NO:53 when the query coverage is 100%; or (g) a nucleic acid that specifically hybridizes to the complement of any one of (a)-(d) under stringent hybridization conditions. Representative nucleic acids encoding a humanized anti-5T4 light chain variable region include (a) a nucleotide sequence of nucleotides 61-381 of SEQ ID NO:3; (b) a nucleotide sequence of nucleotides 67-390 of SEQ ID NO:7; (c) a nucleotide sequence of nucleotides 61-381 of SEQ ID NO:11; (d) a nucleotide sequence encoding a humanized A1, A2, or A3 light chain variable region of any one of SEQ ID NOs: 57, 59, 61, 63, 65, 67, 69, 71, 73, or 75; (e) a nucleotide sequence that is 84% identical to SEQ ID NO:59 when the query coverage is 100%; (f) a nucleotide sequence that is 86% identical to SEQ ID NO:69 when the query coverage is 100%; (g) a nucleotide sequence that is 85% identical to SEQ ID NO:75 when the query coverage is 100%; or (h) a nucleic acid that specifically hybridizes to the complement of any one of (a)-(d) under stringent hybridization conditions.

BRIEF DESCRIPTION OF THE DRAWINGS

FIGS. 1A-1C show the nucleotide and amino acid sequences of the heavy chain and light chain variable regions of murine anti-5T4 antibodies A1, A2, and A3. The amino acid sequences are annotated to identify complementarity determining regions (CDRs) by underlining and the leader sequence by double-underlining.

FIG. 8 shows the results of spheroid assays performed as described in Example 6. Anti-5T4/calicheamicin conjugates prepared using the A1 and A3 antibodies significantly inhibited growth of 5T4-expressing cells (MDAMB435/5T4) as compared to control cells (MDAMB435/neo). CMA-676, anti-CD33/calicheamicin conjugate; huH8-AcBut-CalichDMH, humanized H8 antibody conjugated to calicheamicin using 4-(4'-acetylphenoxy)butanoic acid (AcBut); CalichDMH, unconjugated calicheamicin; A1-AcBut-CalichDMH, A1 antibody conjugated to calicheamicin using 4-(4'-acetylphenoxy)butanoic acid (AcBut); A3-AcBut-CalichDMH, A3 antibody conjugated to calicheamicin using 4-(4'-acetylphenoxy)butanoic acid (AcBut).

FIGS. 9A-9H show nucleotide and amino acid sequences of the humanized A1 heavy chain variable region version 1 (SEQ ID NOs:48-49); amino acid sequences of humanized A1 heavy chain variable region (huA1 VH) versions 1.2 and 2.0; amino acid sequences of humanized A1 light chain variable region (huA1 VL) versions 1.0, 2.0, and 3.0; amino acid sequences of humanized A2 heavy chain variable region versions 1.0 and 2.0 (huA2 VH); amino acid sequences of humanized A2 light chain variable region versions 1.0 and 2.0 (huA2 VL); amino acid sequences of humanized A3 heavy chain variable region versions 1.0 and 2.0 (huA3 VH); and amino acid sequences of humanized A3 light chain variable region versions 1.0 and 2.0 (huA32 VL). CDRs are underlined.

FIGS. 10A-10B show representative human heavy chain variable region framework sequences that may be used to prepare humanized anti-5T4 antibodies. FIG. 10A is an alignment of human heavy chain variable region sequences of subgroup I (SEQ ID NOs:14-24) and the consensus framework sequences derived there from (SEQ ID NOs:25-27). FIG. 10B shows the sequences of human germline genes of the VH 7 and VH 3 subgroups (SEQ ID NOs:88-93).

FIG. 11 is an alignment of human light chain variable region sequences of subgroup VκIII (SEQ ID NOs:29-34). Boxed sequences, CDRs.

FIG. 12 is an alignment of human light chain variable region sequences of subgroup VκI (SEQ ID NOs:35-44). Boxed sequences, CDRs.

FIG. 13 shows additional human germline sequences of Vk 1 and Vk IV subgroups, which have framework regions that may be used to prepare humanized anti-5T4 antibodies (SEQ ID NOs:94-99).

FIG. 14 shows the amino acid sequences of representative human constant regions that may be used to prepare chimeric and humanized anti-5T4 antibodies (SEQ ID NOs:45-47).

FIG. 15 shows the amino acid sequences of a full-length cynomologous monkey 5T4 antigen and a partial black-tailed marmoset 5T4 antigen. Underlined sequences, leader sequences. For each sequence, the 5T4 ectodomain includes amino acids 30-356.

DETAILED DESCRIPTION OF THE INVENTION

I. Anti-5T4 Antibodies

The present invention provides novel murine antibodies that bind human 5T4 antigen and that are useful for developing targeted immunotherapies. The human 5T4 antigen is a 72 kDa non-glycosylated phosphoprotein found on the surface of trophoblast cells and numerous cancer cell types See Hole et al. (1988) *Br. J. Cancer* 57: 239-46, Hole et al. (1990) *Int. J. Cancer* 45: 179-184; PCT International Publication No. WO89/07947; U.S. Pat. No. 5,869,053.

The murine anti-5T4 antibodies of the invention are designated A1, A2, and A3, and were prepared as described in Example 1. Also provided are anti-5T4 antibodies derived from A1, A2, and A3, and which specifically bind to human 5T4 antigen. For example, anti-5T4 antibodies of the invention include antibodies comprising antigen binding residues from the A1, A2, and A3 antibodies; antibodies that compete for binding to 5T4 antigen with A1, A2, or A3 antibodies; and antibodies that bind to the same 5T4 epitope as A1, A2, or A3 antibodies.

Figure 6A:
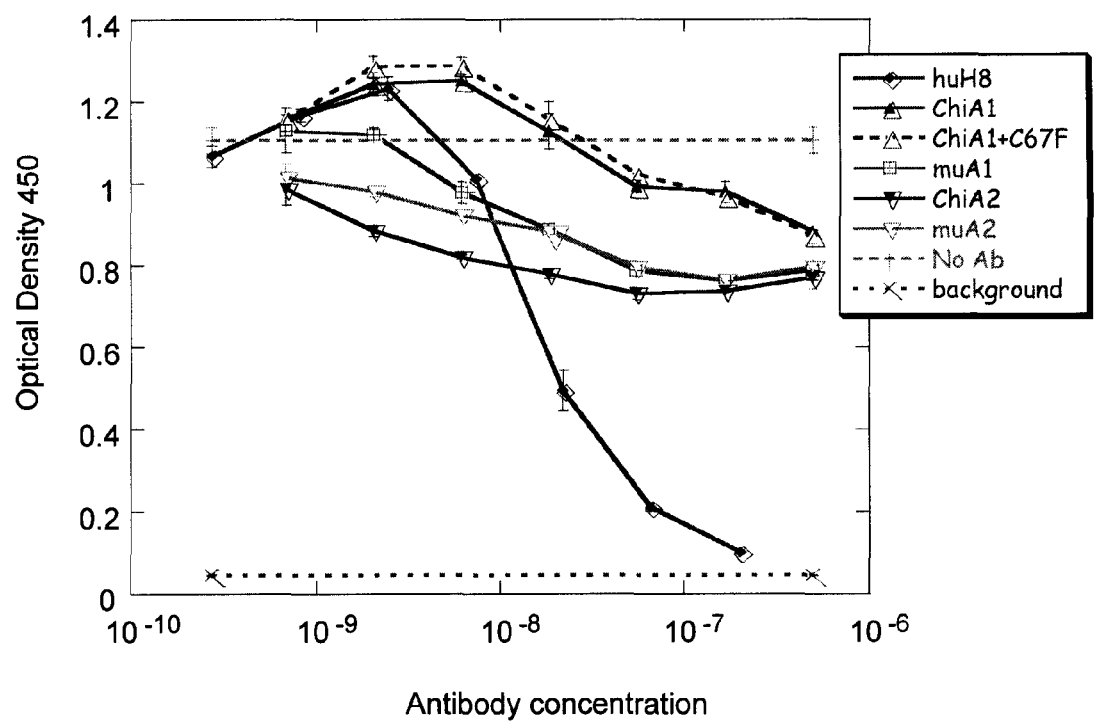
FIGS. 6A-6B show graphical results of competitive binding of humanized H8 and each of the indicated antibodies to human 5T4 ectodomain Fc fusion protein. HuH8, humanized H8 antibody; ChiA1, chimeric A1 antibody; ChiA1+C67F, chimeric A1 antibody bearing C67F mutation; ChiA2, chimeric A2 antibody; muA2, murine A2 antibody; ChiA3, chimeric A3 antibody; ChiA3+C91Y, chimeric A3 antibody bearing C91Y mutation, muA3, murine A3 antibody; No Ab, no antibody (control).
Figure 6B:
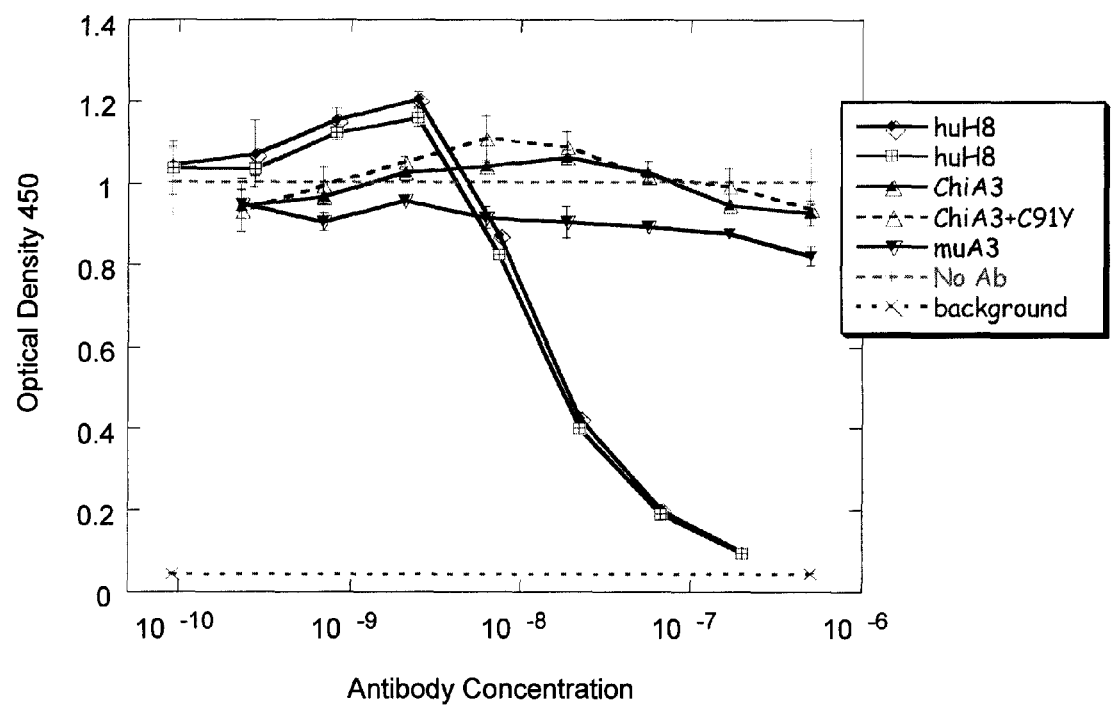

In particular, the disclosed A1, A2, and A3 antibodies each comprise an antigen binding site that recognizes a unique epitope on the human 5T4 antigen. Each of these antibodies also binds to an epitope distinct from that bound by H8, and each of A1, A2, and A3 fails to compete with the H8 antibody for binding to human 5T4. See Examples 4-5 and FIGS. 6-7. Accordingly, the present invention provides antibodies that specifically bind to residues 30-163 of human 5T4 (e.g., A3), antibodies that specifically bind to residues 224-276 of human 5T4 (e.g., A1), and antibodies that specifically bind to residues 224-355 of human 5T4 (e.g., A2). Also provided are human 5T4 antigens comprising epitopes bound by an A1, A2, or A3 antibody. For example, the invention provides 5T4 antigenic fragments comprising residues 30-163, 224-276, and 224-355 of a native or full-length 5T4 antigen.

Specific binding of the disclosed anti-5T4 antibodies refers to a preferential binding of an antibody to human 5T4 antigen in a heterogeneous sample comprising multiple different antigens. Typically, specific binding occurs if the binding affinity is at least about $10^{-7}$ M or higher, such as at least about $10^{-8}$ M or higher, including at least about $10^{-9}$ M or higher, at least about $10^{-11}$ M or higher, or at least about $10^{-12}$ M or higher. For example, specific binding of an antibody of the invention to a human 5T4 antigen includes binding in the range of at least about $1\times10^{-7}$ M to about $1\times10^{-12}$ M, such as within the range of about $1\times10^{-8}$ M to about $1\times10^{-12}$ M, or within the range of about $1\times10^{-8}$ M to about $1\times10^{-11}$ M, or within the range of about 1×10$^{-8}$ M to about 1×10$^{-10}$ M, or within the range of about 1×10$^{-9}$ M to about 1×10$^{-10}$ M. Specific binding also refers to selective targeting of an anti-5T4 antibody to 5T4-expressing cells following administration of the antibody to a subject.

The anti-5T4 antibodies of the invention may have a tetrameric structure (e.g., similar to naturally occurring antibodies), or they may comprise any other structure having at least one immunoglobulin light chain variable region or at least one immunoglobulin heavy chain region, or 5T4-binding fragments thereof (e.g., Fab, modified Fab, F(ab')$_2$ or Fv fragments. Also included are single domain antibodies, in which one or more complementarity determining regions (CDRs), but less than all six CDRs, constitute an antigen binding region. The invention also encompasses chimeric antibodies, humanized antibodies, superhumanized antibodies, diabodies, single chain antibodies, tetravalent antibodies, and/or multispecific antibodies (e.g., bispecific antibodies). These antibody descriptors are not mutually exclusive.

Naturally occurring antibodies are tetrameric (H$_2$L$_2$) glycoproteins of about 150,000 daltons, composed of two identical light (L) chains and two identical heavy (H) chains. The two heavy chains are linked to each other by disulfide bonds and each heavy chain is linked to a light chain by a disulfide bond. Each of the light and heavy chains is further characterized by an amino-terminal variable region and a constant region. The variable regions include sequences that differ extensively among antibodies and substantially determine the binding affinity and specificity of a particular antibody for its particular antigen. The variable regions of each of the light and heavy chains align to form the antigen-binding domain.

Chimeric antibodies comprise sequences from at least two different species. As one example, recombinant cloning techniques may be used to include variable regions, which contain the antigen-binding sites, from a non-human antibody (i.e., an antibody prepared in a non-human species immunized with the antigen) and constant regions derived from a human immunoglobulin.

Chimeric anti-5T4 antibodies of the invention include antibodies comprising heavy chain and light chain variable regions of the A1, A2, and A3 antibodies, i.e., (a) a heavy chain variable region having an amino acid sequence of residues 20-138 of SEQ ID NO:2 and a light chain variable region having an amino acid sequence of residues 21-127 of SEQ ID NO:4; (b) a heavy chain amino acid sequence of residues 19-135 of SEQ ID NO:6 and a light chain amino acid sequence of residues 23-130 of SEQ ID NO:8; and (c) a heavy chain amino acid sequence of residues 20-141 of SEQ ID NO:10 and a light chain amino acid sequence of residues 21-127 of SEQ ID NO:12. Representative humanized anti-5T4 antibodies may include a heavy chain variable region set for as amino acids 1-119 of SEQ ID NO:49, or any one of the humanized heavy chain variable region depicted in FIGS. 9A-9C, and a humanized light chain variable region, also depicted in FIGS. 9A-9C. Preparation of representative chimeric and humanized anti-5T4 antibodies of the invention is described in Example 7.

Anti-5T4 antibodies of the invention may also comprise a heavy chain and/or light chain variable region comprising an amino acid sequence that is derived from or substantially similar to the A1, A2, or A3 variable regions, or substantially similar to the humanized A1, A2, and A3 variable regions. With respect to substantially identical heavy chain and light chain variable regions, the substantially identical sequences are at least about 90% identical to the variable region sequences of any one of SEQ ID NOs:1-12 or to the humanized A1, A2, and A3 variable regions depicted in FIGS. 9A-9C, such as at least 91% identical, or at least 92% identical, or at least 93% identical, or at least 94% identical, or at least 95% identical, or at least 96% identical, or at least 97% identical, or at least 98% identical, or at least 99% identical.

Representative chimeric anti-5T4 antibodies of the invention, i.e., antibodies that specifically bind to 5T4 antigen, also include those antibodies having (a) a heavy chain variable region amino acid sequence set forth as residues 20-138 of SEQ ID NO:2, residues 19-135 of SEQ ID NO:6, residues 20-141 of SEQ ID NO:10, or any one of the humanized A1, A2, or A3 heavy chain variable regions depicted in FIGS. 9A-9C; (b) a heavy chain variable region amino acid sequence that is at least 85% identical to residues 20-138 of SEQ ID NO:2; (c) a heavy chain variable region amino acid sequence that is at least 86% identical to residues 19-135 of SEQ ID NO:6; (d) a heavy chain variable region amino acid sequence that is at least 91% identical to residues 20-141 of SEQ ID NO:10; (e) a heavy chain variable region amino acid sequence that is at least 90% identical to residues 1-119 of SEQ ID NO:49; or (f) a heavy chain variable region amino acid sequence derived from any one of the humanized A1, A2, or A3 variable regions depicted in FIGS. 9A-9C.

A heavy chain variable region of a chimeric or humanized anti-5T4 antibody, which specifically binds to 5T4 antigen, may be encoded by (a) a nucleic acid comprising a nucleotide sequence of nucleotides 58-414 of SEQ ID NO:1, nucleotides 55-405 of SEQ ID NO:5, nucleotides 58-423 of SEQ ID NO:9, nucleotides 1-358 of SEQ ID NO:48; or a nucleic acid encoding a humanized A1, A2, or A3 heavy chain variable region depicted in FIGS. 9A-9C; (b) a nucleic acid comprising a nucleotide sequence that is at least 90% identical to a nucleic acid comprising a nucleotide sequence of nucleotides 58-414 of SEQ ID NO:1, nucleotides 55-405 of SEQ ID NO:5, or nucleotides 58-423 of SEQ ID NO:9. For example, a heavy chain variable region of a chimeric anti-5T4 antibody may be encoded by a nucleic acid that is at least 98% identical to nucleotides 58-414 of SEQ ID NO:1, a nucleic acid comprising a nucleotide sequence that is at least 98% identical to nucleotides 55-405 of SEQ ID NO:5, or a nucleic acid comprising a nucleotide sequence that is at least 89% identical to nucleotides 1-358 of SEQ ID NO:48. A heavy chain variable region of a chimeric anti-5T4 antibody may also be encoded by a nucleic acid that specifically hybridizes to the complement of a nucleic acid comprising a nucleotide sequence of nucleotides 58-414 of SEQ ID NO:1, nucleotides 55-405 of SEQ ID NO:5, nucleotides 58-423 of SEQ ID NO:9, or nucleotides 1-358 of SEQ ID NO:48, under stringent hybridization conditions, for example final wash conditions of 0.1×SSC at 65° C.

Representative chimeric anti-5T4 antibodies of the invention further include those antibodies having (a) a light chain variable region amino acid sequence set forth as residues 21-127 of SEQ ID NO:4, residues 23-130 of SEQ ID NO:8, residues 21-127 of SEQ ID NO:12, or residues of a humanized A1, A2, or A3 light chain variable region depicted in FIGS. 9A-9C; or (b) a light chain variable region amino acid sequence that is at least 90% identical to residues 21-127 of SEQ ID NO:4, residues 23-130 of SEQ ID NO:8, or residues 21-127 of SEQ ID NO:12. For example, a light chain variable region amino acid sequence may comprise (a) a light chain variable region amino acid sequence that is at least 94% identical to residues 21-127 of SEQ ID NO:4; (b) a light chain variable region amino acid sequence that is at least 96% identical to residues 23-130 of SEQ ID NO:8; (c) a light chain variable region amino acid sequence that is at least 98% identical to residues 21-127 of SEQ ID NO:12; (d) or a light chain variable region amino acid sequence derived from any one of the humanized A1, A2, or A3 light chain variable regions depicted in FIGS. 9A-9C.

A light chain variable region of a chimeric anti-5T4 antibody, which specifically binds to 5T4 antigen, may be encoded by (a) a nucleic acid comprising a nucleotide sequence of nucleotides 61-381 of SEQ ID NO:3, nucleotides 67-390 of SEQ ID NO:7, nucleotides 61-381 of SEQ ID NO:11, or nucleotides encoding any one of the humanized A1, A2, or A3 light chain variable regions depicted in FIGS. 9A-9C; or (b) a nucleic acid comprising a nucleotide sequence that is at least 90% identical to nucleotides 61-381 of SEQ ID NO:3, nucleotides 67-390 of SEQ ID NO:7, or nucleotides 61-381 of SEQ ID NO:11. For example, a light chain variable region of a chimeric anti-5T4 antibody may be encoded by a nucleic acid comprising (a) a nucleotide sequence that is at least 97% identical to nucleotides 61-381 of SEQ ID NO:3; (b) a nucleotide sequence that is at least 98% identical to nucleotides 67-390 of SEQ ID NO:7; or (c) a nucleotide sequence that is at least 99% identical to nucleotides 61-381 of SEQ ID NO:11. A light chain variable region of a chimeric anti-5T4 antibody, which specifically binds to 5T4 antigen, may also be encoded by a nucleic acid that specifically hybridizes to the complement of a nucleic acid comprising a nucleotide sequence of nucleotides 61-381 of SEQ ID NO:3, nucleotides 67-390 of SEQ ID NO:7, or nucleotides 61-381 of SEQ ID NO:11, under stringent hybridization conditions, for example final wash conditions of 0.1× SSC at 65° C.

Humanized antibodies are a type of chimeric antibody wherein variable region residues responsible for antigen binding (i.e., residues of a complementarity determining region, abbreviated complementarity determining region, or any other residues that participate in antigen binding) are derived from a non-human species, while the remaining variable region residues (i.e., residues of the framework regions) and constant regions are derived, at least in part, from human antibody sequences. A subset of framework region residues and constant region residues of a humanized antibody may be derived from non-human sources. Variable regions of a humanized antibody are also described as humanized (i.e., a humanized light or heavy chain variable region). The non-human species is typically that used for immunization with antigen, such as mouse, rat, rabbit, non-human primate, or other non-human mammalian species. Humanized antibodies are typically less immunogenic than traditional chimeric antibodies and show improved stability following administration to humans. See e.g., Benincosa et al. (2000) *J. Pharmacol. Exp. Ther.* 292:810-6; Kalofonos et al. (1994) *Eur. J. Cancer* 30A:1842-50; Subramanian et al. (1998) *Pediatr. Infect. Dis. J.* 17:110-5.

Complementarity determining regions (CDRs) are residues of antibody variable regions that participate in antigen binding. Several numbering systems for identifying CDRs are in common use. The Kabat definition is based on sequence variability, and the Chothia definition is based on the location of the structural loop regions. The AbM definition is a compromise between the Kabat and Chothia approaches. The CDRs of the light chain variable region are bounded by the residues at positions 24 and 34 (CDR1-L), 50 and 56 (CDR2-L), and 89 and 97 (CDR3-L) according to the Kabat, Chothia, or AbM algorithm. According to the Kabat definition, the CDRs of the heavy chain variable region are bounded by the residues at positions 31 and 35B (CDR1-H), 50 and 65 (CDR2-H), and 95 and 102 (CDR3-H) (numbering according to Kabat). According to the Chothia definition, the CDRs of the heavy chain variable region are bounded by the residues at positions 26 and 32 (CDR1-H), 52 and 56 (CDR2-H), and 95 and 102 (CDR3-H) (numbering according to Chothia). According to the AbM definition, the CDRs of the heavy chain variable region are bounded by the residues at positions 26 and 35B (CDR1-H), 50 and 58 (CDR2-H), and 95 and 102 (CDR3-H) (numbering according to Kabat). See Martin et al. (1989) *Proc. Natl. Acad. Sci. USA* 86: 9268-9272; Martin et al. (1991) *Methods Enzymol.* 203: 121-153; Pedersen et al. (1992) *Immunomethods* 1: 126; and Rees et al. (1996) In Sternberg M. J. E. (ed.), *Protein Structure Prediction*, Oxford University Press, Oxford, pp. 141-172.

Specificity determining regions (SDRs) are residues within CDRs that directly interact with antigen. The SDRs correspond to hypervariable residues. See (Padlan et al. (1995) *FASEB J.* 9: 133-139).

Framework residues are those residues of antibody variable regions other than hypervariable or CDR residues. Framework residues may be derived from a naturally occurring human antibody, such as a human framework that is substantially similar to a framework region of the A1, A2, or A3 antibodies. Artificial framework sequences that represent a consensus among individual sequences may also be used. When selecting a framework region for humanization, sequences that are widely represented in humans may be preferred over less populous sequences. Additional mutations of the human framework acceptor sequences may be made to restore murine residues believed to be involved in antigen contacts and/or residues involved in the structural integrity of the antigen-binding site, or to improve antibody expression. A peptide structure prediction may be used to analyze the humanized variable heavy and light region sequences to identify and avoid post-translational protein modification sites introduced by the humanization design.

Humanized antibodies may be prepared using any one of a variety of methods including veneering, grafting of complementarity determining regions (CDRs), grafting of abbreviated CDRs, grafting of specificity determining regions (SDRs), and Frankenstein assembly, as described below. Humanized antibodies also include superhumanized antibodies, in which one or more changes have been introduced in the CDRs. For example, human residues may be substituted for non-human residues in the CDRs. These general approaches may be combined with standard mutagenesis and synthesis techniques to produce an anti-5T4 antibody of any desired sequence.

Veneering is based on the concept of reducing potentially immunogenic amino acid sequences in a rodent or other non-human antibody by resurfacing the solvent accessible exterior of the antibody with human amino acid sequences. Thus, veneered antibodies appear less foreign to human cells than the unmodified non-human antibody. See Padlan (1991) *Mol. Immunol.* 28:489-98. A non-human antibody is veneered by identifying exposed exterior framework region residues in the non-human antibody, which are different from those at the same positions in framework regions of a human antibody, and replacement of the identified residues with amino acids that typically occupy these same positions in human antibodies.

Grafting of CDRs is performed by replacing one or more CDRs of an acceptor antibody (e.g., a human antibody or other antibody comprising desired framework residues) with CDRs of a donor antibody (e.g., a non-human antibody). Acceptor antibodies may be selected based on similarity of framework residues between a candidate acceptor antibody and a donor antibody. For example, according to the Frankenstein approach, human framework regions are identified as having substantial sequence homology to each framework region of the relevant non-human antibody, and CDRs of the non-human antibody are grafted onto the composite of the different human framework regions. A related method also useful for preparation of antibodies of the invention is described in U.S. Patent Application Publication No. 2003/0040606.

Grafting of abbreviated CDRs is a related approach. Abbreviated CDRs include the specificity-determining residues and adjacent amino acids, including those at positions 27d-34, 50-55 and 89-96 in the light chain, and at positions 31-35b, 50-58, and 95-101 in the heavy chain (numbering convention of (Kabat et al. (1987)). See (Padlan et al. (1995) *FASEB J.* 9: 133-9). Grafting of specificity-determining residues (SDRs) is premised on the understanding that the binding specificity and affinity of an antibody combining site is determined by the most highly variable residues within each of the complementarity determining regions (CDRs). Analysis of the three-dimensional structures of antibody-antigen complexes, combined with analysis of the available amino acid sequence data may be used to model sequence variability based on structural dissimilarity of amino acid residues that occur at each position within the CDR. SDRs are identified as minimally immunogenic polypeptide sequences consisting of contact residues. See Padlan et al. (1995) *FASEB J.* 9: 133-139.

In general, human acceptor frameworks are selected on the basis that they are substantially similar to the framework regions of the donor antibodies, or which are most similar to the consensus sequence of the variable region subfamily. Following grafting, additional changes may be made in the donor and/or acceptor sequences to optimize antibody binding, functionality, codon usage, expression levels, etc, including introduction of non-human residues into the framework regions. See e.g., PCT International Publication No. WO 91/09967.

For grafting of CDRs onto a heavy chain variable framework region, useful framework sequences may be derived from a DP-21 (VH7), DP-54 (VH3-07), DP-47 (VH3-23), DP-53 (VH-74), DP-49 (VH3-30), DP-48 (VH3-13), DP-75, DP-8(VH1-2), DP-25, VI-2b and VI-3 (VH1-03), DP-15 and V1-8 (VH1-08), DP-14 and V1-18 (VH1-18), DP-5 and V1-24P (VH1-24), DP-4 (VH1-45), DP-7 (VH1-46), DP-10, DA-6 and YAC-7 (VH1-69), DP-88 (VH1-e), DP-3 and DA-8 (VH1-f). Representative heavy chain variable regions containing framework residues for humanization are set forth as SEQ ID NOs:13-24 and 88-93. Representative frameworks that represent a consensus of VH1 framework residues are set forth as SEQ ID NOs:25-27. See also FIGS. 10A-10B.

For grafting of CDRs onto a light chain variable framework region, useful framework sequences may be derived from a DPK24 subgroup IV germ line clone, a VκIII subgroup (DPK23, DPK22, DPK20, DPK21), or a VκI subgroup germ line clone (DPK9, DPK1, O2, DPK7). Representative light chain variable regions containing framework residues for humanization are set forth as SEQ ID NOs:28-34, 35-44, and 94-99. See FIGS. 11-14.

Representative humanized anti-5T4 antibodies of the invention include antibodies having one or more CDRs of a non-human anti-5T4 antibody selected from CDRs of a heavy chain variable region of any one of SEQ ID NOs:2, 6, or 10, or a light chain variable region of any one of SEQ ID NOs:4, 8, or 12. For example, humanized anti-5T4 antibodies may comprise two or more CDRs selected from CDRs of a heavy chain variable region of any one of SEQ ID NOs:2, 6, or 10, or a light chain variable region of any one of SEQ ID NOs:4, 8, or 12. Humanized anti-5T4 antibodies may also comprise a heavy chain comprising a variable region having two or three CDRs of any one of SEQ ID NOs:2, 6, or 10, and a light chain comprising a variable region having two or three CDRs of any one of SEQ ID NOs:4, 8, or 12.

Humanized anti-5T4 antibodies of the invention may be constructed wherein the variable region of a first chain (i.e., the light chain variable region or the heavy chain variable region) is humanized, and wherein the variable region of the second chain is not humanized (i.e., a variable region of an antibody produced in a non-human species). These antibodies are a type of humanized antibody referred to as semi-humanized antibodies. Non-human anti-5T4 antibodies that may be used to prepare semi-humanized antibodies include the A1, A2, and A3 antibodies, as disclosed herein, as well as the H8 antibody described in PCT International Publication No. WO 98/55607 and in Forsberg et al. (1997) *J. Biol. Chem.* 272 (19):124430-12436, or the rat monoclonal antibody described in Woods et al. (2002) *Biochem. J.* 366: 353-65). For example, a semi-humanized anti-5T4 antibody can comprise a heavy chain variable region set for as amino acids 1-119 of SEQ ID NO:49 or amino acids of a humanized A1, A2, or A3 heavy chain variable region depicted in FIGS. 9A-9C, and a light chain variable region of any one of SEQ ID NOs:4, 8, or 12.

The constant regions of chimeric and humanized anti-5T4 antibodies may be derived from constant regions of any one of IgA, IgD, IgE, IgG, IgM, any isotypes thereof (e.g., IgG1, IgG2, IgG3, or IgG4 isotypes of IgG), as well as mutated versions thereof. The choice of a human isotype and modification of particular amino acids in the isotype may enhance or eliminate activation of host defense mechanisms and alter antibody biodistribution. See (Reff et al. (2002) *Cancer Control* 9: 152-66). Representative constant regions useful for preparing chimeric and humanized antibodies of the invention are set forth as SEQ ID NOs: 45-47. Human lambda light chain constant regions, included variant or mutant versions, may also be used. For cloning of sequences encoding immunoglobulin constant regions, intronic sequences may be deleted.

Chimeric and humanized anti-5T4 antibodies may be constructed using standard techniques known in the art. For example, variable regions may be prepared by annealing together overlapping oligonucleotides encoding the variable regions and ligating them into an expression vector containing a human antibody constant region. See e.g., Harlow & Lane (1988) *Antibodies: A Laboratory Manual*, Cold Spring Harbor Laboratory Press, Cold Spring Harbor, N.Y. and U.S. Pat. Nos. 4,196,265; 4,946,778; 5,091,513; 5,132,405; 5,260, 203; 5,677,427; 5,892,019; 5,985,279; 6,054,561. Tetravalent antibodies ($H_4L_4$) comprising two intact tetrameric antibodies, including homodimers and heterodimers, may be prepared, for example, as described in PCT International Publication No. WO 02/096948. Antibody dimers may also be prepared via introduction of cysteine residue(s) in the antibody constant region, which promote interchain disulfide bond formation, by use of heterobifunctional cross-linkers (Wolff et al. (1993) *Cancer Res.* 53: 2560-5), or by recombinant production to include a dual constant region (Stevenson et al. (1989) *Anticancer Drug Des.* 3: 219-30). Antigen-binding fragments of antibodies of the invention may be prepared, for example, by expression of truncated antibody sequences, or by post-translation digestion of full-length antibodies.

Variants of anti-5T4 antibodies of the invention, i.e., the A1, A2, and A3 antibodies as well as chimeric and humanized versions thereof, may be readily prepared to include various changes, substitutions, insertions, and deletions. For example, antibody sequences may be optimized for codon usage in the cell type used for antibody expression. To increase the serum half life of the antibody, a salvage receptor binding epitope may be incorporated, if not present already, into the antibody heavy chain sequence. See U.S. Pat. No. 5,739,277. Additional modifications to enhance antibody stability include modification of IgG4 to replace the serine at residue 241 with proline. See Angal et al. (1993) *Mol. Immunol.* 30: 105-108. Other useful changes include substitutions as required to optimize efficiency in conjugating the antibody with a drug. For example, an antibody may be modified at its carboxyl terminus to include amino acids for drug attachment, for example one or more cysteine residues may be added. The constant regions may be modified to introduce sites for binding of carbohydrates or other moieties.

Variants of anti-5T4 antibodies of the invention may be produced using standard recombinant techniques, including site-directed mutagenesis, or recombination cloning. A diversified repertoire of anti-5T4 antibodies may be prepared via gene arrangement and gene conversion methods in transgenic non-human animals (U.S. Patent Publication No. 2003/0017534), which are then tested for relevant activities using functional assays. In particular embodiments of the invention, anti-5T4 variants are obtained using an affinity maturation protocol for mutating CDRs (Yang et al. (1995) *J. Mol. Biol.* 254: 392-403), chain shuffling (Marks et al. (1992) *Biotechnology (NY)* 10: 779-783), use of mutator strains of *E. coli* (Low et al. (1996) *J. Mol. Biol.* 260: 359-368), DNA shuffling (Patten et al. (1997) *Curr. Opin. Biotechnol.* 8: 724-733), phage display (Thompson et al. (1996) *J. Mol. Biol.* 256: 77-88), and sexual PCR (Crameri et al. (1998) *Nature* 391: 288-291). For immunotherapy applications, relevant functional assays include specific binding to human 5T4 antigen, antibody internalization, and targeting to a tumor site(s) when administered to a tumor-bearing animal, as described herein below.

The present invention further provides cells and cell lines expressing anti-5T4 antibodies of the invention. Representative host cells include mammalian and human cells, such as CHO cells, HEK-293 cells, HeLa cells, CV-1 cells, and COS cells. Methods for generating a stable cell line following transformation of a heterologous construct into a host cell are known in the art. Representative non-mammalian host cells include insect cells (Potter et al. (1993) *Int. Rev. Immunol.* 10(2-3):103-112). Antibodies may also be produced in transgenic animals (Houdebine (2002) *Curr. Opin. Biotechnol.* 13(6):625-629) and transgenic plants (Schillberg et al. (2003) *Cell Mol. Life. Sci.* 60(3):433-45).

II. Anti-5T4 Nucleic Acids and Polypeptides

The present invention further provides isolated nucleic acids encoding anti-5T4 heavy chain and light chain variable regions, and isolated polypeptides encoded by the disclosed nucleic acids. Nucleic acids and polypeptides of the invention include the nucleotide and amino acid sequences of the A1, A2, and A3 variable regions, humanized A1, A2, and A3 variable regions, and variants thereof. The isolated nucleic acids and polypeptides may be used to prepare chimeric and humanized anti-5T4 antibodies.

II.A. Anti-5T4 Nucleic Acids

Nucleic acids are deoxyribonucleotides or ribonucleotides and polymers thereof in single-stranded, double-stranded, or triplexed form. Unless specifically limited, nucleic acids may contain known analogues of natural nucleotides that have similar properties as the reference natural nucleic acid. Nucleic acids include genes, cDNAs, mRNAs, and cRNAs. Nucleic acids may be synthesized, or may be derived from any biological source, including any organism. Representative methods for cloning nucleic acids that encode anti-5T4 antibodies are described in Examples 1 and 7.

Representative nucleic acids of the invention comprise the nucleotide sequence of any one of SEQ ID NOs:1, 3, 5, 7, 9, 11, and 48. In particular, nucleic acids encoding the A1, A2, and A3 heavy chain variable regions comprise nucleotides 58-41 of SEQ ID NO:1, nucleotides 55-405 of SEQ ID NO:5, and nucleotides 58-423 of SEQ ID NO:9, respectively, which encode heavy chain variable regions having the amino acid sequences set forth as residues 20-138 of SEQ ID NO:2, residues 19-135 of SEQ ID NO:6, and residues 20-141 of SEQ ID NO:10, respectively. A nucleic acid encoding a humanized A1 heavy chain variable region comprises nucleotides 1-358 of SEQ ID NO:48. Nucleic acids encoding the A1, A2, and A3 light chain variable regions comprise nucleotides 61-381 of SEQ ID NO:3, nucleotides 67-390 of SEQ ID NO:7, and nucleotides 61-381 of SEQ ID NO:11, respectively, which encode heavy chain variable regions having the amino acid sequences set forth as residues 21-127 of SEQ ID NO:4, residues 23-130 of SEQ ID NO:8, and residues 21-127 of SEQ ID NO:12, respectively. Additional nucleic acids of the invention comprise nucleotides encoding the humanized A1, A2, and A3 variable regions depicted in FIGS. 9A-9C.

Nucleic acids of the invention may also comprise a nucleotide sequence that is substantially identical to any one of SEQ ID NOs:1, 3, 5, 7, 9, 11, and 48, including nucleotide sequences that are at least 90% identical to the variable region encoding sequences of any one of SEQ ID NOs:1, 3, 5, 7, 9, and 11, such as at least about 91% identical or least 92% identical, such as at least 93% identical, or at least 94% identical, or at least 95% identical, or at least 96% identical, or at least 97% identical, or at least 98% identical, or at least 99% identical. For example, nucleic acids of the invention may comprise (a) a nucleotide sequence that is least 98% identical to the variable region encoding sequence of SEQ ID NO:1; (b) a nucleotide sequence that is at least 97% identical to the variable region encoding sequence of SEQ ID NO:3; (c) a nucleotide sequence that is at least 98% identical to the variable region encoding sequence of SEQ ID NO:5; (d) a nucleotide sequence that is at least 98% identical to the variable region encoding sequence of SEQ ID NO:7; (e) a nucleotide sequence that is at least 99% identical to the variable region encoding sequence of SEQ ID NO:11; or (f) a nucleotide sequence that is at least 89% identical to the variable region encoding sequence of SEQ ID NO:48. Sequences are compared for maximum correspondence using a sequence comparison algorithm using the full-length variable region encoding sequence of any one of SEQ ID NOs:1, 3, 5, 7, 9, 11, 48, or nucleotide sequences encoding humanized A1, A2, and A3 variable region sequences depicted in FIGS. 9A-9H as the query sequence, as described herein below, or by visual inspection. See also Example 1 and Table 1, and Example 7 and Table 11.

Substantially identical sequences may be polymorphic sequences, i.e., alternative sequences or alleles in a population. An allelic difference may be as small as one base pair. Substantially identical sequences may also comprise mutagenized sequences, including sequences comprising silent mutations. A mutation may comprise one or more residue changes, a deletion of one or more residues, or an insertion of one or more additional residues.

Substantially identical nucleic acids are further identified as nucleic acids that hybridize specifically to or hybridize substantially to the full length of any one of SEQ ID NOs:1, 3, 5, 7, 9, 11, or 48; the full length of a variable region encoding sequence of any one of SEQ ID NOs:1, 3, 5, 7, 9, 11, or 48; or nucleotide sequences encoding humanized A1, A2, and A3 variable region sequences depicted in FIGS. 9A-9H, under stringent conditions. In the context of nucleic acid hybridization, two nucleic acid sequences being compared may be designated a probe and a target. A probe is a reference nucleic acid molecule, and a target is a test nucleic acid molecule, often found within a heterogeneous population of nucleic acid molecules. A target sequence is synonymous with a test sequence.

For hybridization studies, useful probes are complementary to or mimic at least an about 14 to 40 nucleotide sequence of a nucleic acid molecule of the present invention. Preferably, probes comprise 14 to 20 nucleotides, or even longer where desired, such as 30, 40, 50, 60, 100, 200, 300, or 500 nucleotides or up to the full length of any one of SEQ ID NOs:1, 3, 5, 7, 9, 11, or 48; the full length of a variable region encoding sequence of any one of SEQ ID NOs:1, 3, 5, 7, 9, 11, or 48; or nucleotide sequences encoding humanized A1, A2, and A3 variable region sequences depicted in FIGS. 9A-9C. Such fragments may be readily prepared, for example, by chemical synthesis of the fragment, by application of nucleic acid amplification technology, or by introducing selected sequences into recombinant vectors for recombinant production.

Specific hybridization refers to the binding, duplexing, or hybridizing of a molecule only to a particular nucleotide sequence under stringent conditions when that sequence is present in a complex nucleic acid mixture (e.g., total cellular DNA or RNA). Specific hybridization may accommodate mismatches between the probe and the target sequence depending on the stringency of the hybridization conditions.

Stringent hybridization conditions and stringent hybridization wash conditions in the context of nucleic acid hybridization experiments such as Southern and Northern blot analysis are both sequence- and environment-dependent. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes*, part I chapter 2, Elsevier, New York, N.Y. Generally, highly stringent hybridization and wash conditions are selected to be about 5° C. lower than the thermal melting point ($T_m$) for the specific sequence at a defined ionic strength and pH. Typically, under stringent conditions a probe will hybridize specifically to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.1×SSC at 65° C. An example of stringent wash conditions is 15 minutes in 0.2×SSC buffer at 65° C. See Sambrook et al., eds (1989) *Molecular Cloning: A Laboratory Manual*, Cold Spring Harbor Laboratory Press, Cold Spring Harbor, N.Y., for a description of SSC buffer. Often, a high stringency wash is preceded by a low stringency wash to remove background probe signal. An example of medium stringency wash conditions for a duplex of more than about 100 nucleotides, is 15 minutes in 1×SSC at 45° C. An example of low stringency wash for a duplex of more than about 100 nucleotides, is 15 minutes in 4× to 6×SSC at 40° C. For short probes (e.g., about 10 to 50 nucleotides), stringent conditions typically involve salt concentrations of less than about 1M $Na^+$ ion, typically about 0.01 to 1M $Na^+$ ion concentration (or other salts) at pH 7.0-8.3, and the temperature is typically at least about 30° C. Stringent conditions may also be achieved with the addition of destabilizing agents such as formamide. In general, a signal to noise ratio of 2-fold (or higher) than that observed for an unrelated probe in the particular hybridization assay indicates detection of a specific hybridization.

The following are examples of hybridization and wash conditions that may be used to identify nucleotide sequences that are substantially identical to reference nucleotide sequences of the present invention: a probe nucleotide sequence preferably hybridizes to a target nucleotide sequence in 7% sodium dodecyl sulphate (SDS), 0.5M $NaPO_4$, 1 mM EDTA at 50° C. followed by washing in 2×SSC, 0.1% SDS at 50° C.; more preferably, a probe and target sequence hybridize in 7% sodium dodecyl sulphate (SDS), 0.5M $NaPO_4$, 1 mM EDTA at 50° C. followed by washing in 1×SSC, 0.1% SDS at 50° C.; more preferably, a probe and target sequence hybridize in 7% sodium dodecyl sulphate (SDS), 0.5M $NaPO_4$, 1 mM EDTA at 50° C. followed by washing in 0.5×SSC, 0.1% SDS at 50° C.; more preferably, a probe and target sequence hybridize in 7% sodium dodecyl sulphate (SDS), 0.5M $NaPO_4$, 1 mM EDTA at 50° C. followed by washing in 0.1×SSC, 0.1% SDS at 50° C.; more preferably, a probe and target sequence hybridize in 7% sodium dodecyl sulphate (SDS), 0.5M $NaPO_4$, 1 mM EDTA at 50° C. followed by washing in 0.1×SSC, 0.1% SDS at 65° C.

A further indication that two nucleic acid sequences are substantially identical is that proteins encoded by the nucleic acids are substantially identical, share an overall three-dimensional structure, or are biologically functional equivalents. These terms are defined further herein below. Nucleic acid molecules that do not hybridize to each other under stringent conditions are still substantially identical if the corresponding proteins are substantially identical. This may occur, for example, when two nucleotide sequences comprise conservatively substituted variants as permitted by the genetic code.

Conservatively substituted variants are nucleic acid sequences having degenerate codon substitutions wherein the third position of one or more selected (or all) codons is substituted with mixed-base and/or deoxyinosine residues. See Batzer et al. (1991) *Nucleic Acids Res.* 19:5081; Ohtsuka et al. (1985) *J. Biol. Chem.* 260:2605-2608; and Rossolini et al. (1994) *Mol. Cell Probes* 8:91-98.

Nucleic acids of the invention also comprise nucleic acids complementary to any one of SEQ ID NOs: 1, 3, 5, 7, 9, 11, 48, or nucleotide sequences encoding humanized A1, A2, and A3 variable region sequences depicted in FIGS. 9A-9C, and subsequences and elongated sequences of SEQ ID NOs: 1, 3, 5, 7, 9, 11, 48, or nucleotide sequences encoding humanized A1, A2, and A3 variable region sequences depicted in FIGS. 9A-9C, and complementary sequences thereof. Complementary sequences are two nucleotide sequences that comprise antiparallel nucleotide sequences capable of pairing with one another upon formation of hydrogen bonds between base pairs. As used herein, the term complementary sequences means nucleotide sequences which are substantially complementary, as may be assessed by the same nucleotide comparison methods set forth below, or is defined as being capable of hybridizing to the nucleic acid segment in question under relatively stringent conditions such as those described herein. A particular example of a complementary nucleic acid segment is an antisense oligonucleotide.

A subsequence is a sequence of nucleic acids that comprises a part of a longer nucleic acid sequence. An exemplary subsequence is a probe, described herein above, or a primer. The term primer as used herein refers to a contiguous sequence comprising about 8 or more deoxyribonucleotides or ribonucleotides, preferably 10-20 nucleotides, and more preferably 20-30 nucleotides of a selected nucleic acid molecule. The primers of the invention encompass oligonucleotides of sufficient length and appropriate sequence so as to provide initiation of polymerization on a nucleic acid molecule of the present invention.

An elongated sequence comprises additional nucleotides (or other analogous molecules) incorporated into the nucleic acid. For example, a polymerase (e.g., a DNA polymerase) may add sequences at the 3' terminus of the nucleic acid molecule. In addition, the nucleotide sequence may be combined with other DNA sequences, such as promoters, promoter regions, enhancers, polyadenylation signals, intronic sequences, additional restriction enzyme sites, multiple cloning sites, and other coding segments. Thus, the invention also provides vectors comprising the disclosed nucleic acids, including vectors for recombinant expression, wherein a nucleic acid of the invention is operatively linked to a functional promoter. When operatively linked to a nucleic acid, a promoter is in functional combination with the nucleic acid such that the transcription of the nucleic acid is controlled and regulated by the promoter region. Vectors refer to nucleic acids capable of replication in a host cell, such as plasmids, cosmids, and viral vectors.

Nucleic acids of the present invention may be cloned, synthesized, altered, mutagenized, or combinations thereof. Standard recombinant DNA and molecular cloning techniques used to isolate nucleic acids are known in the art. Site-specific mutagenesis to create base pair changes, deletions, or small insertions is also known in the art. See e.g., Sambrook et al. (eds.) (1989) *Molecular Cloning: A Laboratory Manual*. Cold Spring Harbor Laboratory Press, Cold Spring Harbor, N.Y.; Silhavy et al. (1984) *Experiments with Gene Fusions*. Cold Spring Harbor Laboratory Press, Cold Spring Harbor, N.Y.; Glover & Hames (1995) *DNA Cloning: A Practical Approach*, 2nd ed. IRL Press at Oxford University Press, Oxford/New York; Ausubel (ed.) (1995) *Short Protocols in Molecular Biology*, 3rd ed. Wiley, New York.

II.B. Anti-5T4 Polypeptides

The present invention also provides isolated anti-5T4 polypeptides. Polypeptides and proteins each refer to a compound made up of a single chain of amino acids joined by peptide bonds. Representative heavy chain variable region polypeptides are set forth as residues 20-138 of SEQ ID NO:2, residues 19-135 of SEQ ID NO:6, residues 20-141 of SEQ ID NO:10, and residues 1-119 of SEQ ID NO:49. Representative light chain variable region polypeptides are set forth as residues 21-127 of SEQ ID NO:4, residues 23-130 of SEQ ID NO:8, and residues 21-127 of SEQ ID NO:12. Additional polypeptides of the invention comprise amino acids of the humanized A1, A2, and A3 variable regions depicted in FIGS. 9A-9C.

Additional polypeptides of the invention include heavy chain and light chain variable region polypeptides that are substantially similar to the disclosed anti-5T4 polypeptides, such as at least about 90% identical to the variable regions of SEQ ID NOs:2, 4, 6, 8, 10, 12, and 49, for example, at least about 91% identical, least 92% identical, at least 93% identical, at least 94% identical, at least 95% identical, at least 96% identical, at least 97% identical, at least 98% identical, or at least 99% identical. Sequences are compared for maximum correspondence using a sequence comparison algorithm using the full-length sequence of any one of SEQ ID NOs:2, 4, 6, 8, 10, 12, 49, or any one of the humanized A1, A2, or A3 variable regions depicted in FIGS. 9A-9C as the query sequence, or the variable region sequence thereof, or by visual inspection. The invention further encompasses polypeptides encoded by any one of the nucleic acids disclosed herein.

For example, representative polypeptides of the invention include (a) polypeptides having an amino acid sequence that is at least 85% similar to residues 20-138 of SEQ ID NO:2; (b) polypeptides having an amino acid sequence that is at least 94% similar to residues 21-127 of SEQ ID NO:4; (c) polypeptides having an amino acid sequence that is at least 86% similar to residues 19-135 of SEQ ID NO:6; (d) polypeptides having an amino acid sequence that is at least 96% similar to residues 23-130 of SEQ ID NO:8; (e) polypeptides having an amino acid sequence that is at least 91% similar to residues 20-141 of SEQ ID NO:10; (f) polypeptides having an amino acid sequence that is at least 98% similar to residues 21-127 of SEQ ID NO:12; and (g) polypeptides having an amino acid sequence that is at least 90% similar to residues 1-119 of SEQ ID NO:49. See Example 1 and Table 2, and Example 7 and Table 11.

Polypeptides of the invention may comprise naturally occurring amino acids, synthetic amino acids, genetically encoded amino acids, non-genetically encoded amino acids, and combinations thereof. Polypeptides may include both L-form and D-form amino acids.

Representative non-genetically encoded amino acids include but are not limited to 2-aminoadipic acid; 3-aminoadipic acid; 1-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; and ornithine.

Representative derivatized amino acids include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine.

The present invention also provides fragments of an anti-5T4 polypeptide of the invention, for example, fragments constituting a 5T4 antigen binding site. Polypeptide sequences that are longer than the disclosed sequences are also provided. For example, one or more amino acids may be added to the N-terminus or C-terminus of an antibody polypeptide. Such additional amino acids may be employed in a variety of applications, including but not limited to purification applications. Methods of preparing elongated proteins are known in the art.

Anti-5T4 polypeptides of the invention include proteins comprising amino acids that are conservatively substituted variants of any one of SEQ ID NOs:2, 4, 6, 8, 10, 12, or 49. A conservatively substituted variant refers to a polypeptide comprising an amino acid in which one or more residues have been conservatively substituted with a functionally similar residue.

Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

Isolated polypeptides of the invention may be purified and characterized using a variety of standard techniques that are known to the skilled artisan. See e.g., Schröder & Lübke (1965) *The Peptides*. Academic Press, New York; Bodanszky (1993) *Principles of Peptide Synthesis*, 2nd rev. ed. Springer-Verlag, Berlin/New York; Ausubel (ed.) (1995) *Short Protocols in Molecular Biology*, 3rd ed. Wiley, New York.

II.C. Nucleotide and Amino Acid Sequence Comparisons

The terms identical or percent identity in the context of two or more nucleotide or protein sequences, refer to two or more sequences or subsequences that are the same or have a specified percentage of amino acid residues or nucleotides that are the same, when compared and aligned for maximum correspondence, as measured using one of the sequence comparison algorithms disclosed herein or by visual inspection.

The term substantially identical in regards to a nucleotide or protein sequence means that a particular sequence varies from the sequence of a naturally occurring sequence by one or more deletions, substitutions, or additions, the net effect of which is to retain biological function of an anti-5T4 nucleic acid or polypeptide.

For comparison of two or more sequences, typically one sequence acts as a reference sequence to which one or more test sequences are compared. When using a sequence comparison algorithm, test and reference sequences are entered into a computer program, subsequence coordinates are designated if necessary, and sequence algorithm program parameters are selected. The sequence comparison algorithm then calculates the percent sequence identity for the designated test sequence(s) relative to the reference sequence, based on the selected program parameters.

Optimal alignment of sequences for comparison may be conducted, for example, by the local homology algorithm of Smith & Waterman (1981) *Adv. Appl. Math* 2:482-489, by the homology alignment algorithm of Needleman & Wunsch (1970) *J. Mol. Biol.* 48:443-453, by the search for similarity method of Pearson & Lipman (1988) *Proc. Natl. Acad. Sci. USA* 85:2444-2448, by computerized implementations of these algorithms (GAP, BESTFIT, FASTA, and TFASTA in the Wisconsin Genetics Software Package, Genetics Computer Group, Madison, Wis.), or by visual inspection. See generally, Ausubel (ed.) (1995) *Short Protocols in Molecular Biology*, 3rd ed. Wiley, New York.

A preferred algorithm for determining percent sequence identity and sequence similarity is the BLAST algorithm, which is described in Altschul et al. (1990) *J. Mol. Biol.* 215:403-410. Software for performing BLAST analyses is publicly available through the National Center for Biotechnology Information (web site www.ncbi.nlm.nih.gov). The BLAST algorithm parameters determine the sensitivity and speed of the alignment. For comparison of two nucleotide sequences, the BLASTn default parameters are set at W=11 (wordlength) and E=10 (expectation), and also include use of a low-complexity filter to mask residues of the query sequence having low compositional complexity. For comparison of two amino acid sequences, the BLASTp program default parameters are set at W=3 (wordlength), E=10 (expectation), use of the BLOSUM62 scoring matrix, gap costs of existence=11 and extension=1, and use of a low-complexity filter to mask residues of the query sequence having low compositional complexity. See Example 1.

III. Anti-5T4 Antibody/Drug Conjugates

The present invention further provides antibody/drug conjugates comprising an anti-5T4 antibody of the invention. Also provided are methods for preparing the antibody/drug conjugates, such that the drug is bound to the antibody either directly or indirectly. Antibody/drug conjugates of the invention have the general formula 5T4Ab(-X—W)$_m$ wherein:

5T4Ab is an anti-5T4 antibody or antibody fragment as described herein;

X is a linker that comprises a product of any reactive group that may react with an anti-5T4 antibody or antibody fragment;

W is a drug;

m is the average loading for a purified conjugation product (e.g., m such that the drug constitutes about 3-10% of the conjugate by weight); and (—X—W)$_m$ is a drug derivative.

Also provided are methods for preparing antibody/drug conjugates of the invention. As one example, an antibody/drug conjugate of the formula 5T4Ab(-X—W)$_m$ may be prepared by (a) adding the drug derivative to the anti-5T4 antibody wherein the drug is 3-10% by weight of the anti-5T4 antibody; (b) incubating the drug derivative and the anti-5T4 antibody in a non-nucleophilic, protein-compatible, buffered solution having a pH in a range from about 7 to 9 to produce an antibody/drug conjugate, wherein the solution further compromises (i) a suitable organic cosolvent, and (ii) and one or more additives comprising at least one bile acid or its salt, and wherein the incubation is conducted at a temperature ranging from about 30° C. to about 35° C. for a period of time ranging from about 15 minutes to about 24 hours; and (c) subjecting the conjugate produced in step (b) to a chromatographic separation process to separate antibody/drug conjugates with a loading in the range of 3-10% by weight drug and with low conjugated fraction (LCF) from unconjugated anti-5T4 antibody, drug derivative, and aggregated conjugates.

III.A. Drugs

A drug is any substance having biological or detectable activity, for example, therapeutic agents, detectable labels, binding agents, etc., and prodrugs, which are metabolized to an active agent in vivo. A drug may also be a drug derivative, wherein a drug has been functionalized to enable conjugation with an antibody of the invention. Generally, these types of conjugates are referred to as immunoconjugates.

Therapeutic agents are compositions that may be used to treat or prevent a condition in a subject in need thereof. Therapeutic agents useful in the invention include anti-cancer agents, i.e., agents having anti-cancer activity in 5T4-expressing cells such as cancer cells from squamous/adenomatous lung carcinoma (non-small-cell lung carcinoma), invasive breast carcinoma, colorectal carcinoma, gastric carcinoma, squamous cervical carcinoma, invasive endometrial adenocarcinoma, invasive pancreas carcinoma, ovarian carcinoma, squamous vesical carcinoma, and choriocarcinoma.

Representative therapeutic drugs include cytotoxins, radioisotopes, chemotherapeutic agents, immunomodulatory agents, anti-angiogenic agents, anti-proliferative agents, pro-apoptotic agents, and cytostatic and cytolytic enzymes (e.g., RNAses). A drug may also include a therapeutic nucleic acid, such as a gene encoding an immunomodulatory agent, an anti-angiogenic agent, an anti-proliferative agent, or a pro-apoptotic agent. These drug descriptors are not mutually exclusive, and thus a therapeutic agent may be described using one or more of the above-noted terms. For example, selected radioisotopes are also cytotoxins. Therapeutic agents may be prepared as pharmaceutically acceptable salts, acids or derivatives of any of the above. Generally, conjugates having a radioisotope as the drug are referred to as radioimmunoconjugates and those having a chemotherapeutic agent as the drug are referred to as chemoimmunoconjugates.

Examples of suitable drugs for use in immunoconjugates include the taxanes, maytansines, CC-1065 and the duocarmycins, the calicheamicins and other enediynes, and the auristatins. Other examples include the anti-folates, vinca alkaloids, and the anthracyclines. Plant toxins, other bioactive proteins, enzymes (i.e., ADEPT), radioisotopes, photosensitizers (i.e., for photodynamic therapy) can also be used in immunoconjugates. In addition, conjugates can be made using secondary carriers as the cytotoxic agent, such as liposomes or polymers, for example.

The term cytotoxin generally refers to an agent that inhibits or prevents the function of cells and/or results in destruction of cells. Representative cytotoxins include antibiotics, inhibitors of tubulin polymerization, alkylating agents that bind to and disrupt DNA, and agents that disrupt protein synthesis or the function of essential cellular proteins such as protein kinases, phosphatases, topoisomerases, enzymes, and cyclins. Representative cytotoxins include, but are not limited to, doxorubicin, daunorubicin, idarubicin, aclarubicin, zorubicin, mitoxantrone, epirubicin, carubicin, nogalamycin, menogaril, pitarubicin, valrubicin, cytarabine, gemcitabine, trifluridine, ancitabine, enocitabine, azacitidine, doxifluridine, pentostatin, broxuridine, capecitabine, cladribine, decitabine, floxuridine, fludarabine, gougerotin, puromycin, tegafur, tiazofurin, adriamycin, cisplatin, carboplatin, cyclophosphamide, dacarbazine, vinblastine, vincristine, mitoxantrone, bleomycin, mechlorethamine, prednisone, procarbazine, methotrexate, fluorouracils, etoposide, taxol, taxol analogs, platins such as cis-platin and carbo-platin, mitomycin, thiotepa, taxanes, vincristine, daunorubicin, epirubicin, actinomycin, authramycin, azaserines, bleomycins, tamoxifen, idarubicin, dolastatins/auristatins, hemiasterlins, esperamicins and maytansinoids.

In particular embodiments of the invention, a cytotoxin is an antibiotic such as a calicheamicin, also called the LL-E33288 complex, for example, gamma-calicheamicin ($\gamma_1$) or N-acetyl gamma-calicheamicin. See U.S. Pat. No. 4,970,198. Additional examples of calicheamicins suitable for use in preparing antibody/drug conjugates of the invention are disclosed in U.S. Pat. Nos. 4,671,958; 5,053,394; 5,037,651; 5,079,233; and 5,108,912, which are incorporated herein in their entirety. These compounds contain a methyltrisulfide that may be reacted with appropriate thiols to form disulfides, at the same time introducing a functional group such as a hydrazide or other functional group that is useful for conjugating calicheamicin to an anti-5T4 antibody. Disulfide analogs of calicheamicin can also be used, for example, analogs described in U.S. Pat. Nos. 5,606,040 and 5,770,710, which are incorporated herein in their entirety.

For radiotherapy applications, an anti-5T4 antibody of the invention may comprise a high energy radioisotope. The isotope may be directly bound to the antibody, for example, at a cysteine residue present in the antibody, or a chelator may be used to mediate the binding of the antibody and the radioisotope. Radioisotopes suitable for radiotherapy include but are not limited to α-emitters, β-emitters, and auger electrons. For diagnostic applications, useful radioisotopes include positron emitters and γ-emitters. An anti-5T4 antibody of the invention may further be iodinated, for example, on a tyrosine residue of the antibody, to facilitate detection or therapeutic effect of the antibody.

Representative radioisotopes that may be conjugated to an anti-5T4 antibody include $^{18}$-fluorine, $^{64}$copper, $^{65}$copper, $^{67}$gallium, $^{68}$gallium, $^{77}$bromine, $^{80m}$bromine, $^{95}$ruthenium, $^{97}$ruthenium, $^{103}$ruthenium, $^{105}$ruthenium, $^{99m}$technetium, $^{107}$mercury, mercury, $^{123}$iodine, $^{124}$iodine, $^{125}$iodine, 126iodine, $^{131}$iodine, $^{133}$ iodine, $^{111}$indium, $^{113}$indium, $^{99m}$rhenium, $^{105}$rhenium, $^{101}$rhenium, $^{186}$rhenium, $^{188}$rhenium, $^{121}$mtellurium, $^{99}$technetium, $^{122m}$tellurium, $^{125m}$tellurium, $^{165}$thulium, $^{167}$thulium, $^{168}$thulium, $^{90}$yttrium, and nitride or oxide forms derived there from. Other suitable radioisotopes include alpha emitters, such as $^{213}$bismuth, $^{213}$lead, and $^{225}$actinium.

Antibody/drug conjugates of the invention may include immunomodulators, i.e., agents that elicit an immune response, including humoral immune responses (e.g. production of antigen-specific antibodies) and cell-mediated immune responses (e.g. lymphocyte proliferation). Representative immunomodulatory agents include cytokines, xanthines, interleukins, interferons, and growth factors (e.g., TNF, CSF, GM-CSF and G-CSF), and hormones such as estrogens (diethylstilbestrol, estradiol), androgens (testosterone, HALOTESTIN® (fluoxymesterone)), progestins (MEGACE® (megestrol acetate), PROVERA® (medroxyprogesterone acetate)), and corticosteroids (prednisone, dexamethasone, hydrocortisone).

Immunomodulatory agents useful in the invention also include anti-hormones that block hormone action on tumors and immunosuppressive agents that suppress cytokine production, down-regulate self-antigen expression, or mask MHC antigens. Representative anti-hormones include anti-estrogens including, for example, tamoxifen, raloxifene, aromatase inhibiting 4(5)-imidazoles, 4-hydroxytamoxifen, trioxifene, keoxifene, LY 117018, onapnstone, and toremifene; and anti-androgens such as flutamide, nilutamide, bicalutamide, leuprolide, and goserelin; and anti-adrenal agents. Representative immunosuppressive agents include 2-amino-6-aryl-5-substituted pyrimidines, azathioprine, cyclophosphamide, bromocryptine, danazol, dapsone, glutaraldehyde, anti-idiotypic antibodies for MHC antigens and MHC fragments, cyclosporin A, steroids such as glucocorticosteroids, cytokine or cytokine receptor antagonists (e.g., anti-interferon antibodies, anti-IL10 antibodies, anti-TNFα antibodies, anti-IL2 antibodies), streptokinase, TGFβ, rapamycin, T-cell receptor, T-cell receptor fragments, and T cell receptor antibodies.

Additional drugs useful in the invention include anti-angiogenic agents that inhibit blood vessel formation, for example, farnesyltransferase inhibitors, COX-2 inhibitors, VEGF inhibitors, bFGF inhibitors, steroid sulphatase inhibitors (e.g., 2-methoxyoestradiol bis-sulphamate (2-MeOE2bisMATE)), interleukin-24, thrombospondin, metallospondin proteins, class I interferons, interleukin 12, protamine, angiostatin, laminin, endostatin, and prolactin fragments.

Anti-proliferative agents and pro-apoptotic agents include activators of PPAR-gamma (e.g., cyclopentenone prostaglandins (cyPGs)), retinoids, triterpinoids (e.g., cycloartane, lupane, ursane, oleanane, friedelane, dammarane, cucurbitacin, and limonoid triterpenoids), inhibitors of EGF receptor (e.g., HER4), rampamycin, CALCITRIOL® (1,25-dihydroxycholecalciferol (vitamin D)), aromatase inhibitors (FEMARA® (letrozone)), telomerase inhibitors, iron chelators (e.g., 3-aminopyridine-2-carboxaldehyde thiosemicarbazone (Triapine)), apoptin (viral protein 3-VP3 from chicken aneamia virus), inhibitors of Bcl-2 and Bcl-X(L), TNF-alpha, FAS ligand, TNF-related apoptosis-inducing ligand (TRAIL/Apo2L), activators of TNF-alpha/FAS ligand/TNF-related apoptosis-inducing ligand (TRAIL/Apo2L) signaling, and inhibitors of PI3K-Akt survival pathway signaling (e.g., UCN-01 and geldanamycin).

Representative chemotherapeutic agents include alkylating agents such as thiotepa and cyclosphosphamide; alkyl sulfonates such as busulfan, improsulfan and piposulfan; aziidines such as benzodopa, carboquone, meturedopa, and uredopa; ethylenimines and methylamelamines including altretamine, triethylenemelamine, triethylenephosphoramide, triethylenethiophosphoramide and trimethylolomelamine; nitrogen mustards such as chlorambucil, chlornaphazine, cholophosphamide, estramustine, ifosfamide, mechiorethamine, mechiorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-EU; androgens such as calusterone, dromostanolone propionate, epitiostanol, mepitiostane, testolactone; anti-adrenal such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2, 2', 2'-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g. paclitaxel (TAXOL®, Bristol-Myers Squibb Oncology of Princeton, N.J.) and doxetaxel (TAXOTERE®, Rhone-Poulenc Rorer of Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; and capecitabine.

Additional therapeutic agents that may be conjugated to anti-5T4 antibodies and used in accordance with the therapeutic methods of the present invention include photosensitizing agents (U.S. Patent Publication No. 2002/0197262 and U.S. Pat. No. 5,952,329) for photodynamic therapy; magnetic particles for thermotherapy (U.S. Patent Publication No. 2003/0032995); binding agents, such as peptides, ligands, cell adhesion ligands, etc., and prodrugs such as phosphate-containing prodrugs, thiophosphate-containing prodrugs, sulfate containing prodrugs, peptide containing prodrugs, β-lactam-containing prodrugs, substituted phenoxyacetamide-containing prodrugs or substituted phenylacetamide-containing prodrugs, 5-fluorocytosine and other 5-fluorouridine prodrugs that may be converted to the more active cytotoxic free drug.

For diagnostic methods using anti-5T4 antibodies, a drug may comprise a detectable label used to detect the presence of 5T4-expressing cells in vitro or in vivo. Radioisotopes that are detectable in vivo, such as those labels that are detectable using scintigraphy, magnetic resonance imaging, or ultrasound, may be used in clinical diagnostic applications. Useful scintigraphic labels include positron emitters and γ-emitters. Representative contrast agents for magnetic source imaging are paramagnetic or superparamagnetic ions (e.g., iron, copper, manganese, chromium, erbium, europium, dysprosium, holmium and gadolinium), iron oxide particles, and water soluble contrast agents. For ultrasonic detection, gases or liquids may be entrapped in porous inorganic particles that are released as microbubble contrast agents. For in vitro detection, useful detectable labels include fluorophores, detectable epitopes or binding agents, and radioactive labels.

III.B. Linker Molecules

Drugs are conjugated to chimeric and humanized anti-5T4 antibodies of the invention either directly or indirectly via a linker molecule. The linker molecule may be stable or hydrolyzable, whereby it is released following cellular entry. The major mechanisms by which the drug is cleaved from the antibody include hydrolysis in the acidic pH of the lysosomes (hydrazones, acetals, and cis-aconitate-like amides), peptide cleavage by lysosomal enzymes (the cathepsins and other lysosomal enzymes), and reduction of disulfides. As a result of these varying mechanisms for cleavage, mechanisms of linking the drug to the antibody also vary widely and any suitable linker can be used. Preferably, the conjugation method produces a sample with minimal low conjugate fraction (LCF, the fraction of mostly unconjugated antibody), i.e., less than about 10%.

One example of a suitable conjugation procedure relies on the conjugation of hydrazides and other nucleophiles to the aldehydes generated by oxidation of the carbohydrates that naturally occur on antibodies. Hydrazone-containing conjugates can be made with introduced carbonyl groups that provide the desired drug-release properties. Conjugates can also be made with a linker that has a disulfide at one end, an alkyl chain in the middle, and a hydrazine derivative at the other end. The anthracyclines are one example of cytotoxins that can be conjugated to antibodies using this technology.

Linkers containing functional groups other than hydrazones have the potential to be cleaved in the acidic milieu of the lysosomes. For example, conjugates can be made from thiol-reactive linkers that contain a site other than a hydrazone that is cleavable intracellularly, such as esters, amides, and acetals/ketals. Camptothecin is one cytotoxic agent that can be conjugated using these linkers. Ketals made from a 5 to 7-member ring ketone and that has one of the oxygens attached to the cytotoxic agent and the other to a linker for antibody attachment also can be used. The anthracyclines are also an example of a suitable cytotoxin for use with these linkers.

Another example of a class of pH sensitive linkers are the cis-aconitates, which have a carboxylic acid juxtaposed to an amide bond. The carboxylic acid accelerates amide hydrolysis in the acidic lysosomes. Linkers that achieve a similar type of hydrolysis rate acceleration with several other types of structures can also be used. The maytansinoids are an example of a cytotoxin that can be conjugated with linkers attached at C-9.

Another potential release method for drug conjugates is the enzymatic hydrolysis of peptides by the lysosomal enzymes. In on example, a peptide is attached via an amide bond to para-aminobenzyl alcohol and then a carbamate or carbonate is made between the benzyl alcohol and the cytotoxic agent. Cleavage of the peptide leads to the collapse, or self-immolation, of the aminobenzyl carbamate or carbonate. The cytotoxic agents exemplified with this strategy include anthracyclines, taxanes, mitomycin C, and the auristatins. In one example, a phenol can also be released by collapse of the linker instead of the carbamate. In another variation, disulfide reduction is used to initiate the collapse of a para-mercapto-benzyl carbamate or carbonate.

Many of the cytotoxic agents conjugated to antibodies have little, if any, solubility in water and that can limit drug loading on the conjugate due to aggregation of the conjugate. One approach to overcoming this is to add solubilizing groups to the linker. Conjugates made with a linker consisting of PEG and a dipeptide can been used, including those having a PEG di-acid, thiol-acid, or maleimide-acid attached to the antibody, a dipeptide spacer, and an amide bond to the amine of an anthracycline or a duocarmycin analogue. Another example is a conjugate prepared with a PEG-containing linker disulfide bonded to a cytotoxic agent and amide bonded to an antibody. Approaches that incorporate PEG groups may be beneficial in overcoming aggregation and limits in drug loading.

Representative linkers preferred for preparation of antibody/drug conjugates of the invention include linkers of the formula:

(CO-Alk$^1$-Sp$^1$-Ar-Sp$^2$-Alk$^2$-C(Z$^1$)=Q-Sp)

wherein

Alk$^1$ and Alk$^2$ are independently a bond or branched or unbranched ($C_1$-$C_{10}$) alkylene chain;

Sp$^1$ is a bond, —S—, —O—, —CONH—, —NHCO—, —NR'—, —N($CH_2CH_2$)$_2$N—, or —X—Ar'-Y—($CH_2$)$_n$—Z wherein X, Y, and Z are independently a bond, —N'—, —S—, or —O—, with the proviso that when n=0, then at least one of Y and Z must be a bond and Ar' is 1,2-, 1,3-, or 1,4-phenylene optionally substituted with one, two, or three groups of ($C_1$-$C_5$) alkyl, ($C_1$-$C_4$) alkoxy, ($C_1$-$C_4$) thioalkoxy, halogen, nitro, —COOR', —CONHR', —($CH_2$)$_n$COOR', —S($CH_2$)$_n$COOR', —O($CH_2$)$_n$CONHR', or —S($CH_2$)$_n$CONHR', with the proviso that when Alk$^1$ is a bond, Sp$^1$ is a bond;

n is an integer from 0 to 5;

R' is a branched or unbranched ($C_1$-$C_5$) chain optionally substituted by one or two groups of —OH, ($C_1$-$C_4$) alkoxy, ($C_1$-$C_4$) thioalkoxy, halogen, nitro, ($C_1$-$C_3$) dialkylamino, or ($C_1$-$C_3$) trialkylammonium-A$^-$ where A$^-$ is a pharmaceutically acceptable anion completing a salt;

Ar is 1,2-, 1,3-, or 1,4-phenylene optionally substituted with one, two, or three groups of ($C_1$-$C_6$) alkyl, ($C_1$-$C_5$) alkoxy, ($C_1$-$C_4$) thioalkoxy, halogen, nitro, —COOR', —CONHR', —O($CH_2$)$_n$COOR', —S($CH_2$)$_n$COOR', —O($CH_2$)$_n$CONHR', or —S($CH_2$)$_n$CONHR' wherein n and R' are as hereinbefore defined or a 1,2-, 1,3-, 1,4-, 1,5-, 1,6-, 1,7-, 1,8-, 2,3-, 2,6-, or 2,7-naphthylidene or

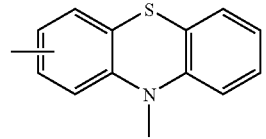

with each naphthylidene or phenothiazine optionally substituted with one, two, three, or four groups of ($C_1$-$C_6$) alkyl, ($C_1$-$C_5$) alkoxy, ($C_1$-$C_4$) thioalkoxy, halogen, nitro, —COOR', —CONHR', —O($CH_2$)$_n$COOR', —S($CH_2$)$_n$COOR', or —S($CH_2$)$_n$CONHR' wherein n and R' are as defined above, with the proviso that when Ar is phenothiazine, Sp$^1$ is a bond only connected to nitrogen;

Sp$^2$ is a bond, —S—, or —O—, with the proviso that when Alk$^2$ is a bond, Sp$^2$ is a bond;

Z$^1$ is H, ($C_1$-$C_5$) alkyl, or phenyl optionally substituted with one, two, or three groups of ($C_1$-$C_5$) alkyl, ($C_1$-$C_5$) alkoxy, ($C_1$-$C_4$) thioalkoxy, halogen, nitro, —COOR', —ONHR', —O($CH_2$)$_n$COOR', —S($CH_2$)$_n$COOR', —O($CH_2$)$_n$CONHR', or —S($CH_2$)$_n$CONHR' wherein n and R' are as defined above;

Sp is a straight or branched-chain divalent or trivalent ($C_1$-$C_{18}$) radical, divalent or trivalent aryl or heteroaryl radical, divalent or trivalent ($C_3$-$C_{18}$) cycloalkyl or heterocycloalkyl radical, divalent or trivalent aryl- or heteroaryl-aryl ($C_1$-$C_{18}$) radical, divalent or trivalent cycloalkyl- or heterocycloalkyl-alkyl ($C_1$-$C_{18}$) radical or divalent or trivalent ($C_2$-$C_{18}$) unsaturated alkyl radical, wherein heteroaryl is preferably furyl, thienyl, N-methylpyrrolyl, pyridinyl, N-methylimidazolyl, oxazolyl, pyrimidinyl, quinolyl, isoquinolyl, N-methylcarbazoyl, aminocourmarinyl, or phenazinyl and wherein if Sp is a trivalent radical, Sp may be additionally substituted by lower ($C_1$-$C_5$) dialkylamino, lower ($C_1$-$C_5$) alkoxy, hydroxy, or lower ($C_1$-$C_5$) alkylthio groups; and Q is =NHNCO—, =NHNCS—, =NHNCONH—, =NHNCSNH—, or =NHO—.

Preferably, Alk$^1$ is a branched or unbranched ($C_1$-$C_{10}$) alkylene chain; Sp' is a bond, —S—, —O—, —CONH—, —NHCO—, or —NR' wherein R' is as hereinbefore defined, with the proviso that when Alk$^1$ is a bond, Sp$^1$ is a bond;

Ar is 1,2-, 1,3-, or 1,4-phenylene optionally substituted with one, two, or three groups of ($C_1$-$C_6$) alkyl, ($C_1$-$C_5$) alkoxy, ($C_1$-$C_4$) thioalkoxy, halogen, nitro, —COOR', —CONHR', —O($CH_2$)$_n$COOR', —S($CH_2$)$_n$COOR', —O($CH_2$)$_n$CONHR', or —S($CH_2$)$_n$CONHR' wherein n and R' are as hereinbefore defined, or Ar is a 1,2-, 1,3-, 1,4-, 1,5-, 1,6-, 1,7-, 1,8-, 2,3-, 2,6-, or 2,7-naphthylidene each optionally substituted with one, two, three, or four groups of ($C_1$-$C_6$) alkyl, ($C_1$-$C_5$) alkoxy, ($C_1$-$C_4$) thioalkoxy, halogen, nitro, —COOR', —CONHR', —O($CH_2$)$_n$COOR', —S($CH_2$)$_n$COOR', —O($CH_2$)$_n$CONHR', or —S($CH_2$)$_n$CONHR'.

Z$^1$ is ($C_1$-$C_5$) alkyl, or phenyl optionally substituted with one, two, or three groups of ($C_1$-$C_5$) alkyl, ($C_1$-$C_4$) alkoxy, ($C_1$-$C_4$) thioalkoxy, halogen, nitro, —COOR', —CONHR', —O($CH_2$)$_n$COOR', —S($CH_2$)$_n$COOR', —O($CH_2$)$_n$CONHR', or —S($CH_2$)$_n$CONHR'; Alk$^2$ and Sp$^2$ are together a bond; and Sp and Q are as immediately defined above.

U.S. Pat. No. 5,773,001, incorporated herein in its entirety, discloses linkers that may be used with nucleophilic drugs, particularly hydrazides and related nucleophiles, prepared from the calicheamicins. These linkers are especially useful in those cases where better activity is obtained when the linkage formed between the drug and the linker is hydrolyzable. These linkers contain two functional groups, including (1) a group for reaction with an antibody (e.g., carboxylic acid), and (2) a carbonyl group (e.g., an aldehyde or a ketone) for reaction with a drug. The carbonyl groups may react with a hydrazide group on the drug to form a hydrazone linkage. This linkage is hydrolyzable, allowing for release of the therapeutic agent from the conjugate after binding to the target cells.

As one example, an anti-5T4 antibody may be conjugated to a cytotoxic drug by (1) adding the cytotoxic drug derivative to the anti-5T4 antibody wherein the cytotoxic drug is 4.5%-11% by weight of the proteinaceous carrier; (2) incubating the cytotoxic drug derivative and anti-5T4 antibody in a non-nucleophilic, protein-compatible, buffered solution having a pH in the range from about 7 to 9 to produce a monomeric cytotoxic drug/antibody conjugate, wherein the solution further comprises (a) a suitable organic cosolvent, and (b) an additive comprising at least one $C_6$-$C_{18}$ carboxylic acid or its salt, and wherein the incubation is conducted at a temperature ranging from about 30° C. to about 35° C. for a period of time ranging from about 15 minutes to 24 hours; and (3) subjecting the conjugate produced in step (2) to a chromatographic separation process to separate monomeric conjugates with a loading in the range of 3% to 10% by weight cytotoxic drug and with low conjugated fraction (LCF) below 10 percent from unconjugated antibody, cytotoxic drug derivative, and aggregated conjugates.

The chromatographic separation of step (3) can include processes such as size exclusion chromatography (SEC), ultrafiltration/diafiltration, HPLC, FPLC, or Sephacryl S-200 chromatography. The chromatographic separation may also be accomplished by hydrophobic interaction chromatography (HIC) using Phenyl Sepharose 6 Fast Flow chromatographic medium, Butyl Sepharose 4 Fast Flow chromatographic medium, Octyl Sepharose 4 Fast Flow chromatographic medium, Toyopearl Ether-650M chromatographic medium, Macro-Prep methyl HIC medium or Macro-Prep t-Butyl HIC medium.

Representative methods for preparing anti-5T4 antibody/drug conjugates include those described for preparation of CMC-544 in co-pending published U.S. Patent Application Publication No. 2004-082764A1 and U.S. patent application Ser. No. 10/699,874, which are incorporated herein in their entirety. Conjugation may be performed using the following conditions: 10 mg/ml antibody, 8.5% (w/w) calicheamicin derivative, 37.5 mM sodium decanoate, 9% (v/v) ethanol, 50 mM HEPES (N-(2-Hydroxyethyl)piperazine-N'-(4-butane-sulfonic acid)), pH 8.5, 32° C., 1 hour. Hydrophobic interaction chromatography (HIC) may be performed using a butyl sepharose FF resin, 0.65 M potassium phosphate loading buffer, 0.49 M potassium phosphate wash buffer, and 4 mM potassium phosphate elution buffer. Buffer exchange may be accomplished by size exclusion chromatography, ultrafiltration/diafiltration, or other suitable means. The antibody/drug conjugate may be formulated in 1.5% Dextran-40, 0.9% sucrose, 0.01% TWEEN®-80, 20 mM Tris/50 mM NaCl, pH 8.0. An alternative formulation solution containing 5% sucrose, 0.01% TWEEN®-80, 20 mM Tris/10 mM NaCl, pH 8.0 may also be used. Lyophilization cycles are adjusted based on the formulation. The concentration of the formulated bulk may be 0.5 mg conjugate/ml. Each may vial contain 1 mg of conjugate, i.e., 2 ml fill. Other fill volumes may be prepared as desired, e.g., 5 ml fill.

Other representative methods include those described for CMD-193, also described in U.S. Patent Application Publication No. 20060002942. Conjugation may be performed using the following conditions: 10 mg/ml antibody, 7% (w/w) calicheamicin derivative, 10 mM deoxycholate, 50 mM HEPBS (N-(2-Hydroxyethyl)piperazine-N'-(4-butane-sulfonic acid)), 9% (v/v) ethanol, pH 8.2, 32° C., 1 hour. The reaction may be diluted 10-fold with 0.66 M potassium phosphate pH 8.56, and HIC may be performed using a butyl sepharose FF resin, 0.60 M potassium phosphate loading buffer and wash buffer, and 20 mM Tris/25 mM NaCl elution buffer. Buffer exchange may be accomplished using ultrafiltration/diafiltration with a regenerated cellulose membrane. The conjugate may be diafiltered against 20 mM Tris/10 mM NaCl pH 8.0 (10 diavolumes). The antibody/drug conjugate may be formulated in 5% sucrose, 0.01% TWEEN®-80, 20 mM Tris/10 mM NaCl, pH 8.0. The concentration of the bulk conjugate after formulation may be 1 mg/ml, and the vial fill may be 5 mg/vial, i.e., 5 ml fill, or other fill volumes may be prepared as desired.

In a particular embodiment of the invention, the linker employed is 4-(4-acetylphenoxy) butanoic acid (AcBut). Antibody/drug conjugates are prepared by reacting β-calicheamicin, γ-calicheamicin or N-acetyl γ-calicheamicin, or derivatives thereof, with 3-mercapto-3-methyl butanoyl hydrazide, the AcBut linker, and an anti-5T4 antibody of the invention. See e.g., U.S. Pat. No. 5,773,001. This linker produces conjugates that are substantially stable in circulation, releasing an estimated 2% of the NAc-gamma DMH per day, and which release the NAc-gamma DMH readily in the acidic lysosomes. In other embodiments of the invention, antibody/drug conjugates are prepared using 3-acetylphenyl acidic acid (AcPac) or 4-mercapto-4-methyl-pentanoic acid (Amide) as the linker molecule.

Representative linkers useful for conjugation of radioisotopes include diethylenetriamine pentaacetate (DTPA)-isothiocyanate, succinimidyl 6-hydrazinium nicotinate hydrochloride (SHNH), and hexamethylpropylene amine oxime (HMPAO) (Bakker et al. (1990) *J. Nucl. Med.* 31: 1501-1509, Chattopadhyay et al. (2001) *Nucl. Med. Biol.* 28: 741-744, Dewanjee et al. (1994) *J. Nucl. Med.* 35: 1054-63, Krenning et al. (1989) *Lancet* 1: 242-244, Sagiuchi et al. (2001) *Ann. Nucl. Med.* 15: 267-270); U.S. Pat. No. 6,024,938). Alternatively, a targeting molecule may be derivatized so that a radioisotope may be bound directly to it (Yoo et al. (1997) *J. Nucl. Med.* 38: 294-300). Iodination methods are also known in the art, and representative protocols may be found, for example, in Krenning et al. (1989) *Lancet* 1:242-4 and in Bakker et al. (1990) *J. Nucl. Med.* 31:1501-9.

To further increase the number of drug molecules per antibody/drug conjugate, the drug may be conjugated to polyethylene glycol (PEG), including straight or branched polyethylene glycol polymers and monomers. A PEG monomer is of the formula: —($CH_2CH_2O$)—. Drugs and/or peptide analogs may be bound to PEG directly or indirectly, i.e. through appropriate spacer groups such as sugars. A PEG/antibody/drug composition may also include additional lipophilic and/or hydrophilic moieties to facilitate drug stability and delivery to a target site in vivo. Representative methods for preparing PEG-containing compositions may be found in U.S. Pat. Nos. 6,461,603; 6,309,633; and 5,648,095, among other places.

For example, to increase the amount of calicheamicin in antibody-calicheamicin conjugates, the antibody is conjugated to PEG prior to conjugation with calicheamicin, for example, using PEG-SPA, PEG-SBA, or PEG-bis-maleimide. Antibody/drug conjugates prepared using PEG may show reduced binding affinity for the target antigen, but are still effective as a result of increased drug load. Additives such as deoxycholate and decanoate may be used to produce an antibody/calicheamicin conjugates with low levels of unconjugated antibody and low levels of aggregate.

The hydrophobic nature of many drugs, including calicheamicins, may results in aggregation of antibody/drug conjugates. To produce monomeric antibody/drug conjugates with higher drug loading/yield and decreased aggregation, the conjugation reaction may be performed in a non-nucleophilic, protein-compatible, buffered solution containing (i) propylene glycol as a cosolvent and (ii) an additive comprising at least one $C_6$-$C_{18}$ carboxylic acid. Useful acids include $C_7$ to $C_{12}$ acids, such as octanoic acid or caprylic acid, or its salts. Other protein-compatible organic cosolvents other than propylene glycol, such as ethylene glycol, ethanol, DMF, DMSO, etc., may also be used. Some or all of the organic cosolvent is used to transfer the drug into the conjugation mixture. Useful buffers for the preparation of antibody/drug conjugates using N-hydroxysuccinimide (OSu) esters or other comparably activated esters include phosphate-buffered saline (PBS) and N-2-hydroxyethyl piperazine-N'-2-ethanesulfonic acid (HEPES buffer). The buffered solution used in conjugation reactions should substantially lack free amines and nucleophiles. As another approach, the conjugation reactions may be performed in a non-nucleophilic, protein-compatible, buffered solution containing t-butanol without the additional additives. See e.g., U.S. Pat. Nos. 5,712,374 and 5,714,586. Additional methods for conjugation and calicheamicin-containing conjugates are described in U.S. Pat. Nos. 5,739,116 and 5,877,296.

Optimal reaction conditions for formation of a monomeric conjugate may be empirically determined by variation of reaction variables such as temperature, pH, calicheamicin derivative input, and additive concentration. Representative amounts of propylene glycol range from 10% to 60%, for example, 10% to 40%, or about 30% by volume of the total solution. Representative amounts of an additive comprising at least one $C_6$-$C_{18}$ carboxylic acid or its salt range from 20 mM to 100 mM, such as from 40 mM to 90 mM, or about 60 mM to 90 mM. The concentration of the $C_6$-$C_{18}$ carboxylic acid or its salt may be increased to 150-300 mM and the cosolvent dropped to 1% to 10%. In representative embodiments of the invention, the carboxylic acid is octanoic acid, decanoic acid, or the corresponding salts. For example, 200 mM caprylic acid may be used with 5% propylene glycol or ethanol. The conjugation reaction may be performed at slightly elevated temperature (30-35° C.) and pH (8.2-8.7). The concentration of antibody may range from 1 to 15 mg/ml and the concentration of a calicheamicin derivative, e.g., N-Acetyl gamma-calicheamicin DMH AcBut OSu ester may range from about 4.5% to 11% by weight of the antibody. Conditions suitable for conjugation of other drugs may be determined by those skilled in the art without undue experimentation.

III.C. Purification of Antibody/Drug Conjugates

Following conjugation, the monomeric conjugates may be separated from unconjugated reactants and/or aggregated forms of the conjugates by conventional methods, for example, size exclusion chromatography (SEC), hydrophobic interaction chromatography (HIC), ion exchange chromatography (IEC), or chromatofocusing (CF). The purified conjugates are monomeric, and usually contain from 3% to 10% drug by weight. Antibody/drug conjugates may also be purified using hydrophobic interaction chromatography (HIC), which offers some advantages over SEC including (1) a capability to efficiently reduce the LCF content as well as aggregate; (2) accommodation of large reaction volumes; and (3) minimal dilution of the product. High-capacity HIC media suitable for production scale use include Phenyl Sepharose 6 Fast Flow chromatographic medium, Butyl Sepharose 4 Fast Flow chromatographic medium, Octyl Sepharose 4 Fast Flow chromatographic medium, Toyopearl Ether-650M chromatographic medium, Macro-Prep methyl HIC medium or Macro-Prep t-Butyl HIC medium. Ultrafiltration/diafiltration may also be used for buffer exchange.

In a representative purification process, multiple steps are performed, including a centrifuge cell removal step, a Protein A affinity capture step followed by one or two orthogonal chromatographic polishing steps, a virus filtration step, and a tangential flow filtration step for concentration and formulation. The purification process preferably yields product with less than 5% aggregate, less than 20 ppm Protein A, less than 50 ppm host cell protein, and overall recovery of greater than 50%.

A typical anti-5T4/calicheamicin preparation contains predominantly (~95%) conjugated antibody containing 5-7 moles calicheamicin per mole antibody. The conjugate has been reproducibly prepared at the laboratory scale (10-200 mg). Drug loading, which is expressed as µg calicheamicin/mg monoclonal antibody, is determined by dividing the calicheamicin concentration (µg/mL) by the antibody concentration (mg/mL). These values are determined by measuring the UV absorbance of the conjugate solution at 280 nm and 310 nm. It is important to note that this is an average loading and that the actual loading is a quasi-gaussian distribution centered on the average loading value, i.e., some of the antibody is loaded higher than average and some of the antibody is loaded lower than the average. Unconjugated antibody (low conjugated fraction), which can be measured using analytical HIC-HPLC (hydrophobic interaction high-performance liquid chromatography), is the population of antibody that has little or no conjugated calicheamicin. This value is a measure of calicheamicin distribution on the antibody and does not generally affect the amount of calicheamicin dosed. Unconjugated calicheamicin, which can be measured using ELISA, refers to the amount of calicheamicin that is not conjugated to the antibody and is expressed in terms of percent of total calicheamicin. Drug-loading assays do not differentiate between unconjugated and conjugated calicheamicin. The amount of unconjugated calicheamicin is undetectable or negligible when using drug-loading assays, and therefore these assays effectively measure the amount of conjugated calicheamicin.

Analytical methods can be used to assay for release and stability testing of humanized anti-5T4 calicheamicin conjugates. The conjugates can be evaluated for identity (IEF), strength (total protein and total calicheamicin loading), purity (unconjugated calicheamicin, low conjugated antibody, aggregate content and SDS-PAGE Reduced), and immunoaffinity (antigen binding ELISA). Additional assays known to those of skill in the art can be used. Using these assays, batch-to-batch consistency can be maintained in commercial manufacture.

III.D. Pharmacokinetics of Antibody/Drug Conjugates

The pharmacokinetics of 5T4-targeted immunoconjugates can be evaluated and compared to the pharmacokinetics of unconjugated calicheamicin in various animals. For example, this can be done following a single intravenous bolus administration in female nude mice, male Sprague-Dawley rats, and female cynomologus monkeys. Pharmacokinetics of an anti-5T4 antibody are generally characterized by low clearance, low volume of distribution, and long apparent terminal half-life in various species. The serum concentrations of unconjugated calicheamicin derivatives are expected to be below the quantification limit. The toxicity profile for these conjugates in single-dose toxicity ranging studies is expected to be similar to that obtained for other antibody/calicheamicin conjugates at comparable doses.

IV. Functional Assays for Characterization of Anti-5T4 Antibodies and Antibody/Drug Conjugates The present invention further discloses in vitro and in vivo assays to characterize activities of an anti-5T4 antibody, including 5T4 binding activity, cellular internalization following binding to 5T4 antigen presented on a cell surface, and targeting to 5T4-expressing cells in a subject. When conjugated to a cytotoxin, the disclosed antibodies of the invention may elicit anti-cancer activity, including inhibition of growth of 5T4-expressing cancer cells and/or induction of cell death in 5T4-expressing cells. Anti-5T4 antibodies of the invention may comprise one or more of the foregoing activities.

Techniques for detecting binding of anti-5T4 antibodies to 5T4 antigen are known in the art, including for example, BIACORE® assays as described in Example 2. Additional representative techniques include centrifugation, affinity chromatography and other immunochemical methods. See e.g., Manson (1992) *Immunochemical Protocols*, Humana Press, Totowa, N.J., United States of America; Ishikawa (1999) *Ultrasensitive and Rapid Enzyme Immunoassay*, Elsevier, Amsterdam/New York. Antigen binding assays may be performed using isolated 5T4 antigen or 5T4-expressing cells. See Example 2.

The binding specificity of anti-5T4 antibodies may be further described by definition of a binding epitope, i.e., identification of residues, including nonadjacent residues that participate in antigen binding, and/or definition of residues that influence antigen binding. See Examples 4-5.

Internalization of anti-5T4 antibodies and antibody/drug conjugates by 5T4-expressing cells may be assayed by observing the amount of antibodies or conjugates bound to the surface of the 5T4-expressing cells over time. Representative techniques for assessing membrane localization of antibodies and antibody/drug conjugates are described in Example 3.

Functional assays also include methods for assessing anti-cancer activity of antibody/drug conjugates, for example, an ability to destroy existing cancer cells, or to delay or prevent growth of cancer cells. Cancers targeted by antibody/drug conjugates of the invention include both primary and metastasized tumors and carcinomas of any tissue in a subject, including carcinomas and hematopoietic malignancies such as leukemias and lymphomas.

Anti-5T4 antibodies having growth inhibitory activity can eliminate 5T4-expressing cells or to prevent or reduce proliferation of 5T4-expressing cells. Representative methods for rapid in vitro assessment of cell growth inhibition are described in Jones et al. (2001) *J. Immunol. Methods* 254:85-98.

Anti-5T4 antibodies may also comprise an ability to induce cell death, for example, programmed cell death characterized by nuclear DNA degradation, nuclear degeneration and condensation, loss of membrane integrity, and phagocytosis. Representative assays to assess cell are described in Hoves et al. (2003) *Methods* 31:127-34; Peng et al. (2002) *Chin. Med. Sci. J.* 17:17-21; Yasuhara et al. (2003) *J. Histochem. Cytochem.* 51:873-885.

For example, to assess the cytotoxicity of anti-5T4 antibody/calicheamicin conjugates in vitro, MDAMB435/5T4 cells (human breast carcinoma cells overexpressing human 5T4 antigen) and MDAMB435/neo cells (control cells) are cultured in the presence of antibody-calicheamicin conjugates or free calicheamicin, essentially as described by Boghaert et al. (2004), *Clin. Cancer Res.*, 10: 4538-4549. The cytotoxicity of each agent is reported as ED50 (ng/ml), which is the amount of calicheamicin given as conjugate or as free drug that causes 50% reduction of a cell culture relative to an untreated control. The number of cells in culture is determined using a vital dye (MTS) following drug exposure. See also Example 6.

The cytotoxicity of antibody/calicheamicin conjugates may also be assessed using MDAMB435/5T4 and MDAMB435/neo cells cultured in a manner suitable for spheroid growth. Cells are cultured in the presence of antibody/calicheamicin conjugates or free calicheamicin, and following drug exposure, the dimensions of each spheroid was determined. The efficiency of each of agent in inhibiting spheroid growth is reported as ED50 (ng/ml), i.e., the amount of calicheamicin given as conjugate or as free drug that causes 50% inhibition of spheroid growth relative to an untreated control. See Example 6.

To assess the cytotoxicity of anti-5T4 antibody/calicheamicin conjugates in vivo, tumors are prepared in nude mice by subcutaneous injection of MDAMB435/5T4 cells (human breast carcinoma cells overexpressing human 5T4 antigen), NCI-H157 cells (human non-small cell lung cancer cells), PC14PE6 cells (human non-small cell lung cancer cells), or N87 cells (human gastric carcinoma cells). Antibody/calicheamicin conjugates and control compounds are administered to tumor-bearing mice, for example, by intraperitoneal injection in a total of 3 doses given at 4-day intervals, e.g., on days 1, 5, and 9. Measurable therapeutic outcomes include inhibition of tumor cell growth.

To further assess the targeting ability of anti-5T4 antibody/calicheamicin conjugates, an orthotopic model for non-small cell and small cell cancer may be used, essentially as described by Onn et al. (2003) *Clin. Cancer Res.* 9(15):5532-5539. In brief, human lung adenocarcinoma (PC14PE6) cells are injected into tail veins of nude mice, which then migrate to form tumors in lung. Tumors may appear as solid nodules in the lung parenchyma and cause hemorrhagic pleural effusions containing suspended tumor cells. Control compounds and antibody/calicheamicin conjugates are administered to tumor-bearing mice, for example, by intraperitoneal injection beginning at 6 days after injection of tumor cells for a total of 3 doses given at 4-day intervals, e.g., on days 6, 10, and 14. Measurable therapeutic outcomes include reduced pleural effusions and increased survival.

V. Uses of Anti-5T4 Antibodies and Antibody/Drug Conjugates

The anti-5T4 antibodies and antibody/drug conjugates of the invention are useful both in vitro and in vivo for applications related to 5T4-expressing cells. Cancers expressing 5T4 include squamous/adenomatous lung carcinoma (non-small-cell lung carcinoma), invasive breast carcinoma, colorectal carcinoma, gastric carcinoma, squamous cervical carcinoma, invasive endometrial adenocarcinoma, invasive pancreas carcinoma, ovarian carcinoma, squamous vesical carcinoma, and choriocarcinoma. 5T4 is detected at high levels on carcinomas of bronchi, breast, colon, rectum, stomach, cervix, endometrium, pancreas, ovaria, chorium, and seminal vesicles.

V.A. In Vitro Applications

The present invention provides in vitro methods using anti-5T4 antibodies. For example, the disclosed antibodies may be used, either alone or in combination with cytotoxic agents or other drugs to specifically bind 5T4-positive cancer cells to deplete such cells from a cell sample. Methods are also provided for inducing apoptosis and/or inhibition of cell proliferation via contacting 5T4-expressing cells with an antibody/drug conjugate comprising an anti-5T4 antibody conjugated to a cytotoxin. Representative in vitro methods are described herein above under the heading of "Functional Assays for Characterization of Anti-5T4 Antibodies and Antibody/Drug Conjugates."

Anti-5T4 antibodies of the invention also have utility in the detection of 5T4-positive cells in vitro based on their ability to specifically bind 5T4 antigen. A method for detecting 5T4-expressing cells may comprise: (a) preparing a biological sample comprising cells; (b) contacting an anti-5T4 antibody with the biological sample in vitro; and (c) detecting binding of anti-5T4 antibody. To facilitate detection, the antibody may be conjugated to a label.

V.B. In Vivo Detection and Diagnosis

Anti-5T4 antibodies of the invention may also be used for in vivo detection methods, for example, as useful for diagnosis, to provide intraoperative assistance, or for dose determination. Following administration of a labeled anti-5T4 antibody to a subject, and after a time sufficient for binding, the biodistribution of 5T4-expressing cells bound by the antibody may be visualized. The disclosed diagnostic methods may be used in combination with treatment methods. In addition, anti-5T4 antibodies of the invention may be administered for the dual purpose of detection and therapy.

Representative non-invasive detection methods include scintigraphy (e.g., SPECT (Single Photon Emission Computed Tomography), PET (Positron Emission Tomography), gamma camera imaging, and rectilinear scanning), magnetic resonance imaging (e.g., convention magnetic resonance imaging, magnetization transfer imaging (MTI), proton magnetic resonance spectroscopy (MRS), diffusion-weighted imaging (DWI) and functional MR imaging (fMRI)), and ultrasound.

V.C. Therapeutic Applications

The present invention further relates to methods and compositions useful for inducing cytolysis of 5T4-expressing cancer cells in a subject. The anti-5T4 antibody/drug conjugates of the invention are useful for inhibiting growth of cancerous cells and cells of a non-neoplastic proliferative disorder, such as hyperplasia, metaplasia, or most particularly, dysplasia (for review of such abnormal growth conditions, see DeVita, Jr. et al. (2001), *Cancer: Principles and Practice*, 6$^{th}$ edition, Lippincott Williams & Wilkins.

Cancers suitable for targeting using anti-5T4 antibody/drug conjugates include 5T4-expressing primary and metastatic tumors in breast, colon, rectum, lung, oropharynx, hypopharynx, esophagus, stomach, pancreas, liver, gallbladder, bile ducts, small intestine, urinary tract including kidney, bladder and urothelium, female genital tract, cervix, uterus, ovaries, male genital tract, prostate, seminal vesicles, testes, an endocrine gland, thyroid gland, adrenal gland, pituitary gland, skin, bone, soft tissues, blood vessels, brain, nerves, eyes, meninges. Other relevant cancers are 5T4-expressing leukemias and lymphomas (e.g., Hodgkin's lymphoma and non-Hodgkin's lymphoma), including indolent, aggressive, low-grade, intermediate-grade, or high-grade leukemia or lymphoma.

In particular, 5T4 is known to be expressed on cells of squamous/adenomatous lung carcinoma (non-small-cell lung carcinoma), invasive breast carcinoma, colorectal carcinoma, gastric carcinoma, squamous cervical carcinoma, invasive endometrial adenocarcinoma, invasive pancreas carcinoma, ovarian carcinoma, squamous vesical carcinoma, and choriocarcinoma. 5T4 is detected at high levels on carcinomas of bronchi, breast, colon, rectum, stomach, cervix, endometrium, pancreas, ovaria, chorium and seminal vesicles. The cell surface distribution of the 5T4 antigen may be homogeneous or heterogeneous. In colorectal carcinoma, gastric carcinoma, and ovarian carcinoma, expression of 5T4 is directly related to progression of the disease. In breast carcinoma, increased intensity of 5T4 staining on metastatic nodules is observed, however, 5T4 expression is not correlated with disease stage. The cancers may also express the Lewis Y carbohydrate antigen, including breast, colon, gastric, esophageal, pancreatic, duodenal, lung, bladder and renal carcinomas and gastric and islet cell neuroendocrine tumors. See U.S. Pat. No. 6,310,185.

Thus, patients to be treated with the anti-5T4/drug conjugates of the invention may be selected based on biomarker expression, including but not limited to elevated expression of 5T4 antigen, resulting in a patient population selected for enriched target expression rather than tumor origin or histology. Target expression can be measured as a function of the number of cells staining combined with the intensity of the cells staining. For example, classification of high expression of 5T4 includes those patients with greater than 30% (i.e., 40%, 50% or 60%) of the cells tested by immunohistochemical staining positive for 5T4 at a level of 3+ (on a scale of 1 to 4), while moderate expression of the 5T4 can include those patients with greater than 20% of the cell cells staining at 1+ to 2+.

Biomarkers other than expression of 5T4 antigen can be also used for patient selection, including characterization of the tumor based on multi-drug resistance (MDR), for example. Nearly 50 percent of human cancers are either completely resistant to chemotherapy or respond only transiently, after which they are no longer affected by commonly used anticancer drugs. This phenomenon is referred to as MDR and is inherently expressed by some tumor types, while others acquire MDR after exposure to chemotherapy treatment. The drug efflux pump P-glycoprotein mediates a majority of the MDR associated with cytotoxic chemotherapeutics. Phenotypic and functional analysis of MDR mechanisms present in cancer patient tumor specimens can be conducted in order to relate specific MDR mechanism(s) with resistance to chemotherapy in specific tumor types.

Cancer growth or abnormal proliferation refers to any one of a number of indices that suggest change within cells to a more developed cancer form or disease state. Inhibition of growth of cancer cells or cells of a non-neoplastic proliferative disorder may be assayed by methods known in the art, such as delayed tumor growth and inhibition of metastasis. Other indices for measuring inhibition of cancer growth include a decrease in cancer cell survival, a decrease in tumor volume or morphology (for example, as determined using computed tomographic (CT), sonography, or other imaging method), destruction of tumor vasculature, improved performance in delayed hypersensitivity skin test, an increase in the activity of cytolytic T-lymphocytes, and a decrease in levels of tumor-specific antigens.

While not intending to be bound by any single mode of operation, both antigen-guided targeting as well as passive targeting of anti-5T4 antibody/drug conjugates may contribute to anti-tumor efficacy. Antigen-guided targeting refers to the preferential movement and/or accumulation of a peptide or peptide analog in a target tissue (i.e., a tissue comprising 5T4-expressing cells and intended site for accumulation of an anti-5T4/drug conjugate) as compared with a control tissue (i.e., a tissue suspected to substantially lack 5T4-expressing cells and binding and/or accumulation of an administered anti-5T4/drug conjugate). Preferential localization of an antibody/drug conjugate is generally such that an amount of antibody/drug conjugate in a target tissue is about 2-fold greater than an amount of antibody/drug conjugate in a control tissue, such as an amount that is about 5-fold or greater, or about 10-fold or greater.

Passive targeting generally refers to sequestering of antibodies or antibody/drug conjugates at a tumor site due to local changes in vasculature. For example, anti-5T4/drug conjugates may leave the vasculature at the tumor site, which is fenestrated due to increased VEGF production, bind to 5T4-expressing cells and trigger internalization of the anti-5T4/drug conjugate. Poor venous and lymphatic drainage of the tumor also result in sequestration of unbound anti-5T4/drug conjugates. Antibodies conjugated to drugs with acid labile linkers can release the drug, which then diffuses into tumor cells. The anti-tumor effects of passive targeting are not permanent or as potent as those induced by antigen-guided targeting, but may contribute to total efficacy.

V.D. Formulations

Anti-5T4 antibodies and anti-5T4/drug conjugates of the invention are readily prepared and formulated for safe and efficacious clinical use. Suitable formulations for administration to a subject include aqueous and non-aqueous sterile injection solutions which may contain anti-oxidants, buffers, bacteriostats, antibacterial and antifungal agents (e.g., parabens, chlorobutanol, phenol, ascorbic acid, and thimerosal), solutes that render the formulation isotonic with the bodily fluids of the intended recipient (e.g., sugars, salts, and polyalcohols), suspending agents and thickening agents. Suitable solvents include water, ethanol, polyol (e.g., glycerol, propylene glycol, and liquid polyethylene glycol), and mixtures thereof. The formulations may be presented in unit-dose or multi-dose containers, for example, sealed ampoules and vials, and may be stored in a frozen or freeze-dried (lyophilized) condition requiring only the addition of sterile liquid carrier immediately prior to use for administration to a subject or for subsequent radiolabeling with an isotope appropriate for the intended application. Anti-5T4 antibodies and antibody/drug conjugates of the invention are preferably formulated as an effective dose, described below.

As one example, a representative anti-5T4 antibody or anti-5T4/drug conjugate formulation comprises a multi-dose formulation of 40 mg/ml antibody or antibody/drug conjugate, 25 mM acetate, 150 mM trehalose, 0.9% benzyl alcohol, 0.02% polysorbate 20 at pH 5.0, and which has a minimum shelf life of two years storage at 2-8° C. As another example, an anti-5T4 antibody or anti-5T4/drug conjugate formulation may comprise 10 mg/ml antibody or antibody/drug conjugate in 9.0 mg/ml sodium chloride, 7.35 mg/ml sodium citrate dihydrate, 0.7 mg/ml polysorbate 80, and sterile water, pH 6.5. Representative formulations of an anti-5T4/calicheamicin conjugate for administration to experimental mouse models include 2 µg or 4 µg calicheamicin (see Examples 3, 4, and 7), which may be scaled accordingly for administration to humans.

A stable lyophilized formulation of an anti-5T4 antibody or antibody/drug conjugate may be prepared by (a) dissolving an antibody/drug conjugate to a final concentration of 0.5 to 2 mg/ml in a solution comprising a cryoprotectant at a concentration of 1.5%-5% by weight, a polymeric bulking agent at a concentration of 0.5-1.5% by weight, electrolytes at a concentration 0.01 M to 0.1 M, a solubility facilitating agent at a concentration of 0.005% to 0.05% by weight, buffering agent at a concentration of 5-50 mM such that the final pH of the solution is 7.8-8.2, and water; (b) dispensing the above solution into vials at a temperature of +5° C. to +10° C.; (c) freezing the solution at a freezing temperature of −35° C. to −50° C.; (d) subjecting the frozen solution to an initial freeze drying step at a primary drying pressure of 20 to 80 microns at a shelf temperature at −10° C. to −40° C. for 24 to 78 hours; and (e) subjecting the freeze-dried product of step (d) to a secondary drying step at a drying pressure of 20 to 80 microns at a shelf temperature of +10° C. to +35° C. for 15 to 30 hours.

Representative cryoprotectants useful for lyophilization of the cryoprotectant include alditol, mannitol, sorbitol, inositol, polyethylene glycol, aldonic acid, uronic acid, aldaric acid, aldoses, ketoses, amino sugars, alditols, inositols, glyceraldehydes, arabinose, lyxose, pentose, ribose, xylose, galactose, glucose, hexose, idose, mannose, talose, heptose, glucose, fructose, gluconic acid, sorbitol, lactose, mannitol, methyl α-glucopyranoside, maltose, isoascorbic acid, ascorbic acid, lactone, sorbose, glucaric acid, erythrose, threose, arabinose, allose, altrose, gulose, idose, talose, erythrulose, ribulose, xylulose, psicose, tagatose, glucuronic acid, gluconic acid, glucaric acid, galacturonic acid, mannuronic acid, glucosamine, galactosamine, sucrose, trehalose, neuraminic acid, arabinans, fructans, fucans, galactans, galacturonans, glucans, mannans, xylans, levan, fucoidan, carrageenan, galactocarolose, pectins, pectic acids, amylose, pullulan, glycogen, amylopectin, cellulose, dextran, pustulan, chitin, agarose, keratin, chondroitin, dermatan, hyaluronic acid, alginic acid, xanthan gum, starch, sucrose, glucose, lactose, trehalose, ethylene glycol, polyethylene glycol, polypropylene glycol, glycerol and pentaerythritol.

For example, the cryoprotectant sucrose may be used at a concentration of 1.5% by weight, the polymeric bulking agent Dextran 40 or hydroxyethyl starch 40 may be used at a concentration of 0.9% by weight, the electrolyte used in the lyophilization solution is sodium chloride, which is present at a concentration of 0.05 M, and the buffering agent tromethamine may be used at a concentration of 0.02 M. A solubility facilitating agent (e.g., a surfactant such as Polysorbate 80) may also be used during the lyophilization process. Usually this solubility facilitating agent is a surfactant. Representative steps for preparation of a lyophilized formulation include freezing the vials at a temperature of −45° C.; the frozen solution is subjected to an initial freeze drying step at a primary drying pressure of 60 microns and at a shelf temperature of −30° C. for 60 hours; and subjecting the freeze-dried product to a secondary drying step at a drying pressure of 60 microns at a shelf temperature of +25° C. for 24 hours.

Anti-5T4 antibodies and antibody/drug conjugates are formulated in a pharmaceutically acceptable carrier, for example, large slowly metabolized macromolecules such as proteins, polypeptides, liposomes, polysaccharides, polylactic acids, polyglycolic acids, polymeric amino acids, amino acid copolymers and inactive virus particles. Pharmaceutically acceptable salts may also be used, for example, mineral acid salts, such as hydrochlorides, hydrobromides, phosphates and sulfates, or salts of organic acids, such as acetates, propionates, malonates and benzoates. Formulations may additionally contain liquids such as water, saline, glycerol, and ethanol, and/or auxiliary substances, such as wetting or emulsifying agents or pH buffering substances, may be present in such compositions. Such carriers enable the compositions to be formulated as tablets, pills, dragees, capsules, liquids, gels, syrups, slurries and suspensions, for ingestion by the patient.

V.E. Dose and Administration

Anti-5T4 antibodies and anti-5T4/drug conjugates of the invention may be administered parenterally, for example, via intravascular, subcutaneous, intraperitoneal, or intramuscular administration. For delivery of compositions to pulmonary pathways, compositions may be administered as an aerosol or coarse spray, i.e. transnasal administration. Intrathecal, intra medullary, or intraventricular administration may be used for treatment of central nervous system (CNS) cancers and CNS-related cancers. Anti-5T4 antibodies and anti-5T4/drug conjugates may also be administered transdermally, transcutaneously, topically, enterally, intravaginally, sublingually or rectally. Intravenous administration may be routinely used in the clinic. A delivery method is selected based on considerations such as the condition and site to be treated, the type of antibody formulation, and the therapeutic efficacy of the composition.

The present invention provides that an effective amount of an anti-5T4 antibody and anti-5T4/drug conjugate is administered to a subject, i.e., an amount of an anti-5T4 antibody or anti-5T4/drug conjugate sufficient to elicit a desired biological response. For example, when administered to a cancer-bearing subject, an effective amount comprises an amount sufficient to elicit anti-cancer activity, including cancer cell cytolysis, inhibition of cancer cell proliferation, induction of cancer cell apoptosis, reduction of cancer cell antigens, delayed tumor growth, and/or inhibition of metastasis. Tumor shrinkage is well accepted as a clinical surrogate marker for efficacy. Another well accepted marker for efficacy is progression-free survival. Anti-5T4/calicheamicin conjugates generally demonstrate at least a 25% improvement in key efficacy parameters, such as improvement in median survival, time to tumor progression, and overall response rate.

Generally, an effective dose will be in the range from about 0.01 mg/m$^2$ to about 50 mg/m$^2$, such as from about 0.1 mg/m$^2$ to about 20 mg/m$^2$, or about 15 mg/m$^2$, which dose is calculated based on the amount of anti-5T4 antibody. An effective dose of an anti-5T4/drug conjugate may also be calculated based upon an amount of the conjugated drug. For example, representative doses of an anti-5T4/calicheamicin conjugate for administration to experimental mouse models include 2 μg or 4 μg calicheamicin, which may be scaled accordingly for administration to humans. For example, anti-5T4/calicheamicin conjugates of the invention may be administered to human patients once every 3 weeks for up to 6 cycles. For a radiolabeled anti-5T4 antibody, an effective dose is typically in the range from about 1 mCi to about 300 mCi, normally about 5 mCi to 100 mCi, depending on the radioisotope and the binding affinity of the antibody.

For detection of 5T4-positive cells using the disclosed anti-5T4 antibodies, a detectable amount of a composition of the invention is administered to a subject, i.e., a dose of an anti-5T4 antibody such that the presence of the antibody may be determined in vitro or in vivo. For scintigraphic imaging using radioisotopes, typical doses of a radioisotope may include an activity of about 10 μCi to 50 mCi, or about 100 μCi to 25 mCi, or about 500 μCi to 20 mCi, or about 1 mCi to 10 mCi, or about 10 mCi.

Actual dosage levels of active ingredients in a composition of the invention may be varied so as to administer an amount of the composition that is effective to achieve the desired diagnostic or therapeutic outcome. Administration regimens may also be varied. A single injection or multiple injections may be used. The selected dosage level and regimen will depend upon a variety of factors including the activity and stability (i.e., half life) of the therapeutic composition, formulation, the route of administration, combination with other drugs or treatments, the disease or disorder to be detected and/or treated, and the physical condition and prior medical history of the subject being treated.

For anti-5T4 antibodies and anti-5T4/drug conjugates of the invention, the therapeutically effective dose may be estimated initially either in cell culture assays or in animal models, such as rodents, rabbits, dogs, pigs, and/or or primates. The animal model may also be used to determine the appropriate concentration range and route of administration. Such information may then be used to determine useful doses and routes for administration in humans. Typically, a minimal dose is administered, and the dose is escalated in the absence of dose-limiting cytotoxicity. Determination and adjustment of an effective amount or dose, as well as evaluation of when and how to make such adjustments, are known to those of ordinary skill in the art of medicine.

For combination therapies, anti-5T4 antibodies, anti-5T4/drug conjugates, and/or additional therapeutic or diagnostic agents are administered within any time frame suitable for performance of the intended therapy or diagnosis. Thus, the single agents may be administered substantially simultaneously (i.e., as a single formulation or within minutes or hours) or consecutively in any order. For example, single agent treatments may be administered within about 1 year of each other, such as within about 10, 8, 6, 4, or 2 months, or within 4, 3, 2 or 1 week(s), or within about 5, 4, 3, 2 or 1 day(s).

For additional guidance regarding formulation, dose, administration regimen, and measurable therapeutic outcomes, see Berkow et al. (2000) *The Merck Manual of Medical Information*, Merck & Co., Inc., Whitehouse Station, N.J.; Ebadi (1998) *CRC Desk Reference of Clinical Pharmacology*, CRC Press, Boca Raton, Fla.; Gennaro (2000) *Remington: The Science and Practice of Pharmacy*, Lippincott, Williams & Wilkins, Philadelphia, Pa.; Katzung (2001) *Basic & Clinical Pharmacology*, Lange Medical Books/McGraw-Hill Medical Pub. Div., New York; Hardman et al. (2001) Goodman & *Gilman's the Pharmacological Basis of Therapeutics*, The McGraw-Hill Companies, Columbus, Ohio; Speight & Holford (1997) *Avery's Drug Treatment: A Guide to the Properties, Choices, Therapeutic Use and Economic Value of Drugs in Disease Management*, Lippincott, Williams, & Wilkins, Philadelphia, Pa.

V.F. Combination Therapies

The disclosed anti-5T4 antibodies and anti-5T4/drug conjugates may be administered as an initial treatment, or for treatment of conditions that are unresponsive to conventional therapies. In addition, the anti-5T4 antibodies and anti-5T4/drug conjugates may be used in combination with other therapies (e.g., surgical excision, radiation, additional anti-cancer drugs etc.) to thereby elicit additive or potentiated therapeutic effects and/or reduce hepatocytotoxicity of some anti-cancer agents. Anti-5T4 antibodies and anti-5T4/drug conjugates of the invention may be co-administered or co-formulated with additional agents, or formulated for consecutive administration with additional agents in any order.

Representative agents useful for combination therapy include any of the drugs described herein above as useful for preparation of anti-5T4/drug conjugates. Anti-5T4 antibodies and anti-5T4/drug conjugates of the invention may also be used in combination with other therapeutic antibodies and antibody/drug conjugates, including anti-5T4 antibodies other than the disclosed anti-5T4 antibodies, as well as antibodies and conjugates targeting a different antigen. Representative antibodies, which may be used alone or as an antibody/drug conjugate, include anti-CD19 antibodies, anti-CD20 antibodies (e.g., RITUXAN®, ZEVALIN®, BEXXAR®), anti-CD22 antibodies, anti-CD33 antibodies (e.g., MYLOTARG®), anti-CD33 antibody/drug conjugates, anti-Lewis Y antibodies (e.g., Hu3S193, Mthu3S193, AGmthu3S193), anti-HER-2 antibodies (e.g., HERCEPTIN® (trastuzumab), MDX-210, OMNITARG® (pertuzumab, rhuMAb 2C4)), anti-CD52 antibodies (e.g., CAMPATH®), anti-EGFR antibodies (e.g., ERBITUX® (cetuximab), ABX-EGF (panitumumab)), anti-VEGF antibodies (e.g., AVASTIN® (bevacizumab)), anti-DNA/histone complex antibodies (e.g., ch-TNT-1/b), anti-CEA antibodies (e.g., CEA-Cide, YMB-1003) hLM609, anti-CD47 antibodies (e.g., 6H9), anti-VEGFR2 (or kinase insert domain-containing receptor, KDR) antibodies (e.g., IMC-1C11), anti-EpCAM antibodies (e.g., ING-1), anti-FAP antibodies (e.g., sibrotuzumab), anti-DR4 antibodies (e.g., TRAIL-R), anti-progesterone receptor antibodies (e.g., 2C5), anti-CA19.9 antibodies (e.g., GIVAREX®) and anti-fibrin antibodies (e.g., MH-1).

Anti-5T4 antibody/drug conjugates may also be administered together with one or more combinations of cytotoxic agents as part of a treatment regimen. Useful cytotoxic preparations for this purpose include CHOPP (cyclophosphamide, doxorubicin, vincristine, prednisone and procarbazine); CHOP (cyclophosphamide, doxorubicin, vincristine, and prednisone); COP (cyclophosphamide, vincristine, prednisone); CAP-BOP (cyclophosphamide, doxorubicin, procarbazine, bleomycin, vincristine and prednisone); m-BACOD (methotrexate, bleomycin, doxorubicin, cyclophosphamide, vincristine, dexamethasone, and leucovorin; ProMACE-MOPP (prednisone, methotrexate, doxorubicin, cyclophosphamide, etoposide, leukovorin, mechloethamine, vincristine, prednisone and procarbazine); ProMACE-CytaBOM (prednisone, methotrexate, doxorubicin, cyclophosphamide, etoposide, leukovorin, cytarabine, bleomycin and vincristine); MACOP-B (methotrexate, doxorubicin, cyclophosphamide, vincristine, prednisone, bleomycin and leukovorin); MOPP (mechloethamine, vincristine, prednisone and procarbazine); ABVD (adriamycin/doxorubicin, bleomycin, vinblastine and dacarbazine); MOPP (mechloethamine, vincristine, prednisone and procarbazine) alternating with ABV (adriamycin/doxorubicin, bleomycin, vinblastine); MOPP (mechloethamine, vincristine, prednisone and procarbazin) alternating with ABVD (adriamycin/doxorubicin, bleomycin, vinblastine and dacarbazine); ChIVPP (chlorambucil, vinblastine, procarbazine, prednisone); IMVP-16 (ifosfamide, methotrexate, etoposide); MIME (methyl-gag, ifosfamide, methotrexate, etoposide); DHAP (dexamethasone, high-dose cytaribine and cisplatin); ESHAP (etoposide, methylpredisolone, HD cytarabine, and cisplatin); CEPP(B) (cyclophosphamide, etoposide, procarbazine, prednisone and bleomycin); CAMP (lomustine, mitoxantrone, cytarabine and prednisone); and CVP-1 (cyclophosphamide, vincristine and prednisone); DHAP (cisplatin, high-dose cytarabine and dexamethasone); CAP (cyclophosphamide, doxorubicin, cisplatin); PV (cisplatin, vinblastine or vindesine); CE (carboplatin, etoposide); EP (etoposide, cisplatin); MVP (mitomycin, vinblastine or vindesine, cisplatin); PFL (cisplatin, 5-fluorouracil, leucovorin); IM (ifosfamide, mitomycin); IE (ifosfamide, etoposide); IP (ifosfamide, cisplatin); MIP (mitomycin, ifosfamide, cisplatin); ICE (ifosfamide, carboplatin, etoposide); PIE (cisplatin, ifosfamide, etoposide); Viorelbine and cisplatin; Carboplatin and paclitaxel; CAV (cyclophosphamide, doxorubicin, vincristine); CAE (cyclophosphamide, doxorubicin, etoposide); CAVE (cyclophosphamide, doxorubicin, vincristine, etoposide); EP (etoposide, cisplatin); and CMCcV (cyclophosphamide, methotrexate, lomustine, vincristine).

Anti-5T4 antibodies and anti-5T4/calicheamicin conjugates may be used in combination with systemic anti-cancer drugs, such as epithilones (BMS-247550, Epo-906), reformulations of taxanes (Abraxane, Xyotax), microtubulin inhibitors (MST-997, TTI-237), or with targeted cytotoxins such as CMD-193 and SGN-15. Additional useful anti-cancer agents include TAXOTERE®, TARCEVA®, GEMZAR® (gemcitabine), 5-FU, AVASTIN®, ERBITUX®, TROVAX®, anatumomab mafenatox, letrazole, docetaxel, and anthracyclines.

For combination therapies, an anti-5T4 antibody, anti-5T4/drug conjugate, and/or one or more additional therapeutic or diagnostic agents are administered within any time frame suitable for performance of the intended therapy or diagnosis. Thus, the single agents may be administered substantially simultaneously (i.e., as a single formulation or within minutes or hours) or consecutively in any order. For example, single agent treatments may be administered within about 1 year of each other, such as within about 10, 8, 6, 4, or 2 months, or within 4, 3, 2 or 1 week(s), or within about 5, 4, 3, 2 or 1 day(s). The administration of an anti-5T4 antibody or anti-5T4/calicheamicin conjugate in combination with a second therapeutic agent preferably elicits a greater effect than administration of either alone.

EXAMPLES

The following examples have been included to illustrate modes of the invention. Certain aspects of the following examples are described in terms of techniques and procedures found or contemplated by the present co-inventors to work well in the practice of the invention. These examples illustrate standard laboratory practices of the co-inventors. In light of the present disclosure and the general level of skill in the art, those of skill will appreciate that the following examples are intended to be exemplary only and that numerous changes, modifications, and alterations may be employed without departing from the scope of the invention.

Example 1

Murine Anti-5T4 Antibodies

Anti-5T4 antibodies were prepared in mice using human 5T4 antigen and standard methods for immunization. Hybridoma cell lines producing the A1, A2, and A3 antibodies were produced by fusion of individual B cells with myeloma cells.

The A1, A2, and A3 anti-5T4 antibody heavy chain and light chain variable regions were cloned using the SMART® cDNA synthesis system (Clontech Laboratories Inc. of Mountain View, Calif.) followed by PCR amplification. The cDNA was synthesized from 1 μg total RNA isolated from A1, A2, or A3 hybridoma cells, using oligo(dT) and the SMART® IIA oligo (Clontech Laboratories Inc.) with POWERSCRIPT™ reverse transcriptase (Clontech Laboratories Inc.). The cDNA was then amplified by PCR using a primer which anneals to the SMART® IIA oligo sequence and mouse constant region specific primer (mouse Kappa for the light chain, mouse IgG2a for the A1 heavy chain, mouse IgG2b for the A2 heavy chain, and mouse IgG1 for the A3 heavy chain) with VENT® polymerase (New England Biolabs Inc. of Ipswich, Mass.). Heavy chain and light chain variable region PCR products were subcloned into the pED6 expression vector and the nucleic acid sequence was determined. This method is advantageous in that no prior knowledge of the DNA sequence is required. In addition, the resultant DNA sequence is not altered by use of degenerate PCR primers.

The nucleotide sequences of the A1, A2, and A3 heavy chain variable regions are set forth as nucleotides 58-414 of SEQ ID NO:1, nucleotides 55-405 of SEQ ID NO:5, and nucleotides 58-423 of SEQ ID NO:9, respectively. The amino acid sequences of the A1, A2, and A3 heavy chain variable regions are set forth as residues 20-138 of SEQ ID NO:2, residues 19-135 of SEQ ID NO:6, and residues 20-141 of SEQ ID NO:10, respectively. The nucleotide sequences of the A1, A2, and A3 light chain variable regions are set forth as nucleotides 61-381 of SEQ ID NO:3, nucleotides 67-390 of SEQ ID NO:7, and nucleotides 61-381 of SEQ ID NO:11, respectively. The amino acid sequences of the A1, A2, and A3 light chain variable regions are set forth as residues 21-127 of SEQ ID NO:4, residues 23-130 of SEQ ID NO:8, and residues 21-127 of SEQ ID NO:12, respectively. See also FIGS. 1A-1C.

To assess the novelty of the A1, A2, and A3 anti-5T4 variable region sequences, BLASTp searches (for protein query sequences) were conducted using default parameters of Expect=10, Word Size=3, a low complexity filter, and the BLOSUM62 matrix, permitting gap costs of existence=11, and extension=1. BLASTn searches (for nucleotide query sequences) were conducted using default parameters of Expect=10, Word Size=11, and a low complexity filter. BLAST search results are reported as a list of sequences related to the query sequence, ranked in order of E value, which is an indicator of the statistical significance of matches identified in the database. Sequences most closely related to the variable region sequences used for BLAST analysis are identified in Table 1 (BLASTn) and Table 2 (BLASTp).

TABLE 1

BLASTn Analysis

| Query Sequence | Identity (%) of Closest Subject Sequence | Description of Closest Subject Sequence |
|---|---|---|
| A1 VH (SEQ ID NO: 1) | 97% | gi\|31322165\|gb\|AY169686.1\| *Mus musculus* clone VGBC1.13 immunoglobulin heavy chain variable region precursor, gene, partial cds |
| A1 VL (SEQ ID NO: 3) | 96% | gi\|804922\|dbj\|D50385.1\|MUSIKCVRJ *Mus musculus* mRNA for immunoglobulin kappa chain variable region, partial sequence, cell_line: K3F10 |
| A2 VH (SEQ ID NO: 5) | 97% | gi\|11612012\|gb\|AF303853.1\|AF303853 *Mus musculus* clone J558.22 immunoglobulin heavy chain variable region mRNA, partial cds |
| A2 VL (SEQ ID NO: 7) | 97% | gi\|1556423\|emb\|X79906.1\| MMMABMST2 *M. musculus* mRNA for monoclonal antibody MST2 light chain |
| A3 VH (SEQ ID NO: 9) | 99% | gi\|3420272\|gb\|AF064445.1\|AF064445 *Mus musculus* immunoglobulin heavy chain variable region (Vh10.2) gene, Vh10.2a allele, partial cds |
| A3 VL (SEQ ID NO: 11) | 98% | gi\|2906107\|gb\|AF045512.1\|AF045512 *Mus musculus* 9E10 monoclonal antibody kappa light chain variable region, (IgK) mRNA, partial cds |

TABLE 2

BLASTp Analysis

| Query Sequence | Identity (%) of Closest Subject Sequence | Description of Closest Subject Sequence |
|---|---|---|
| A1 VH (SEQ ID NO: 2) | 84% | gi\|15865327\|emb\|CAC82228.1\| immunoglobulin heavy chain [*Mus musculus*] |
| A1 VL (SEQ ID NO: 4) | 93% | gi\|644862\|gb\|AAA62143.1\| anti-alpha 4 integrin immunoglobulin kappa chain V region |

TABLE 2-continued

BLASTp Analysis

| Query Sequence | Identity (%) of Closest Subject Sequence | Description of Closest Subject Sequence |
|---|---|---|
| A2 VH (SEQ ID NO: 6) | 85% | gi\|15149453\|gb\|AAK85298.1\| single chain antibody HFN7.1 [synthetic construct] |
| A2 VL (SEQ ID NO: 8) | 95% | gi\|297678\|emb\|CAA80086.1\| immunoglobulin variable region [*Mus musculus domesticus*] |
| A3 VH (SEQ ID NO: 10) | 90% | gi\|2906050\|gb\|AAC04511.1\| anti-poly(dC) monoclonal antibody heavy chain [*Mus musculus*] |
| A3 VL (SEQ ID NO: 12) | 97% | gi\|2906108\|gb\|AAC04540.1\| monoclonal antibody kappa light chain [*Mus musculus*] |

Example 2

Binding Specificity and Affinity of Murine Anti-5T4 Antibodies

To assess the binding specificity and affinity of the A1, A2, and A3 antibodies, BIACORE® analysis was performed using human 5T4 antigen immobilized on a CM5 chip. BIACORE® technology utilizes changes in the refractive index at the surface layer upon binding of the antibody to the 5T4 antigen immobilized on the layer. Binding is detected by surface plasmon resonance (SPR) of laser light refracting from the surface. Analysis of the signal kinetics on rate and off rate allows discrimination between non-specific and specific interactions. The H8 anti-5T4 antibody was used as a control. H8 is a hybridoma-generated monoclonal mouse IgG1 antibody described in PCT International Publication No. WO 98/55607 and in Forsberg et al. (1997) *J. Biol. Chem.* 272(19):124430-12436.

TABLE 3

Results of BIACORE ® Assay

| Antibody | KD (M) | KA (1/M) | kd (1/s) | ka (1/Ms) |
|---|---|---|---|---|
| H8 | $4.1 \times 10^{-10}$ | $2.5 \times 10^{9}$ | $5.1 \times 10^{-5}$ | $1.3 \times 10^{5}$ |
| A1 | $6.4 \times 10^{-10}$ | $1.6 \times 10^{9}$ | $1.3 \times 10^{-4}$ | $2.0 \times 10^{5}$ |
| A2 | $1.5 \times 10^{-8}$ | $6.5 \times 10^{7}$ | $8.7 \times 10^{-4}$ | $5.6 \times 10^{4}$ |
| A3 | $2.2 \times 10^{-9}$ | $4.6 \times 10^{8}$ | $5.2 \times 10^{-5}$ | $2.4 \times 10^{4}$ |

The BIACORE® results show that H8 and A1 antibodies have higher affinity for 5T4 when compared to the A2 and A3 antibodies. A2 is a relatively low affinity antibody. Unusual cysteines are present at residue 67 of the A1 heavy chain variable region and residue 91 of the A3 heavy chain variable region. Replacement of these residues with phenylalanine (A1) or tyrosine (A3) did not alter antibody binding properties or expression levels.

Figure 2:
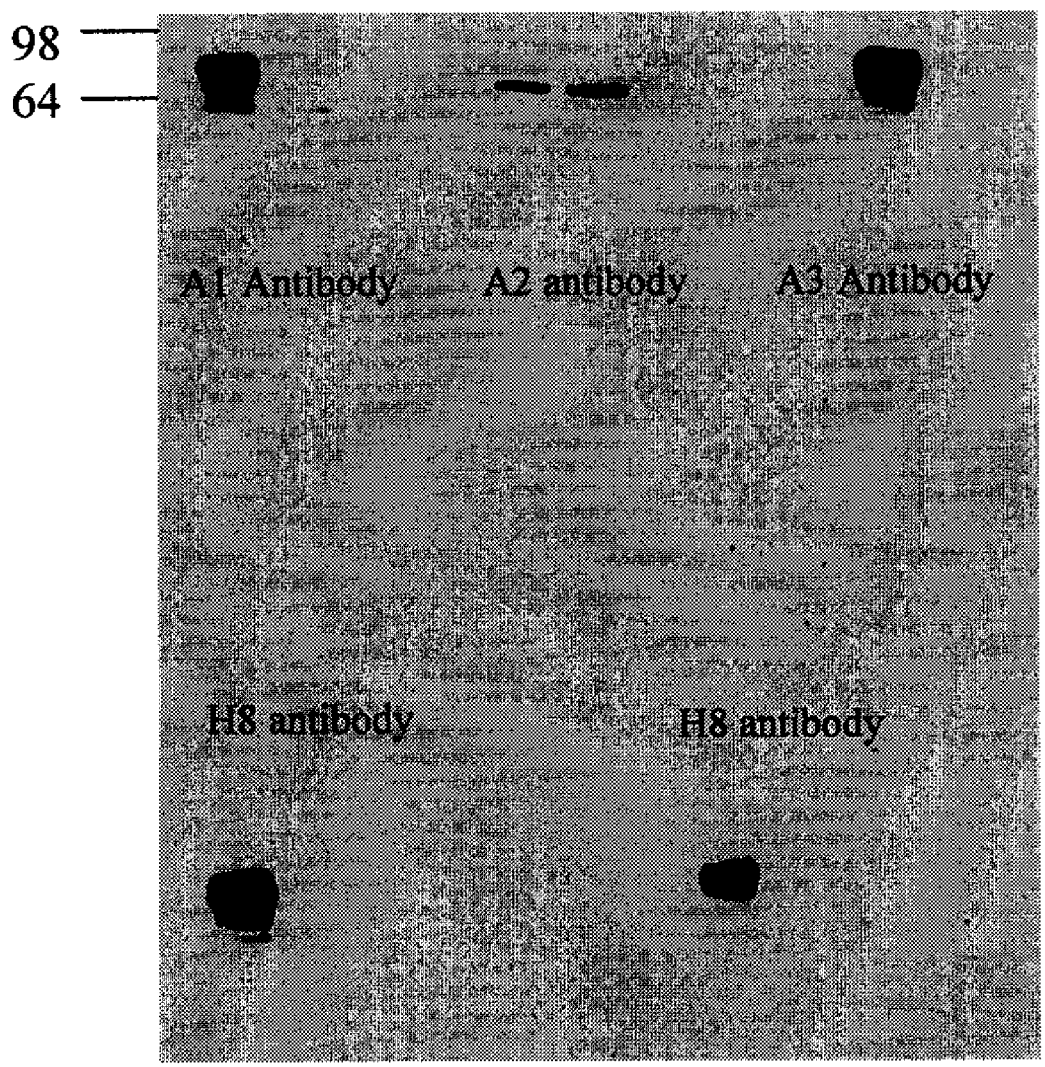
FIG. 2 is a Western blot prepared using CT26/5T4 cell lysates and probed with the indicated antibodies.

The binding affinity of the H8, A1, A2, and A3 antibodies was also assayed by Western blotting using CT26/5T4 cell lysates, which identified strong binding by H8, A1, and A3. See FIG. 2.

The ability of the H8, A1, A2, and A3 antibodies to bind cells expressing 5T4 antigen was assayed using fluorescence activated cell sorting (FACS) of PC14PE6 cells. All antibodies showed specific binding to 5T4-expressing PC14PE6 cells, however, the level of A2 binding was significantly lower than that observed for H8, A1, and A3. See Table 4.

TABLE 4

Results of FACS Analysis

| Antibody | Mean Cellular Flouresence |
|---|---|
| Control (secondary Ab) | 4 |
| Control (murine IgG) | 4 |
| H8 | 24 |
| A1 | 18 |
| A2 | 7 |
| A3 | 27 |

Figure 3A:
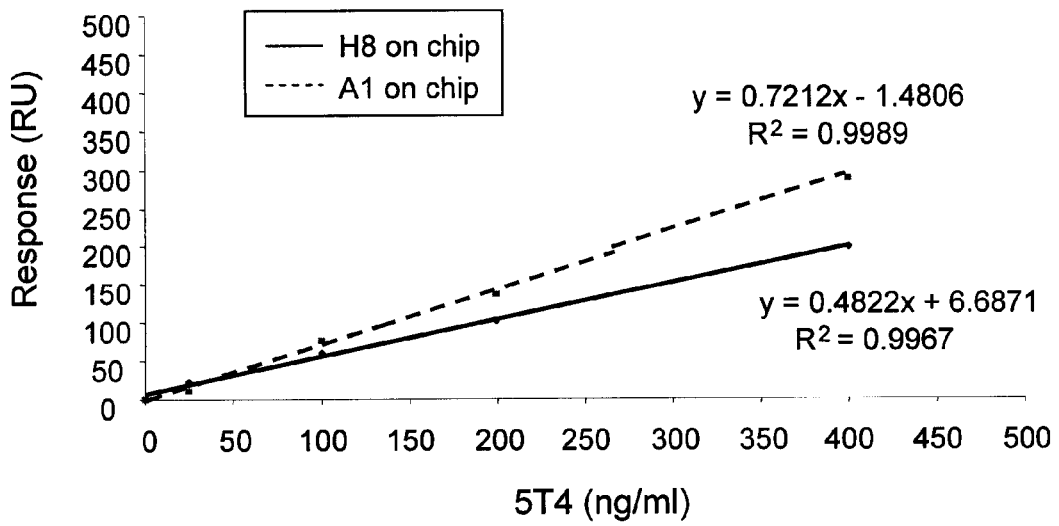
FIGS. 3A-3B are line graphs that show response curves and binding kinetics for two independent preparations of H8 and A1 antibodies. The preparations were substantially equivalent.
Figure 3B:
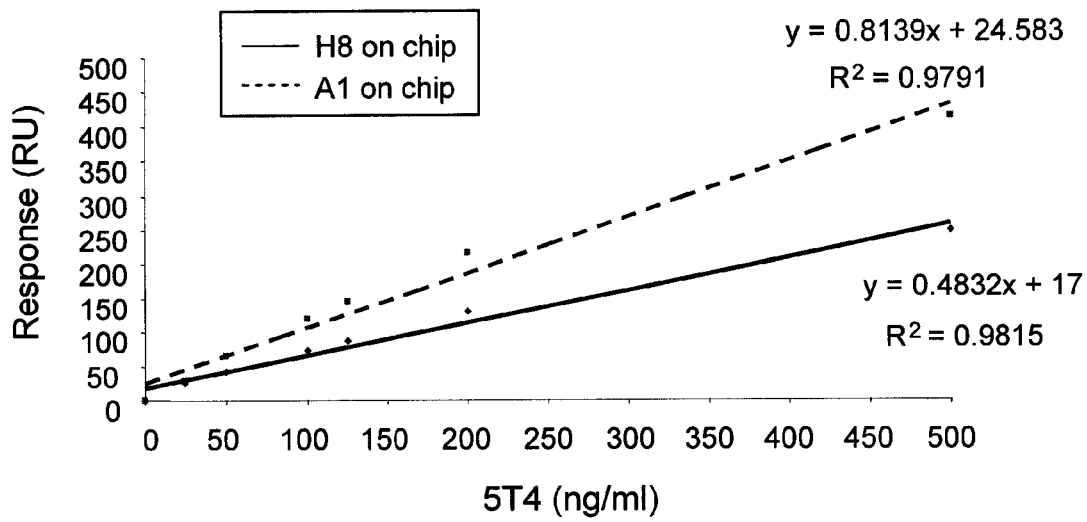

To assess potential variability in antibody production, two independent preparations of A1 and H8 were tested. The binding and kinetic properties of each antibody, when compared from each preparation, were not significantly different. See FIGS. 3A-3B.

Example 3

Internalization of Murine Anti-5T4 Antibodies by 5T4-Expressing Cells

Figure 4A:
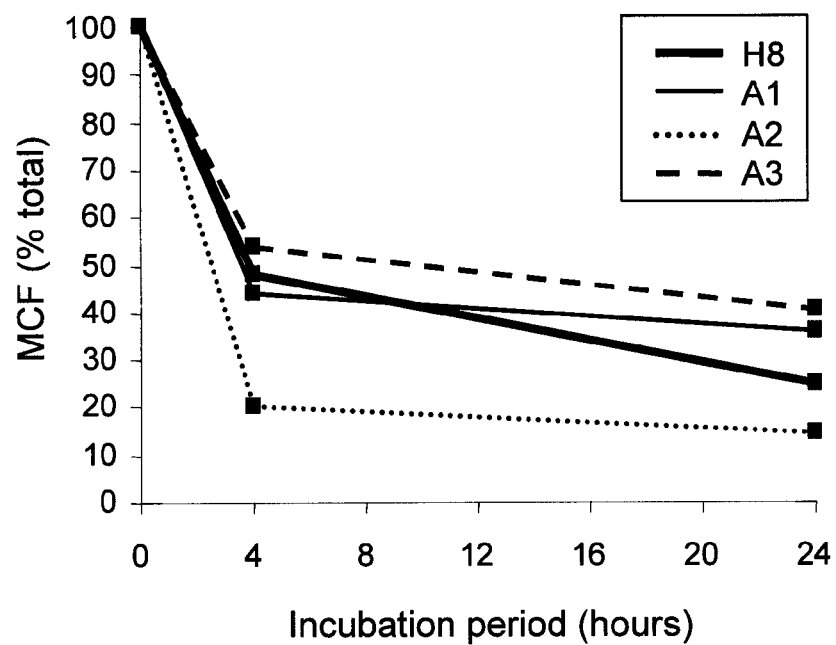
FIGS. 4A-4C are line graphs that show modulation of H8, A1, A2, and A3 antibodies by MDAMB435/5T4 cells. Levels of antibody at the cell surface decline over time (FIGS. 4A, 4C (solid)), while the levels of antibody in the supernatant remain constant (FIGS. 4B, 4C (open)). MCF, mean cellular fluorescence; supt, supernatant.
Figure 4B:
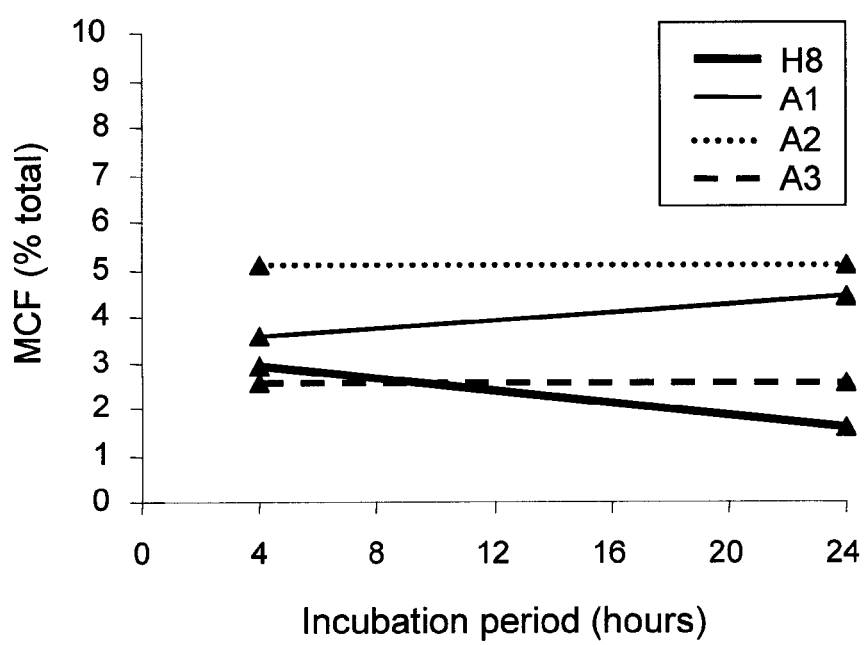
Figure 4C:
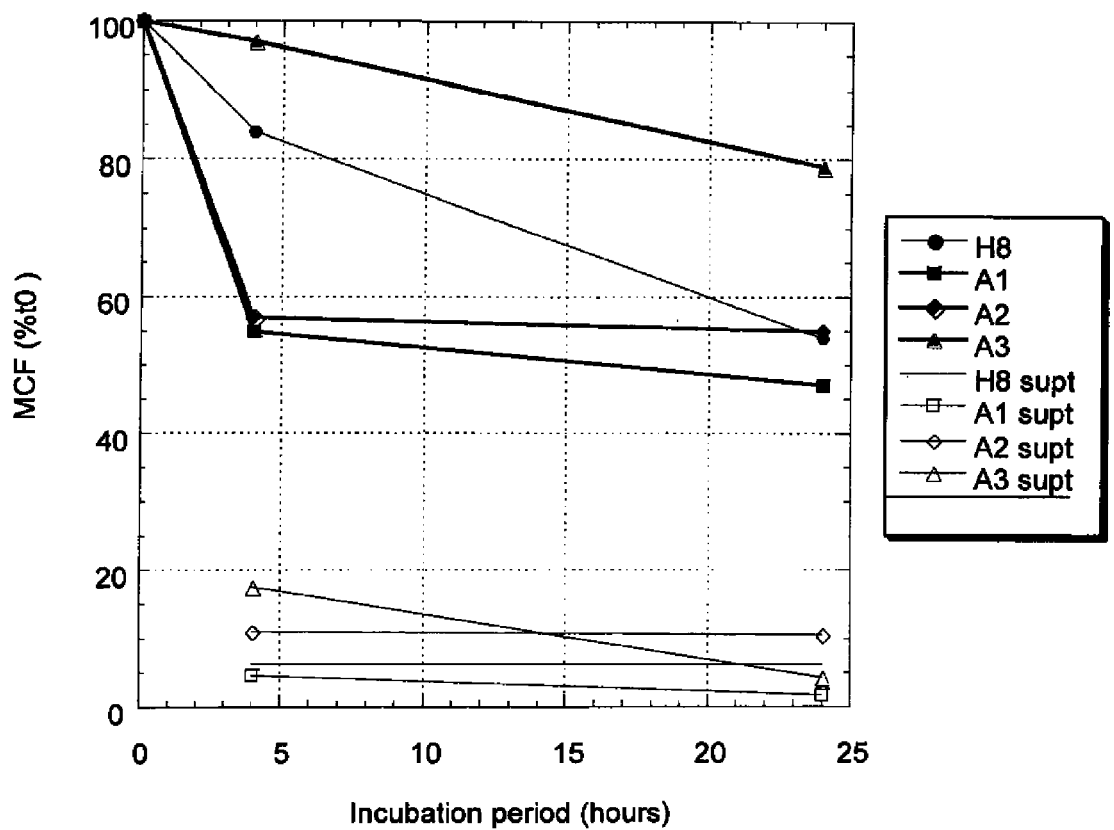

To assess internalization of antibodies upon binding to 5T4 antigen, the amount of H8 and A1 antibodies detected at the cell surface versus in the supernatant was determined as a function of time. Non-enzymatically dissociated MDAMB435/5T4 cells (human breast cancer cells) were exposed to anti-5T4 antibodies for 1 hour at 4° C. Cells were washed and incubated in media at 37° C. for 4 hours or 24 hours. The amount of antibody bound to cellular membranes versus unbound antibody (i.e., presence in the supernatant) was determined using FACS. The disappearance of 5T4 antibodies from the surface of MDAMB435/5T4 cells demonstrates modulation of the 5T4 antigen/antibody complex at the cell surface, which may indicate internalization and/or dissociation. See FIGS. 4A-4C.

Example 4

Epitope Mapping Using 5T4 Chimeras

Figure 5:
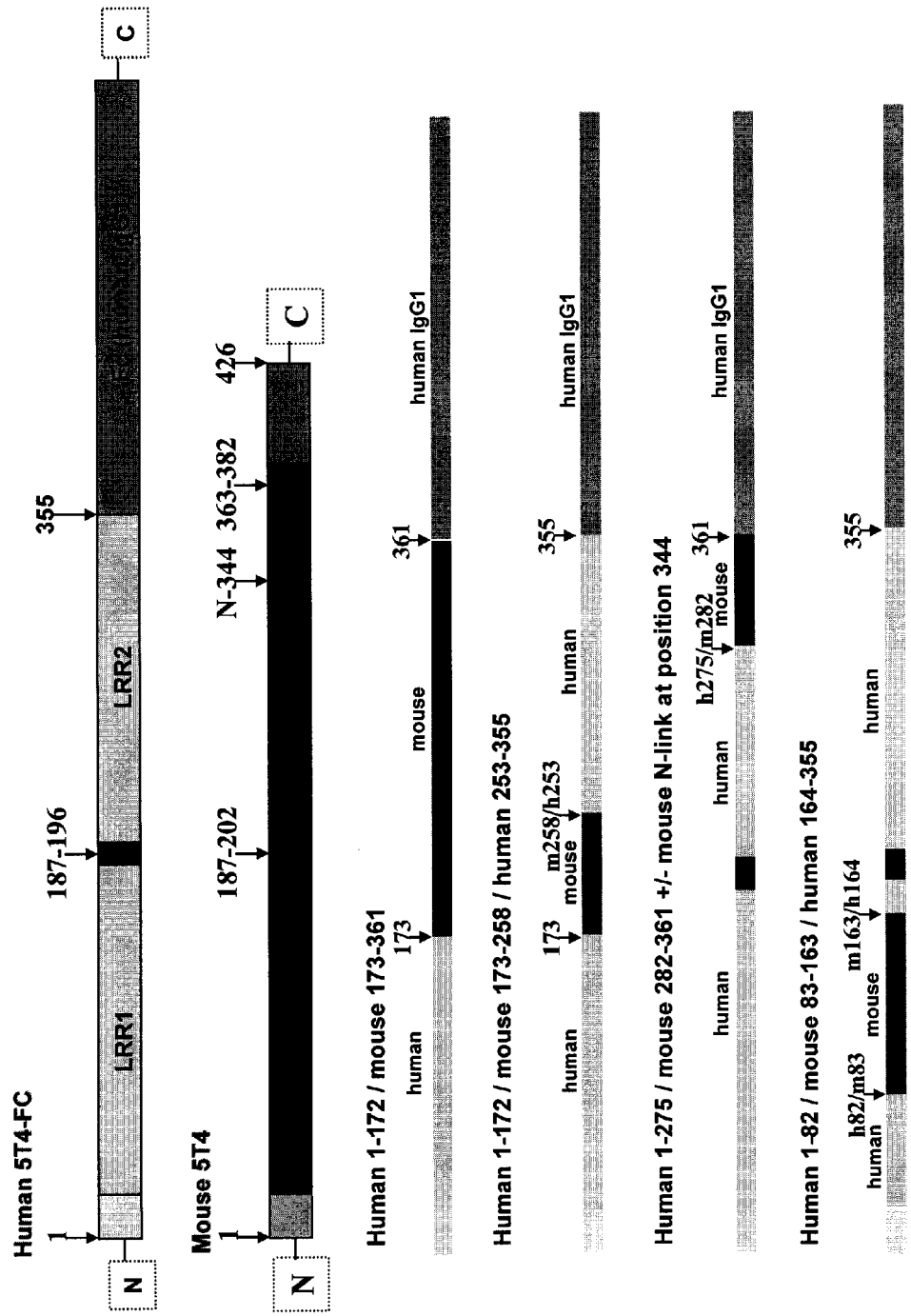
FIG. 5 is a schematic diagram of the human ectodomain 5T4 Fc construct, the mouse ectodomain 5T4 Fc construct, and the human/mouse 5T4 chimera constructs. These constructs were used for epitope mapping as described in Example 4

To identify the epitopes to which each of the A1, A2, A3, and H8 antibodies bind, ELISA assays were performed using (1) 5T4 ectodomain Fc constructs with deleted or mutated sequences, and (2) 5T4 chimera constructs transiently expressed in COS-1 cells. The ectodomain includes the amino-terminal region, two leucine-rich repeats, and the intervening hydrophilic region. Fusion proteins containing a 5T4 ectodomain and a Fc constant regions from human IgG1 were prepared using mouse 5T4 (amino acids 1-361), rat 5T4 (amino acids 1-361), cynomologous monkey 5T4 (amino acids 1-355), chimpanzee 5T4 (amino acids 1-355), and black-tailed marmoset (amino acids 1-355). The 5T4 chimera constructs are depicted in FIG. 5. The binding results are summarized in Table 5, which indicates specific binding, partial binding, or lack of binding, by each of the H8, A1, A2, and A3 antibodies. Humanized H8 and chimeric A1, A2, and A3 antibodies showed binding properties similar to murine H8, A1, A2, and A3 respectively.

Figure 7:
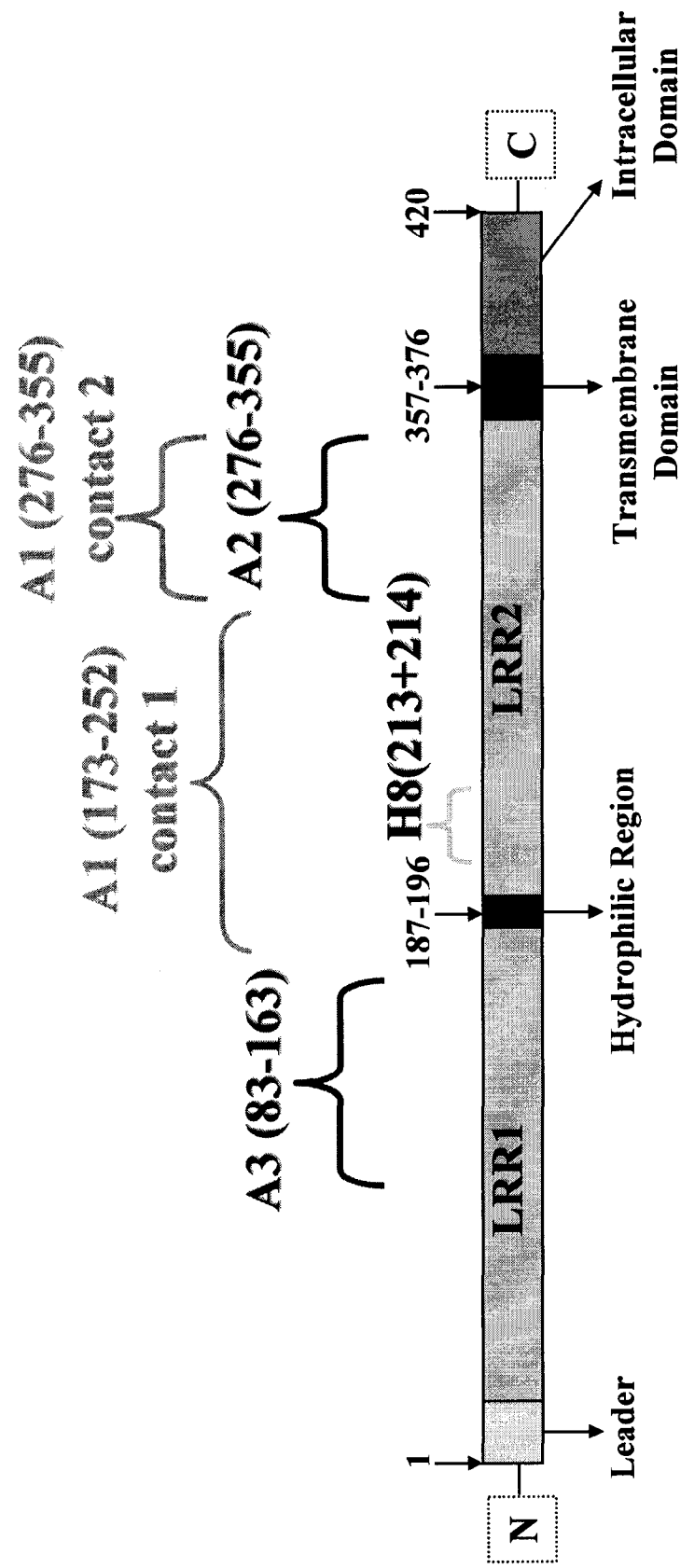
FIG. 7 is a linear diagram showing the human 5T4 epitopes bound by H8, A1, A2, and A3. The indicated residues are residues of the 5T4 antigen described by Myers et al. (1994) *J. Biol. Chem.* 269(12):9319-9324, also available as GenBank Accession No. Z29083 (SEQ ID NO:87). LRR, Leucine-rich repeat.

Based upon these results, it was determined that humanized H8 antibody binds to human 5T4 between residues 173 and 252. Humanized H8 binds to 5T4 with or without N-linked glycosylation at residue 344, which confirms that binding of humanized H8 to human 5T4 is not membrane proximal. The A1 antibody has a first contact with human 5T4 between residues 173 and 252 and a second contact with human 5T4 between residues 282 and 361. The A2 antibody binds human 5T4 between residues 282 and 361. The A3 antibody binds the first leucine-rich repeat region of human 5T4 between residues 83 through 163. The epitopes bound by each antibody are depicted in FIG. 7.

TABLE 5

Results Epitope Mapping Using 5T4 Ectodomain Fc Fusions and Human/Mouse 5T4 Chimeras

| 5T4 antigen construct | Antibody | | | |
|---|---|---|---|---|
| | H8 | A1 | A2 | A3 |
| human 5T4 ectodomain Fc | + | + | + | + |
| mouse 5T4 ectodomain Fc | − | − | − | − |
| rat 5T4 ectodomain Fc | − | +/− | − | − |
| cynomologous monkey 5T4 ectodomain Fc | − | + | + | + |
| chimpanzee 5T4 ectodomain Fc | + | + | + | + |
| black-tailed marmoset 5T4 ectodomain Fc | +/− | + | + | − |
| human/mouse 83-163 | + | + | + | − |
| human/mouse 173-361 | − | − | − | + |
| human/mouse 173-258 | − | +/− | + | + |
| human/mouse 282-361 (with or without N-link at position 344) | + | +/− | − | + |

(+) binding; (−) no binding; (+/−) partial binding

Based upon the different binding observed to 5T4 ectodomains from human and cynomologous monkey, targeted mutations were made to distinguish residues that participate in antibody binding. Binding of humanized H8 antibody was assayed to each of the mutated 5T4 ectodomains noted in Table 6 below, i.e., human 5T4 ectodomains that include a residue from cynomologous monkey at the indicated position. These results showed that residues 213 and 214 of human 5T4 antigen are required for the epitope bound by humanized H8.

TABLE 6

Results of Epitope Mapping Using Human 5T4 Ectodomain/Fc Fusion With Targeted Mutations

| mutation | humanized H8 binding |
|---|---|
| E189K | + |
| V200K | + |
| L204V | + |
| R213H | +/− |
| R213H and R214L | − |

(+) binding; (−) no binding; (+/−) partial binding

In addition to direct binding assays, competitive binding assays were performed using biotinylated humanized H8 antibody and each of the A1, A2, or A3 antibodies. Inhibition of binding to human 5T4 was not observed, supporting that each of A1, A2, and A3 binds to a 5T4 epitope that is distinct from that bound by the H8 antibody. See FIGS. 6A-6.

Example 5

Epitope Mapping Using BIACORE®

Epitope mapping of the H8, A1, A2, and A3 antibodies was also performed using BIACORE® using a CM5 chip with bound human 5T4 antigen. The chip was saturated with H8, A1, A2, or A3 antibody, and a first response was measured. The chip was then saturated with a second antibody from among the H8, A1, A2, and A3 antibodies, and a second response was measured. For multiple experiments, the chip was regenerated by dissociation of the bound antibodies in 10 mM glycine, pH 1.5, followed by a buffer wash. The results are summarized in Table 7 below. The percentages shown are the response units measured upon binding by a second antibody directly to the CM5 chip divided by the response units measured upon binding of the second antibody to a CM5 chip saturated with a first antibody. These results show that H8, A1, A2, and A3 each bind a distinct epitope on human 5T4. The epitopes bound by the H8 and A3 antibodies are sterically close to each other such that the rate of association with antigen is decreased when binding of H8 is assayed in the presence of A3, and vice versa. Similar results were obtained using the chimeric and humanized H8, A1, A2, and A3 antibodies, which were prepared as described in Example 7 herein below. See Table 8.

TABLE 7

Results of Competition Assays Using BIACORE ® - Percentage Response of Second Antibody Following Saturation With First Antibody

| 2nd antibody | 1$^{st}$ antibody | | | |
|---|---|---|---|---|
| | H8 | A1 | A2 | A3 |
| H8 | — | 114% | 102% | 85% |
| A1 | 109% | — | 109% | 98% |
| A2 | 99% | 98% | — | 94% |
| A3 | 73% | 104% | 106% | — |

TABLE 8

Results of Competition Assays Using BIACORE ® - Percentage of Second Antibody Bound Following Saturation With First Antibody

| second antibody/first antibody bound | time after injection of second antibody (seconds) | | | | | |
|---|---|---|---|---|---|---|
| | 19 | 37.5 | 75 | 150 | 300 | 600 |
| humanized H8/ chimeric A3 | 44.9% | 57.0% | 69.1% | 79.4% | 86.6% | 91.3% |
| chimeric A3/ humanized H8 | 46.2% | 51.2% | 58.4% | 67.5% | 76.2% | 83.6% |
| chimeric A2/ chimeric A1 | 102.9% | 93.5% | 90.1% | 89.0% | 88.9% | 89.1% |
| chimeric A1/ chimeric A2 | 92.5% | 90.6% | 91.4% | 92.7% | 93.9% | 95.5% |
| chimeric A3/ chimeric A1 | 82.1% | 82.0% | 84.5% | 87.8% | 90.8% | 92.8% |
| chimeric A1/ chimeric A3 | 98.8% | 96.5% | 97.0% | 98.0% | 98.8% | 99.6% |
| chimeric A3/ chimeric A2 | 92.2% | 88.6% | 89.5% | 91.5% | 93.4% | 94.6% |
| chimeric A2/ chimeric A3 | 89.2% | 88.4% | 89.8% | 91.5% | 92.9% | 94.3% |
| humanized H8/ chimeric A1 | 93.2% | 92.7% | 94.2% | 95.9% | 96.9% | 97.3% |
| chimeric A1/ humanized H8 | 92.7% | 92.4% | 93.8% | 95.8% | 97.3% | 98.7% |
| humanized H8/ chimeric A2 | 93.8% | 94.0% | 96.0% | 98.1% | 99.8% | 101.3% |
| chimeric A2/ humanized H8 | 86.9% | 84.7% | 86.9% | 90.5% | 93.7% | 96.7% |

The combined results of epitope mapping studies as determined using chimeric constructs (see Example 4) and BIACORE® are presented in FIG. 7.

Example 6

Efficacy of Anti-5T4/Calicheamicin Conjugates

A vital dye (MTS) staining was used to determine the number of surviving cells following exposure to various treatments. MTS (non-radioactive cell proliferation assay kit) was purchased from Promega (Madison, Wis.) and used according to the manufacturer's specifications. For each cell line a calibration curve (cell number versus optical density after 2 hours) was established to estimate an appropriate initial seeding density. Cells were then seeded in 96-multiwell dishes at a density of 750 to 5,000 cells per well. Immediately after seeding, the cells were exposed to various concentrations (0, 0.01, 0.05, 0.1, 1, 10, 100 and 500 ng calicheamicin equivalents/ml) of calicheamicin, CMA-676 and calicheamicin conjugates of anti-5T4 antibodies. Following determination of the number of cells surviving 96 hours of drug-exposure, the $ED_{50}$ was calculated based on the logistic regression parameters derived from the dose-response curves. The $ED_{50}$ was defined as the concentration of drug (CalichDMH) that caused a 50% reduction of the cell number after 96 hours exposure to the drug. A calicheamicin equivalent (cal. eq.) is the concentration of calicheamicin given either as a pure substance or as a conjugate. Depending on the amount of calicheamicin bound to the antibody (antibody drug loading), calicheamicin equivalents which are different may indicate different protein concentrations.

The results of MTS assays are shown in Table 9. Antibody/ calicheamicin conjugates prepared using the A1 and A3 anti-5T4 assays substantially reduced viability of MDAMB435/ 5T4 cells. Selectivity values were calculated by comparing the specific activity of the conjugate to the non-specific activity. That is, fold CalichDMH for the 5T4 expressing cells were divided by the fold CalichDMN values for cells not expressing 5T4. When a non-specific antibody is used, for example hp67.6 (CMA-676), the fold CalichDMH values are approximately the same such that the selectivity is 1.

TABLE 9

Results of MTS Assays

| | cell line | |
|---|---|---|
| Treatment | MDAMB435/neo ED50 (ng/ml) | MDAMB435/5T4 ED50 (ng/ml) |
| CalichDMH | 3.3-5.0 | 5.0-8.0 |
| huH8-ActBut-CalichDMH | 0.4-0.8 | 0.08-0.1 |
| CMA-676 | 34-60 | 50-100 |
| A1-ActBut-CalichDMH | 22-34 | 0.4-0.6 |
| A2-ActBut-CalichDMH | 60 | 40 |
| A3-ActBut-CalichDMH | 20-20 | 0.3-20 |

| | cell line | |
|---|---|---|
| treatment | MDAMB435/neo Fold CalichDMH | MDAMB435/5T4 Fold CalichDMH |
| CalichDMH | 1.0-1.0 | 1.0-1.0 |
| huH8-ActBut-CalichDMH | 4.0-12.5 | 50-100 |
| CMA-676 | 0.08-0.1 | 0.08-0.1 |
| A1-ActBut-CalichDMH | 0.14-0.15 | 13-13 |

TABLE 9-continued

Results of MTS Assays

| | | |
|---|---|---|
| A2-ActBut-CalichDMH | 0.06 | 0.13 |
| A3-ActBut-CalichDMH | 0.17-0.25 | 0.4-17 |

Selectivity: H8 = 8; hP67.6 = 1; A1 = 93; A3 = 1.6
CalichDMH, unconjugated calicheamicin
huH8-AcBut-CalichDMH, humanized H8 antibody conjugated to calicheamicin using 4-(4'-acetylphenoxy)butanoic acid (AcBut)
CMA-676, anti-CD33/calicheamicin conjugate
A1-AcBut-CalichDMH, A1 antibody conjugated to calicheamicin using 4-(4'-acetylphenoxy)butanoic acid (AcBut)
A2-AcBut-CalichDMH, A2 antibody conjugated to calicheamicin using 4-(4'-acetylphenoxy)butanoic acid (AcBut)
A3-AcBut-CalichDMH, A3 antibody conjugated to calicheamicin using 4-(4'-acetylphenoxy)butanoic acid (AcBut)

The cytotoxicity of anti-5T4/calicheamicin conjugates was also assayed using a three-dimensional spheroid cell culture that more closely approximates an in vivo cellular environment. Spheroids were made essentially according to Yuhas et al. (1977) *Cancer Res.* 37:3639-3643. Briefly, $10^5$ cells in 5 ml of culture medium were seeded on 60 mm polystyrene cell culture dishes previously coated with 5 ml 0.65% tissue culture grade agar in culture medium (Sigma of St. Louis, Mo.). The dishes were incubated for 5-6 days at 37° C. and in 5% $CO_2$ in air. Spheroids with a diameter of 0.2 mm were selected and placed in a 24-well multiwell dish. Each well contained 0.5 ml agar underlay, 1 spheroid, and 1 ml culture medium overlay. The spheroids were then exposed to various concentrations (0, 0.091, 0.365, 1.46, 5.86, 23.44, 93.75 and 375 ng calicheamicin equivalents/ml) of calicheamicin, CMA-676 and anti-5T4/calicheamicin conjugates prepared using the A1 and A3 anti-5T4 antibodies and an AcBut linker. Both anti-5T4/calicheamicin conjugates significantly inhibited growth of MDAMB435/5T4 cells. See FIG. 8.

Example 7

Preparation and Binding Properties of Chimeric and Humanized Anti-5T4 Antibodies Chimeric H8, A1, A2, and A3 antibodies were constructed having murine H8 heavy chain and light chain variable regions sequences and human IgG4 heavy chain constant regions and human kappa light chain constant regions. The cysteine present at position 67 of the A1 heavy chain variable region was optionally changed to phenylalanine, and the cysteine present at position 91 of the A3 heavy chain variable region was optionally changed to tyrosine. These variants are set for in SEQ ID NO:2 (A1 VH) and SEQ ID NO:10 (A3 VH). The presence or absence of intronic sequences and the replacement of cysteine residues did not affect antibody expression. For cloning of sequences encoding IgG constant regions, intronic sequences were optionally deleted.

Humanized H8 was prepared as described in PCT International Publication No. WO 2006/031653. Humanized A1 antibodies were prepared by CDR grafting as described further herein below. The CDRs of the murine A1, A2, and A3 antibodies were identified using the AbM definition, which is based on sequence variability as well as the location of the structural loop regions. In general, human acceptor frameworks were selected on the basis that they are substantially similar to the framework regions of the murine antibodies, or which were most similar to the consensus sequence of the variable region subfamily. Consideration was also given to representation of the framework loci in humans, such that widely represented sequences were generally preferred over less populous sequences. Additional mutations of the human framework acceptor sequences were made to restore murine residues believed to be involved in antigen contacts and/or residues involved in the structural integrity of the antigen-binding site. The amino acid sequence may also be optimized for codon preference of CHO cells and to remove restriction enzyme sites. A peptide structure prediction program may be used to analyze the humanized variable heavy and light region sequences to identify and avoid post-translational protein modification sites introduced by the humanization design.

A humanized A1 heavy chain variable region (A1 VH version 1.0) was constructed to include the CDRs of murine A1 grafted onto a human DP-21 framework region (VH7 subgroup, Accession No. CAA43346, SEQ ID NO:88), which contains a framework mutation (S82A) and one back-mutation (E46K). Variants were prepared by removing the backmutation (A1 VH versions 1.1 and 1.2). A second humanized A1 heavy chain variable region was prepared by grafting A1 CDRs onto a human DP-54 germline framework region (A1 VH version 2.0). Six (6) backmutations were made to produce A1 VH version 2.1. As described further below, both A1 heavy chain variable regions retained 5T4 binding properties. The DP-21 and DP-54 framework regions show 63% amino acid sequence identity over their length, indicating that numerous amino acid changes may be made to while preserving the binding specificity of the antibody, including the ability to bind to a particular epitope. The similarity of humanized A1 heavy chain variable regions is shown in Table 10. Representative nucleotide sequences encoding humanized A1 heavy chain variable regions are set forth as SEQ ID NOs:48, 50, 53, and 55. Representative amino acid sequences of humanized A1 heavy chain variable regions are set forth as SEQ ID NOs:49, 51, 52, 54, and 56. See also FIGS. 9A-9B.

A humanized A1 light chain variable region was constructed to include the CDRs of murine A1 grafted onto human DPK24 (VKIV subgroup), DPK9 (VKI subgroup), and DPK23 (VKIII subgroup) germline framework regions. After incorporation of a S67Y backmutation into humanized A1 light chain variable region frameworks prepared with each of these frameworks demonstrated 5T4 binding. See below, including Table 13. The DPK24 framework region shows 74% and 73% amino acid sequence identity over its length to DPK9 and DPK23, respectively. The DPK9 framework region shows 74% amino acid sequence identity over its length to DPK23. The similarity of humanized A1 light chain variable regions is shown in Table 10. The multiple versions of humanized light chain variable framework regions demonstrate that numerous amino acid changes may be made to while preserving the binding specificity of the antibody, including the ability to bind to a particular epitope. Representative nucleotide sequences encoding humanized A1 light chain variable regions are set forth as SEQ ID NOs:57, 59, 61, 63, 65, 67, 69, 71, 73, and 75. Representative amino acid sequences of humanized A1 light chain variable regions are set forth as SEQ ID NOs:58, 60, 62, 64, 66, 68, 70, 72, 74, and 76. See also FIGS. 9C-9F.

TABLE 10

Relatedness of Humanized A1 Antibodies

| 1st Variable Region/2nd Variable Region | Percentage Identity |
|---|---|
| HuA1 VL v1.1 (SEQ ID NO: 60)/<br>HuA1 VL v2.4 protein (SEQ ID NO: 70) | 86% |
| HuA1 VL v1.1 (SEQ ID NO: 60)/<br>HuA1 VL v3.1 protein (SEQ ID NO: 75) | 86% |
| HuA1 VL v2.4 protein (SEQ ID NO: 70)/ | 85% |

TABLE 10-continued

Relatedness of Humanized A1 Antibodies

| 1$^{st}$ Variable Region/2$^{nd}$ Variable Region | Percentage Identity |
|---|---|
| HuA1 VL v3.1 protein (SEQ ID NO: 75) HuA1 VH v1.1 protein (SEQ ID NO: 52)/ HuA1 VH v2.0 protein (SEQ ID NO: 54) | 78% |

Humanized A2 and A3 antibodies were designed using a similar strategy. Representative amino acid sequences of humanized A2 heavy chain variable regions and humanized A2 light chain variable regions are set forth as SEQ ID NOs: 77-78 and SEQ ID NOs:79-80, respectively. See also FIG. 9G. Representative amino acid sequences of humanized A3 heavy chain variable regions and humanized A3 light chain variable regions are set forth as SEQ ID NOs:81-82 and SEQ ID NOs:83-84, respectively. See also FIG. 9H.

To assess the novelty of humanized A1, A2, and A3 heavy chain and light chain variable regions, BLASTn and BLASTp analysis was performed as described in Example 1. The results are presented in Table 11.

TABLE 11

BLASTn and BLASTp Analysis

| Query Sequence | Identity (%) of Closest Subject Sequence | Description of Closest Subject Sequence |
|---|---|---|
| Humanized A1 VL version 1.1 DNA (SEQ ID NO: 59) | 83%* | DEFINITION *Homo sapiens* partial mRNA for immunoglobulin kappa chain variable region (IGKV2 gene). ACCESSION AM040532 |
| Humanized A1 VL version 1.1 protein (SEQ ID NO: 60) | 82% | DEFINITION Ig kappa chain V-IV region B17 precursor. ACCESSION P06314 |
| Humanized A1 VL version 2.4 DNA (SEQ ID NO: 69) | 85%* | DEFINITION *Homo sapiens* clone SC4064 anti-rabies virus immunoglobulin light chain variable region mRNA, complete cds. ACCESSION AY942044 |
| Humanized A1 VL version 2.4 protein (SEQ ID NO: 70) | 92% | DEFINITION anti-alpha 4 integrin humanized immunoglobulin kappa chain V region. ACCESSION AAA62146 |
| Humanized A1 VL version 3.1 DNA (SEQ ID NO: 75) | 84%* | DEFINITION *Homo sapiens* clone 136e06 anti-tetanus toxoid immunoglobulin light chain variable region (IGL@) mRNA, partial cds. ACCESSION AY867377 |
| Humanized A1 VL version 3.1 protein (SEQ ID NO: 76) | 84% | DEFINITION anti-*Burkholderia mallei* scFv antibody [synthetic construct]. ACCESSION ABI97018 |
| Humanized A1 VH version 1.1 DNA (SEQ ID NO: 50) | 88%* | DEFINITION *Homo sapiens* ID: CLL097 IgA heavy chain variable region mRNA, partial cds. ACCESSION AF021940 |
| Humanized A1 VH version 1.1 protein (SEQ ID NO: 51) | 90% | DEFINITION IgA heavy chain variable region [*Homo sapiens*]. ACCESSION AAC09074 |
| Humanized A1 VH version 2.0 DNA (SEQ ID NO: 53) | 81%* | DEFINITION *Homo sapiens* clone 23u-45 immunoglobulin heavy chain variable region (IGH) mRNA, partial cds. ACCESSION AF062241 |
| Humanized A1 VH version 2.0 protein (SEQ ID NO: 54) | 77% | DEFINITION Chain D, Insights Into Erbb Signaling From The Structure Of The Erbb2-Pertuzumab Complex. ACCESSION 1S78_D |
| Humanized A2 VL version 1.0 protein (SEQ ID NO: 79) | 87% | DEFINITION Chain A, Crystal Structure Of The Fab Fragment Of A Human Monoclonal Igm Cold Agglutinin. ACCESSION 1QLR_A |
| Humanized A2 VL version 2.0 protein (SEQ ID NO: 80) | 83% | DEFINITION kappa 1 immunoglobulin light chain [*Homo sapiens*]. ACCESSION AAD29608 |
| Humanized A2 VH version 1.0 protein (SEQ ID NO: 77) | 88% | DEFINITION Chain A, The Crystal Structure Of A Humanized Antibody Fv 528. ACCESSION 1WT5_A |
| Humanized A2 VH version 2.0 protein (SEQ ID NO: 78) | 78% | DEFINITION Chain D, Insights Into Erbb Signaling From The Structure Of The Erbb2-Pertuzumab Complex. ACCESSION 1S78_D |
| Humanized A3 VL version 1.0 protein (SEQ ID NO: 83) | 85% | DEFINITION immunoglobulin kappa light chain VLJ region [*Homo sapiens*]. ACCESSION BAC01708 |
| Humanized A3 VL version 2.0 protein (SEQ ID NO: 84) | 90% | DEFINITION HerMel [synthetic construct]. ACCESSION CAL47329 |
| Humanized A3 VH version 1.0 protein (SEQ ID NO: 81) | 79% | DEFINITION Igh-1a protein [*Mus musculus*]. ACCESSION AAH80671 |
| Humanized A3 VH version 2.0 protein (SEQ ID NO: 82) | 77% | DEFINITION Igh-1a protein [*Mus musculus*]. ACCESSION AAH80671 |

*When Query Coverage = 100%

FIGS. 10A-10B show additional heavy chain variable region sequences that may be used as frameworks for preparation of humanized A1, A2, and A3 anti-5T4 antibodies. FIGS. 11-13 show additional light chain variable region sequences that may be used as a framework for preparation of humanized A1, A2, and A3 anti-5T4 antibodies. FIG. 14 shows representative constant regions that may be used for the preparation of chimeric and humanized A1, A2, and A3 anti-5T4 antibodies.

To assess the binding specificity and affinity of the chimeric and humanized H8, A1, A2, and A3 antibodies, BIACORE® analysis was performed using human 5T4 antigen immobilized on a CM5 chip. See Example 2. The results for chimeric A1, A2, and A3 antibodies are shown in Table 12 below.

TABLE 12

Results of BIACORE ® Assay

| Antibody | KD (M) | KA (1/M) | kd (1/s) | ka (1/Ms) |
|---|---|---|---|---|
| Humanized H8 | $1.5 \times 10^{-10}$ | $6.5 \times 10^{9}$ | $4.0 \times 10^{-5}$ | $2.6 \times 10^{5}$ |
| Chimeric A1 | $4.4 \times 10^{-10}$ | $2.3 \times 10^{9}$ | $6.7 \times 10^{-5}$ | $1.5 \times 10^{5}$ |
| Chimeric A2 | $1.8 \times 10^{-9}$ | $5.7 \times 10^{8}$ | $2.5 \times 10^{-4}$ | $1.4 \times 10^{5}$ |
| Chimeric A3 | $\sim 1.8 \times 10^{-10}$ | $\sim 5.4 \times 10^{9}$ | $\sim 1.0 \times 10^{-5}$ | $\sim 5.4 \times 10^{4}$ |
| Chimeric A1 + C67F | $3.8 \times 10^{-10}$ | $2.6 \times 10^{9}$ | $6.3 \times 10^{-5}$ | $1.7 \times 10^{5}$ |
| Chimeric A3 + C91Y | $5.9 \times 10^{-9}$ | $1.7 \times 10^{9}$ | $1.6 \times 10^{-5}$ | $2.7 \times 10^{4}$ |

In general, chimerization/humanization increased the affinity of H8, A1, A2, and A3 to human 5T4. Compare Table 3. The increase in binding affinities appears to result primarily from a slower dissociation of the antibody and antigen rather than a faster association. The chimeric A2 and A3 antibodies showed the most improved binding properties following chimerization.

All humanized A1 heavy chain variable regions retained 5T4 binding properties. In addition, removal of the K46 backmutation from humanized A1 heavy chain variable region did not affect 5T4 binding properties. Humanized A1 light chain variable regions showed compromised 5T4 binding properties. Humanized A1 light chain variable regions constructed using DPK9 and DPK23 frameworks bound 5T4 with higher affinity than a humanized A1 light chain variable regions constructed using DPK24 frameworks. Backmutations were incorporated to restore and/or optimize 5T4 binding. Replacement of the serine residue at position 67 with a tyrosine residue, as seen in the murine A1 framework region, completely restored 5T4 antigen binding properties. See Table 13.

TABLE 13

Inhibition of Biotinylated Chimeric A1
Antibody Binding to Human 5T4 by ELISA

| Version A1 Antibody | IC$_{50}$ |
|---|---|
| Chimeric A1 | 16-20 nM |
| huA1 V$_H$ v2.0 + huA1 V$_L$ v1.1 | >1 µM |
| huA1 V$_H$ v2.0 + huA1 V$_L$ v1.1 | 28 nM |
| huA1 V$_H$ v2.0 + huA1 V$_L$ v2.0 | >1 µM |
| huA1 V$_H$ v2.0 + huA1 V$_L$ v2.4 | 16 nM |
| huA1 V$_H$ v2.0 + huA1 V$_L$ v3.0 | >1 µM |
| huA1 V$_H$ v2.0 + huA1 V$_L$ v3.1 | 27 nM | huA1, humanized A1
v, version

Example 8

Species Cross-Reactivity of Anti-5T4 Antibodies

The cross-species reactivity of anti-5T4 antibodies disclosed herein was assayed to determine relevant species for in vivo efficacy studies and toxicology analysis. Correlation of binding activity and relatedness of the different 5T4 ectodomains was also used to further describe the epitope bound by each antibody. Binding assays were performed using 5T4 ectodomains from various species fused to human IgG1 Fc. The percentage identity of each ectodomain region to human 5T4 is shown in Table 14.

TABLE 14

Relatedness of 5T4 From Different Species

| Species | Percentage Identity to Human 5T4 | Amino Acids of Ectodomain |
|---|---|---|
| Human | 100 | 1-355 |
| Mouse | 84.0 | 1-361 [a] |
| Rat | 83.1 | 1-361 [a] |
| Chimpanzee (partial sequence - 396/420 amino acids) | ~99.5 | 1-355 |
| Cynomologous Monkey | 96.7 | 1-355 |
| Black-Tailed Marmoset (partial sequence - 367/420 amino acids) | ~94.6 | 1-355 |
| Dog | 87.9 | 1-355 |
| Cow | 86.9 | 1-355 |

[a] Contains 6 amino acid direct repeat within hydrophilic domain

The full-length or partial sequences of 5T4 from human, mouse, rat, dog, and cow have been disclosed previously as GenBank Accession Nos. Z29083 (human, SEQ ID NO:87), AJ012160 (mouse), BC087011 (rat), XM539020 (dog), and XM593502 (cow). A virtual partial sequence of chimpanzee 5T4 was generated using an alignment of mRNA and genomic sequences. Nucleic acids encoding 5T4 proteins were isolated from cynomologous monkey and black-tailed marmoset. The amino acid sequences of these additional 5T4 antigens are shown in FIG. 15 and are also set forth as SEQ ID NO:86 (cynomologous monkey) and SEQ ID NO:85 (black-tailed marmoset).

To assess the novelty of cynomologous monkey and black-tailed marmoset sequences, BLAST analyses were performed as described in Example 2. When using the full-length black-tailed marmoset 5T4 amino acid sequence as a query sequence, the closest subject sequence was identified as human 5T4 (GenBank Accession No. NP_006661.1), with 94% identity (302/320 amino acids). The sequences also differed at the carboxyl terminus, with amino acids 1-19 of SEQ ID NO:85 not aligning with the closest subject sequence. When using the full-length cynomologous monkey 5T4 amino acid sequence as a query sequence, the closest non-virtual subject sequence was identified as a trophoblast glycoprotein precursor also from cynomologous monkey (GenBank Accession No. BAE00432.1), with 99% identity (364/366 amino acids). The sequences also differed at the carboxyl terminus, with amino acids 1-25 of SEQ ID NO:86 not aligning with the closest non-virtual subject sequence.

To assay binding of anti-5T4 antibodies, 5T4 ectodomain/Fc fusion proteins were transiently transfected into COS-1 cells, and ELISA assays were performed. Non-relevant human IgG4 and IgG1 antibodies were used as controls. The cross-species reactivity of anti-5T4 antibodies is summarized in Table 15.

TABLE 15

Cross-Reactivity of Anti-5T4 Antibodies (ED50 in nM)

|  | huH8 γ4 | huH8 γ1 | ChiA1 γ4 | ChiA2 γ4 | ChiA3 γ4 |
|---|---|---|---|---|---|
| human | 0.19 | 0.20 | 0.28 | 0.21 | 0.20 |
| chimpanzee | 0.19 | 0.22 | 0.27 | 0.22 | 0.20 |
| black-tailed marmoset | +/− | +/− | 0.24 | 0.22 | − |
| cynomologous monkey | − | − | 0.18 | 0.18 | 0.23 |
| rat | − | − | +/− | − | − |
| mouse | − | − | − | − | − | huH8 γ4, humanized H8 antibody having IgG4 constant regions
huH8 γ1, humanized H8 antibody having IgG1 constant regions
ChiA1 γ4, chimeric A1 antibody having IgG4 constant regions
ChiA2 γ4, chimeric A2 antibody having IgG4 constant regions
ChiA3 γ4, chimeric A3 antibody having IgG4 constant regions
(+/−), partial binding
(−), no binding

What is claimed:

1. An isolated antibody, or fragment thereof, that specifically binds human 5T4 antigen, wherein the antibody or antibody fragment comprises an antigen binding domain of, competes for 5T4 binding with, or binds a 5T4 epitope bound by, an antibody comprising a heavy chain variable region having an amino acid sequence set forth as SEQ ID NO:2 and a light chain variable region having an amino acid sequence set forth as SEQ ID NO:4.

2. The antibody of claim 1, which is a chimeric antibody, a humanized antibody, a single chain antibody, a Fab fragment, a $F(ab)_2$ fragment, a Fv fragment, a tetrameric antibody, a tetravalent antibody, a multispecific antibody, or a fusion protein.

3. The antibody of claim 1, which is a murine monoclonal antibody.

4. The antibody of claim 1, which has a binding affinity for human 5T4 antigen of at least about $1 \times 10^{-7}$ to about $1 \times 10^{-12}$ M.

5. The antibody of claim 1, which specifically targets 5T4-expressing cells in vivo.

6. The antibody of claim 3, wherein the murine monoclonal antibody comprises a heavy chain variable region comprising an amino acid sequence of residues 20-138 of SEQ ID NO:2.

7. The antibody of claim 3, wherein the murine monoclonal antibody comprises a light chain variable region comprising an amino acid sequence of residues 21-127 of SEQ ID NO:4.

8. The antibody of claim 3, wherein the murine monoclonal antibody comprises a heavy chain variable region comprising an amino acid sequence of residues 20-138 of SEQ ID NO:2, and wherein the light chain variable region of the murine monoclonal antibody comprises an amino acid sequence of residues 21-127 of SEQ ID NO:4.

9. The antibody of claim 2, which is a chimeric or humanized anti-5T4 antibody.

10. The chimeric or humanized antibody of claim 9, which comprises human constant regions.

11. The chimeric or humanized antibody of claim 10, which comprises a human kappa light chain constant region.

12. The chimeric or humanized antibody of claim 10, which comprises a human IgG1, IgG2, IgG3, or IgG4 heavy chain constant region.

13. The chimeric or humanized antibody of claim 12, wherein the human IgG4 heavy chain constant region comprises proline at position 241.

14. The humanized antibody of claim 9, which comprises at least one light chain variable region and at least one heavy chain variable region comprising,
    framework regions comprising human residues of a human antibody framework region; and
    wherein the at least one light chain variable region comprises three CDRs of SEQ ID NO:4.

15. The humanized antibody of claim 14, wherein the human residues are human framework residues selected from the group consisting of:
    (a) a human antibody heavy chain framework region of any one of SEQ ID NOs:14-23, 77, and 88-93;
    (b) a human antibody light chain framework region of any one of SEQ ID NOs:28-34, 35-44, and 94-99;

(c) a consensus sequence of a heavy chain framework region of (a); and
(d) a framework region that is at least 63% identical to a framework region of (a)-(c).

16. The humanized antibody of claim 14, wherein the at least one heavy chain of the humanized antibody comprises a variable region comprising three CDRs of SEQ ID NO:2.

17. The chimeric or humanized antibody of claim 9, which comprises a heavy chain variable region sequence comprising:
   (a) an amino acid sequence of residues 20-138 of SEQ ID NO:2; or
   (b) an amino acid sequence of any one of SEQ ID NOs:49, 51, 52, 54, or 56.

18. The chimeric or humanized antibody of claim 9, which comprises a light chain variable region sequence comprising:
   (a) an amino acid sequence of residues 21-127 of SEQ ID NO:4; or
   (b) an amino acid sequence of any one of SEQ ID NOs: 58, 60, 62, 64, 66, 68, 70, 72, 74, or 76.

19. An antibody/drug conjugate for drug delivery comprising:
   (a) an antibody according to claim 1; and
   (b) a drug, which is directly or indirectly bound to the antibody.

20. The antibody/drug conjugate of claim 19, wherein the drug is a therapeutic agent selected from the group consisting of a cytotoxin, a radioisotope, an immunomodulatory agent, an anti-angiogenic agent, an anti-proliferative agent, a pro-apoptotic agent, a chemotherapeutic agent, and a therapeutic nucleic acid.

21. The antibody/drug conjugate of claim 20, wherein the therapeutic agent is a cytotoxin.

22. The antibody/drug conjugate of claim 20, wherein the cytotoxin is an antibiotic, an inhibitor of tubulin polymerization, an alkylating agent, a protein synthesis inhibitor, a protein kinase inhibitor, a phosphatase inhibitor, a topoisomerase inhibitor, or an enzyme.

23. The antibody/drug conjugate of claim 20, wherein the cytotoxin is an antibiotic.

24. The antibody/drug conjugate of claim 23, wherein the antibiotic is calicheamicin.

25. The antibody/drug conjugate of claim 24, wherein the calicheamicin is an N-acetyl derivative or disulfide analog of calicheamicin.

26. The antibody/drug conjugate of claim 25, wherein the calicheamicin is N-acetyl-γ-calicheamicin.

27. The antibody/drug conjugate of claim 19, wherein the drug is bound to the antibody via a linker.

28. The antibody/drug conjugate of claim 27, wherein the linker is selected from the group consisting of 4-(4'acetylphenoxy)butanoic acid (AcBut), 3-acetylphenyl acidic acid (AcPac), 4-mercapto-4-methyl-pentanoic acid (Amide), and derivatives thereof.

29. An isolated antibody that specifically binds to a human 5T4 epitope comprising residues 173-252 and 276-355 of SEQ ID NO:87.

30. The chimeric or humanized antibody of claim 9, which comprises:
   (a) a light chain variable region comprising an amino acid sequence selected from the group consisting of an amino acid sequence of residues 21-127 of SEQ ID NO:4 and any one of SEQ ID NOs: 58, 60, 62, 64, 66, 68, 70, 72, 74, or 76; and
   (a) a heavy chain variable region comprising an amino acid sequence selected from the group consisting of residues 20-138 of SEQ ID NO:2 and any one of SEQ ID NOs:49, 51, 52, 54, or 56.

31. The chimeric or humanized antibody of claim 9, which comprises:
   (a) a light chain variable region comprising an amino acid sequence of SEQ ID NO: 70; and
   (a) a heavy chain variable region comprising an amino acid sequence of SEQ ID NO: 54.

\* \* \* \* \*

UNITED STATES PATENT AND TRADEMARK OFFICE
CERTIFICATE OF CORRECTION

PATENT NO.         : 8,044,178 B2
APPLICATION NO.    : 11/684329
DATED              : October 25, 2011
INVENTOR(S)        : Erwin R. Boghaert et al.

It is certified that error appears in the above-identified patent and that said Letters Patent is hereby corrected as shown below:

Figure 15 – delete "Cynomologous" and insert --Cynomolgus--

Column 8, line 15, delete "cynomologous" and insert --cynomolgus--

Column 32, line 59, delete "cynomologus" and insert --cynomolgus--

Column 45, line 52, delete "cynomologous" and insert --cynomolgus--

Column 46, line 16, delete "cynomologous" and insert --cynomolgus--

Column 46, line 29, delete "cynomologous" and insert --cynomolgus--

Column 46, line 34, delete "cynomologous" and insert --cynomolgus--

Column 46, in the heading of Table 5, after "Results" insert --of--

Column 54, line 42, delete "cynomologous" and insert --cynomolgus--

Column 54, line 58, delete "cynomologous" and insert --cynomolgus--

Column 54, line 61, delete "cynomologous" and insert --cynomolgus--

Column 54, line 64, delete "cynomologous" and insert --cynomolgus--

Column 55, line 6, delete "cynomologous" and insert --cynomolgus--

Column 55, line 9, delete "cynomologous" and insert --cynomolgus--

Column 56, line 10, delete "cynomologous" and insert --cynomolgus--

Column 125, line 4, delete "Cynomologous" and insert --cynomolgus--

Signed and Sealed this
Tenth Day of April, 2012

David J. Kappos
*Director of the United States Patent and Trademark Office*

UNITED STATES PATENT AND TRADEMARK OFFICE
CERTIFICATE OF CORRECTION

PATENT NO. : 8,044,178 B2
APPLICATION NO. : 11/684329
DATED : October 25, 2011
INVENTOR(S) : Boghaert et al.

It is certified that error appears in the above-identified patent and that said Letters Patent is hereby corrected as shown below:

On the Title Page

Item (75), ninth inventor's Name:
Change "Kodandgattil R. Sreekumar" to -- Sreekumar Raman Kodandgattil --.

Signed and Sealed this
Twentieth Day of August, 2019

Andrei Iancu
*Director of the United States Patent and Trademark Office*